United States Patent
Dimitroff et al.

(10) Patent No.: US 8,598,323 B2
(45) Date of Patent: Dec. 3, 2013

(54) GALECTIN-IMMUNOGLOBULIN CHIMERIC MOLECULES

(75) Inventors: Charles J. Dimitroff, Hanover, MA (US); Filiberto Cedeno Laurent, Jamaica Plain, MA (US); Steven R. Barthel, Allston, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 0 days.

(21) Appl. No.: 13/378,229

(22) PCT Filed: Jun. 22, 2010

(86) PCT No.: PCT/US2010/039504
§ 371 (c)(1),
(2), (4) Date: Mar. 14, 2012

(87) PCT Pub. No.: WO2011/005523
PCT Pub. Date: Jan. 13, 2011

(65) Prior Publication Data
US 2012/0171205 A1 Jul. 5, 2012

Related U.S. Application Data

(60) Provisional application No. 61/219,531, filed on Jun. 23, 2009.

(51) Int. Cl.
*C07K 16/00* (2006.01)
*C07K 17/00* (2006.01)

(52) U.S. Cl.
USPC .................. 530/391.5; 530/391.7; 530/391.9

(58) Field of Classification Search
None
See application file for complete search history.

(56) References Cited

FOREIGN PATENT DOCUMENTS

WO WO2008053049 * 8/2008

OTHER PUBLICATIONS

Battig et al. Enhanced apoptotic activity of a structurally optimized form of galectin-1. Mol. Immunol. 2004, 41(1):9-18).*
Tsuchiyama et al. Efficacy of galectins in the amelioration of nephrotoxic serum nephritis in Wistar Kyoto rats. Kidney Int. Nov. 2000;58(5):1941-52.*
Cedeno-Laurenta et al. Galectin-1 research in T cell immunity: Past, present and future. Clinical Immunology vol. 142, Issue 2, Feb. 2012, pp. 107-116.*
Camby et al. Galectin-1: a small protein with major functions. Glycobiology (Nov. 2006) 16 (11): 137R-157R.*
Attwood Tk. Genomics. The Babel of bioinformatics. Science. 290(5491):471-473, 2000.*
Skolnick et al. From genes to protein structure and function: novel applications of computational approaches in the genomic era. Trends Biotechnol. 18(1):34-9, 2000.*
Rabinovich et al. Recombinant galectin-1 and its genetic delivery suppress collagen-induced arthritis via T cell apoptosis. J Exp Med. Aug. 2, 1999;190(3):385-98.*
Barondes et al., "Galectins: a family of animal beta-galactoside-binding lectins," Cell, 76(4):597 (1994).
Barthel et al., "Alpha 1,3 fucosyltransferases are master regulators of prostate cancer cell trafficking," Proc. Natl. Acad. Sci. USA, 106:19491-19496 (2009).
Baum et al., "Amelioration of graft versus host disease by galectin-1," Clin. Immunol , 109:295-307 (2003).
Cedeno-Laurent et al., "Development of a Nascent Galectin-1 Chimeric Molecule for Studying the Role of Leukocyte Galectin-1 Ligands and Immune Disease Modulation," The Journal of Immunology, 185(8):4659-4672 (2010).
Chai et al., "CD4+CD25+T cells as immunoregulatory T cells in vitro," Eur. J. Immunol , 32:2365-2375 (2002).
Cho et al., "Galectin-1, a beta-galactoside-binding lectin in Chinese hamster ovary cells. I. Physical and chemical characterization," J. Biol. Chem., 270(10):5198 (1995).
Clark et al., "A novel method for the isolation of skin resident T cells from normal and diseased human skin," J. Invest. Dermatol., 126:1059-1107 (2006).
Clark et al., "IL-15 and dermal fibroblasts induce proliferation of natural regulatory T cells isolated from human skin," Blood, 109:194-202 (2007).
Hirabayashi et al., "Effect of amino acid substitution by sited-directed mutagenesis on the carbohydrate recognition and stability of human 14-kDa beta-galactoside-binding lectin," J. Biol. Chem., 266:23648-23653 (1991).
Hirabayashi et al., "Oligosaccharide specificity of galectins: a search by frontal affinity chromatography," Biochim Biophys. Acta., 1572:232-254 (2002).
Hughes, "Galectins as modulators of cell adhesion," Biochimie, 83(7):667 (2001).
International Search Report issued in PCT/US2010/039504 on Mar. 10, 2011.
Juszczynski et al., "The AP1-dependent secretion of galectin-1 by Reed Sternberg cells fosters immune privilege in classical Hodgkin lymphoma," Proc. Natl. Acad. Sci. USA, 104:13134-13139 (2007).
Kingsley et al., "CD25+CD4+ regulatory T cells prevent graft rejection: CTLA-4- and IL-10- dependent immunoregulation of alloresponses," J. Immunol , 168:1080-1086 (2002).
Kryczek et al., "FOXP3 defines regulatory T cells in human tumor and autoimmune disease," Cancer Res., 69:3995-4000 (2009).
Leppanen et al., "Dimeric galectin-1 binds with high affinity to alpha2,3-sialylated and non-sialylated terminal N-acetyllactosamine units on surface-bound extended glycans," J. Biol. Chem., 280(7):5549-5562 (2004).

(Continued)

*Primary Examiner* — Maher Haddad
(74) *Attorney, Agent, or Firm* — Fish & Richardson P.C.

(57) ABSTRACT

Described are Galectin-1/Ig fusion constructs and methods of use thereof, e.g., in diagnostic and biomedical assays, and as therapeutic agents for the treatment of conditions associated with immune dysfunction, e.g., autoimmune diseases, and cancers.

5 Claims, 33 Drawing Sheets

(56) References Cited

OTHER PUBLICATIONS

Levi et al., "Isolation and physicochemical characterization of electrolectin, a beta-D-galactoside binding lectin from the electric organ of Electrophorus electricus," J. Biol. Chem., 256:5735-5740 (1981).

Lopez-Lucendo et al., "Growth-regulatory human galectin-1: crystallographic characterisation of the structural changes induced by single-site mutations and their impact on the thermodynamics of ligand binding," J. Mol. Biol., 343(4):957 (2004).

Motran et al., "Galectin-1 functions as a Th2 cytokine that selectively induces Th1 apoptosis and promotes Th2 function," Eur. J. Immunol, 38:3015-3027 (2008).

Nickel, "Unconventional secretory routes: direct protein export across the plasma membrane of mammalian cells," Traffic, 6(8):607 (2005).

Pace et al., "Preparation of recombinant human galectin-1 and use in T-cell death assays," Methods Enzymol., 363:499-518 (2003).

Perillo et al., "Apoptosis of T cells mediated by galectin-1," Nature, 378:736-739 (1995).

Perone et al., "Suppression of autoimmune diabetes by soluble galectin-1," J. Immunol, 182:2641-2653 (2009).

Rabinovich et al., "An emerging role for galectins in tuning the immune response: lessons from experimental models of inflammatory disease, autoimmunity and cancer," Scand. J. Immunol, 66(2-3):143 (2007).

Santucci et al., "Galectin-1 exerts immunomodulatory and protective effects on concanavalin A-induced hepatitis in mice," Hepatology, 31:399-406 (2000).

Schwarz et al., "Thermodynamics of bovine spleen galectin-1 binding to disaccharides: correlation with structure and its effect on oligomerization at the denaturation temperature," Biochemistry, 37(17):5867 (1998).

Song et al., "Novel fluorescent glycan microarray strategy reveals ligands for galectins," Chem. Biol., 16:36-47 (2009).

Stowell et al., "Galectin-1 induces reversible phosphatidylserine exposure at the plasma membrane," Mol. Biol. Cell, 20:1408-1418 (2009).

Stowell et al., "Human galectin-1, -2, and -4 induce surface exposure of phosphatidylserine in activated human neutrophils but not in activated T cells," Blood, 109:219-227 (2007).

Stowell et al., "Ligand reduces galectin-1 sensitivity to oxidative inactivation by enhancing dimer formation," J. Biol. Chem., 284:4989-4999 (2009).

Toscano et al., "Differential glycosylation of TH1, TH2, and TH-17 effector cells selectively regulates susceptibility to cell death," Nat. Immunol, 8.825-834 (2007).

Toscano et al., "Galectin-1 suppresses autoimmune retinal disease by promoting concomitant Th2- and T regulatory-mediated anti-inflammatory responses," J. Immunol., 176:6323-6332 (2006).

Tsai et al., "Galectin-1 promotes immunoglobulin production during plasma cell differentiation," J. Immunol., 181(7):4570-4579 (2008).

Va der Leij et al., "Dimeric galectin-1 induces IL-10 production in T-lymphocytes: an important tool in the regulation of the immune response," J. Pathol., 204:511-518 (2004).

Van der Leij et al., "Strongly enhanced IL-10 production using stable galectin-1 homodimers," Mol. Immunol., 44:506-513 (2007).

Von Gunten et al., "Intravenous immunoglobulin contains a broad repertoire of anticarbohydrate antibodies that is not restricted to the IgG2 subclass," J. Allergy Clin. Immunol., 123:1268-1276 e1215 (2009).

Walz et al., "Recognition by ELAM-1 of the sialyl-Lex determinant on myeloid and tumor cells," Science, 250(4984):1132-1135 (1990).

\* cited by examiner

Figure 4
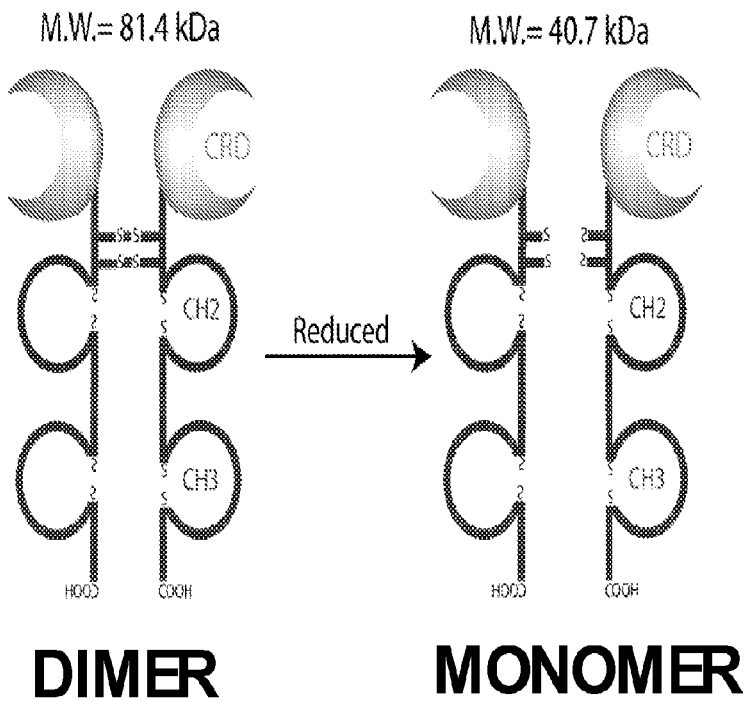
DIMER → MONOMER
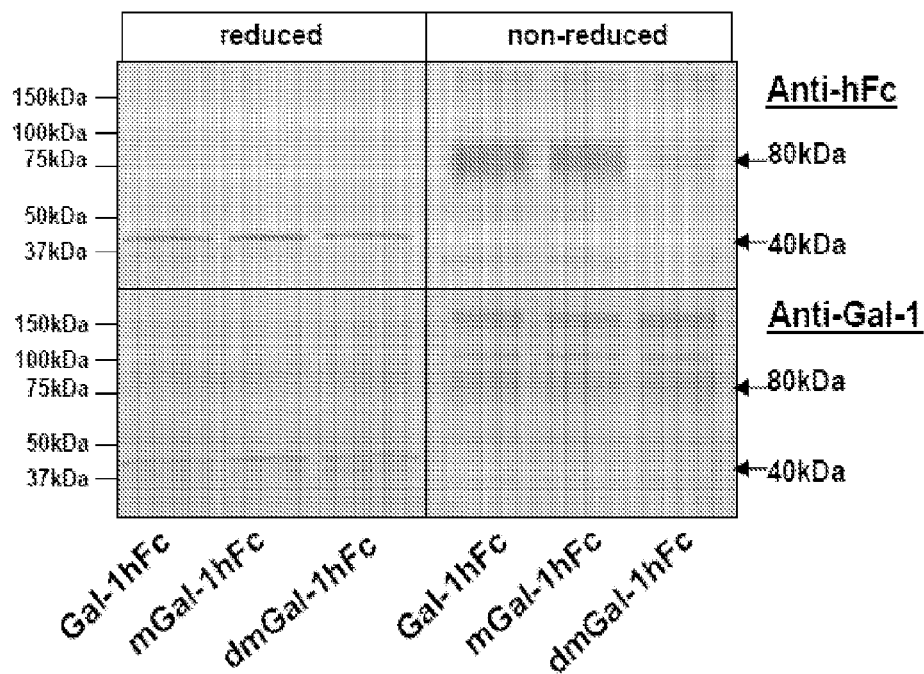
Figure 5

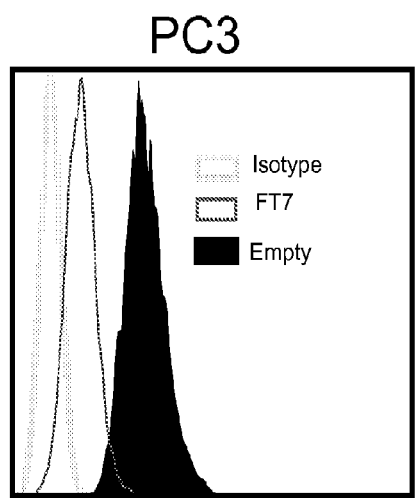
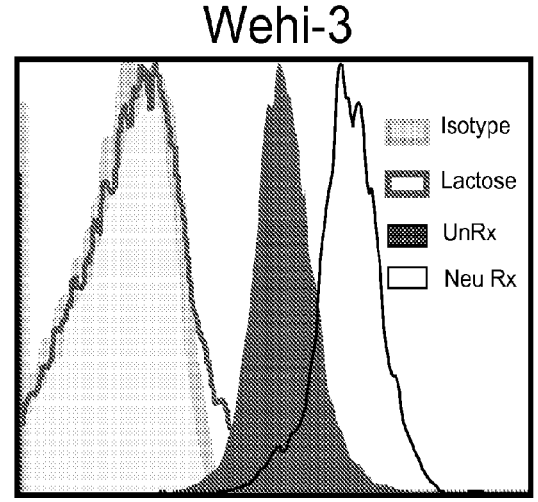
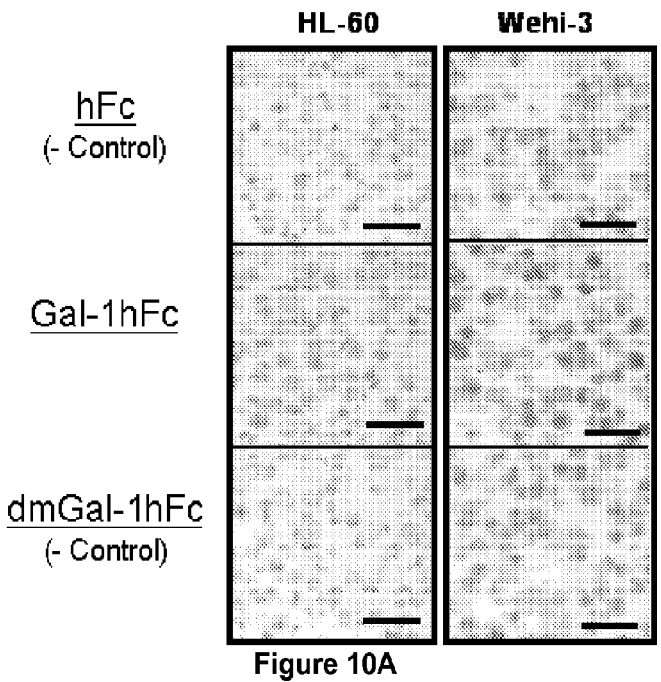
Figure 9A
Figure 9B
Figure 10A

Figure 22

MACGLVASNLNLKPGECLKVRGEVASDAKSFVLNLGKDSNNLCLH
FNPRFNAHGDANTIVCNTKEDGTWGTEHREPAFPFQPGSITEVCI
TFDQADLTIKLPDGHEFKFPNRLNMEAINYMAADGDFKIKC[VA]FE
**RSDKTHTCPPCPAPELLGGPSVFLFPPKPKDTLMISRTPEVTCVV
VDVSHEDPEVKFNWYVDGVEVHNAKTKPREEQYNSTYRVVSVLTV
LHQDWLNGKEYKCKVSNKALPAPIEKTISKAKGQPREPQVYTLPP
SREEMTKNQVSLTCLVKGFYPSDIAVEWESNGQPENNYKTTPPVL
DSDGSFFLYSKLTVDKSRWQQGNVFSCSVMHEGLHNHYTQKSLSL
SPGK** (SEQ ID NO: 17)

Regular Font = Galectin-1 (14.9 kDa)
**In box (RS) = linker (from Bgl II restriction digest) (0.3 kDa)
Bold = Fc region containing CH2 and CH3 domains of the IgG heavy chain along with the hinge region (25.6 kDa)**

GALECTIN-IMMUNOGLOBULIN CHIMERIC MOLECULES

CLAIM OF PRIORITY

This application is a 371 application of International Application No. PCT/US2010/039504, filed on Jun. 22, 2010, and claims the benefit of U.S. Patent Application Ser. No. 61/219,531, filed on Jun. 23, 2009, the entire contents of which are hereby incorporated by reference.

FEDERALLY SPONSORED RESEARCH OR DEVELOPMENT

This invention was made with Government support under Grant No. RO1 AT004628-01A1 awarded by the National Center for Complementary and Alternative Medicine at the National Institutes of Health. The Government has certain rights in the invention.

TECHNICAL FIELD

This invention relates to Galectin-Immunoglobulin Chimeric Molecules, and methods of use thereof.

BACKGROUND

Over the last twenty years, the study of carbohydrate-binding proteins (lectins) and their significance in immunology has intensified. Galectins, for example, embody a group of 15 β-galactoside-binding proteins that profoundly impact the differentiation of T lymphocytes (T cells) to help shape the strength of T cell-mediated inflammation, including autoimmune responses. In fact, galectin-1 can lower the level of effector T helper (Th) 1 and Th17 cell subsets, while promoting the survival of T regulatory (Treg) cell and generation of a Th2 cell profile. Controlling T cell differentiation in this manner yields an anti-inflammatory phenotype, thus effective galectin-1 molecules are useful as anti-inflammatory therapeutics.

SUMMARY

At least in part, the present invention is based on the development of novel Galectin-Ig fusion constructs. These fusion proteins have the ability to behave as a stable, high-affinity receptor that binds native ligands on cells (or in cell lysates), and as an anti-IgG Fc probe in immuno-detection assays, including Western blotting, flow cytometry, and immunohistochemistry. These new glycobiological probes have therapeutic application for biomedical research and clinical utility. Although the present description will use Galectin-1 as an example, other Galectins could be used.

Thus in one aspect the invention features isolated Galectin-1-Ig (Gal-Ig) fusion constructs. The constructs include a first portion comprising a Galectin-1 polypeptide, and a second portion comprising an Fc fragment of an immunoglobulin, linked in frame with the first portion, optionally with a linker sequence between the first and second portions. In some embodiments, the fusion construct has the same glycan binding profile as the mouse Galectin-1, and is able to induce apoptosis in activated T cells. In some embodiments, the Galectin-1 polypeptide is a mouse Galectin-1 polypeptide (mGal); an exemplary mouse Galectin-1 polypeptide is at least 95% identical to SEQ ID NO:1 or 2. In some embodiments, the Fc fragment is from a human immunoglobulin, e.g., a human IgG1, e.g., a human IgG1 that is at least 95% identical to SEQ ID NO:4.

In another aspect, the invention features nucleic acids encoding the isolated fusion constructs described herein, vectors including those nucleic acids, and host cells including (and optionally expressing) those vectors. In some embodiments, the host cell is from a cell line, e.g., a mammalian cell line, e.g., a human or mouse cell line, e.g., a J558L mouse haemocytoma cell line.

In another aspect, the invention provides method of obtaining a preparation comprising a Gal-Ig fusion construct as described herein. The methods include culturing the host cells described herein under conditions sufficient for expression of the Gal-Ig fusion construct, and isolating the Gal-Ig fusion construct from the cells, thereby obtaining a preparation comprising the Gal-Ig fusion construct.

In a further aspect, the invention features pharmaceutical compositions including the Gal-Ig fusion constructs described herein, and a physiologically acceptable carrier.

A further aspect of the invention features methods for treating a subject having an autoimmune disorder, the method comprising administering to the subject a therapeutically effective amount of a Gal-Ig fusion construct described herein, e.g., in a pharmaceutical composition as described herein. The methods can be used to treat, e.g., multiple sclerosis or autoimmune rheumatoid arthritis.

Yet another aspect of the invention provides methods for treating a subject having a cancer characterized by abnormal proliferation of cells expressing a Galactin-1 ligand on the cell surface. The methods include administering to the subject a therapeutically effective amount of t a Gal-Ig fusion construct described herein, e.g., in a pharmaceutical composition as described herein. The methods can be used to treat, e.g., hematologic cancers such as leukemia or lymphoma.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 4 is a schematic representation of Gal-1hFc in its reduced and non-reduced forms.

FIG. 5 is an image of a gel showing purified Gal-1hFc and its mutants were analyzed by SDS-PAGE and Western blotting with anti-human Fc or anti-mouse Gal-1.

| | |
|---|---|
| 337 | GlcNAcα1-4 Galβ 1-4GlcNAcβ 1-3Galβ 1-4(Fucα1-3)GlcNAc |
| 253 | NeuAcα2-3 Galβ -1-4Glcb |
| 351 | [6OSO3]GlcNAcβ1-3Galβ 1-4GlcNac-b-Sp0 |
| 413 | Fucα1-2Galβ 1-4(Fucα1-3) GlcNAcβ 1-3Galβ 1-4GlcNAc |
| 25 | [3OSO3] Galβ 1-4[6OSO3]Glcb-Sp8 |
| 350 | Galβ 1-3(Fucα1-4)GlcNAcb1-2Man α1-3 Galβ 1-3GlcNAc |
| 166 | GlcNAcβ1-2Galβ1-3GalNAca-Sp8 |
| 288 | 6-H2PO3Glcb-Sp10 |
| 230 | NeuAc α2-3Galβ 1-3(Fucα1-4)GlcNAcβ 1-3Galβ 1,4GlcNAc |
| 178 | GlcNAc β1-4 Galβ 1-4GlcNAcb-Sp8 |
| 42 | [6OSO3] Galβ 1-4[6OSO3]Glcb-Sp8 |
| 20 | [3OSO3]G alβ 1-4[6OSO3]GlcNAcb-Sp0 |
| 117 | Gal α1-6Glcb-Sp8 |
| 139 | Galβ 1-3GlcNAcβ 1-3Galβ 1-4Glcb-Sp10 |
| 31 | [3OSO3][6OSO3] Galβ 1-4[6OSO3]GlcNAcb-Sp0 |
| 165 | GlcNAc α1-6 Galβ 1-4GlcNAcb-Sp8 |
| 305 | HOOC(H3)CH-3-O-GlcNAc β1-4GlcNAcb-Sp10 |
| 286 | [3OSO3][4OSO3] Galβ 1-4GlcNAcb-Sp0 |
| 32 | [3OSO3] Galβ 1-4[6OSO3]GlcNAcb-Sp8 |
| 36 | [4OSO3][6OSO3] Galβ 1-4GlcNAcb-Sp0 |

Figure 7A:
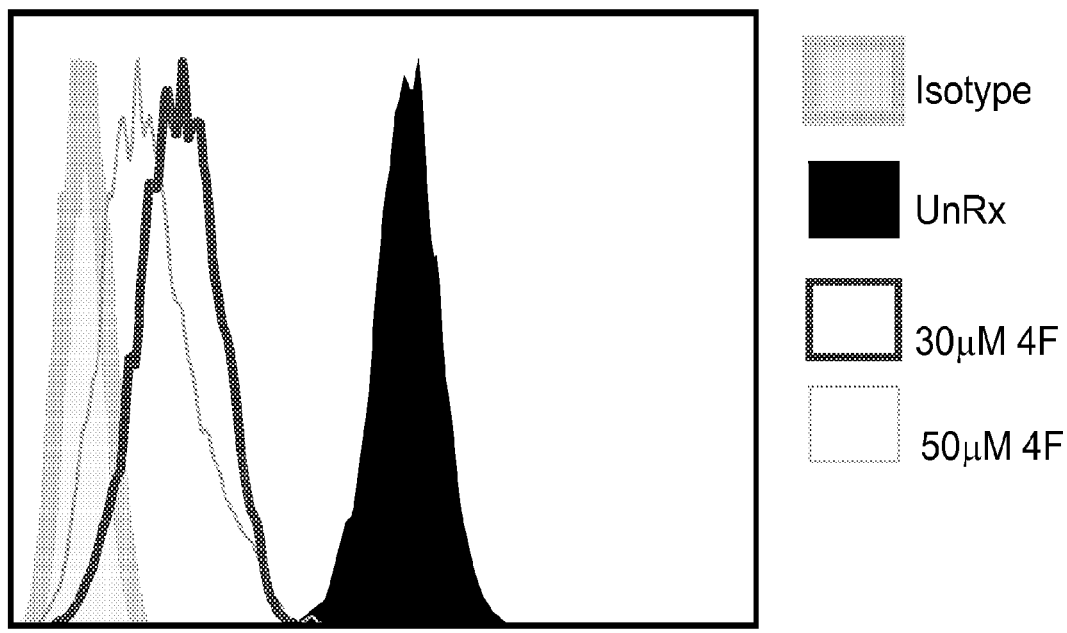
Figure 7B:
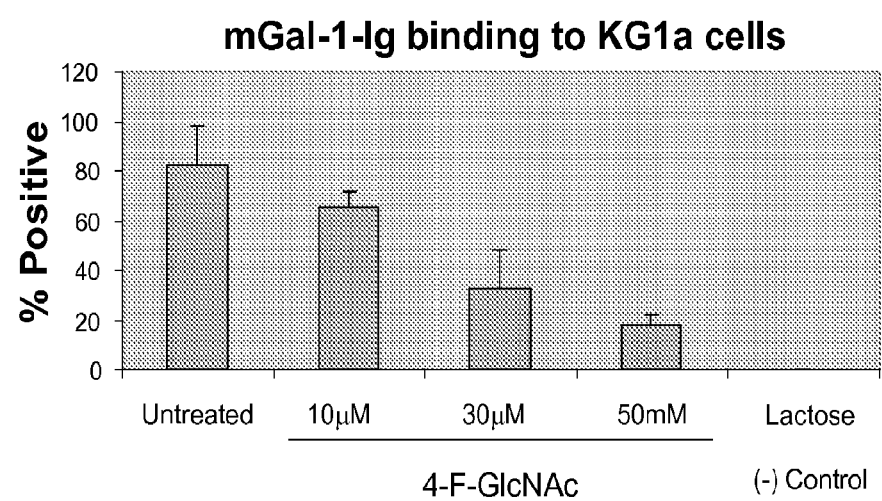

FIGS. 7A-7B show the results of analysis of Gal-1 ligand expression on human hematopoietic KG1a cells treated with 4-F-GlcNAc, a metabolic inhibitor of N-acetyllactosamine [Galβ1,4GlcNAc] formation. KG1a cells were treated for 48 hours with non-growth-inhibitory concentrations of 4-F-GlcNAc and analyzed by flow cytometry with Gal-Ig for the presence of Gal-1 ligands (7A). FIG. 7B is a bar graph showing a statistical representation of three independent experiments, demonstrating that increasing concentrations of 4-F-GlcNAc or of lactose reduce Gal-1 binding.

Figure 8A:
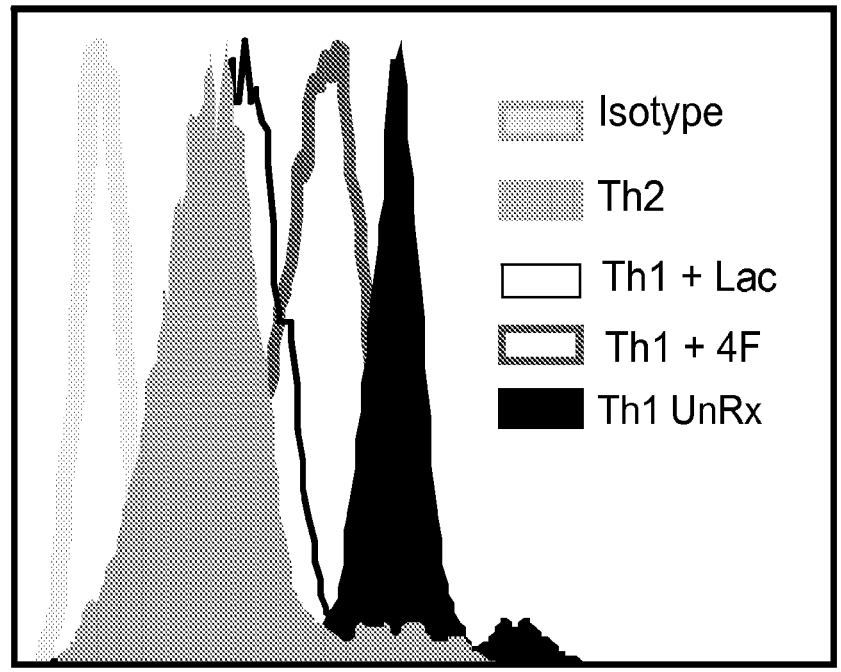
Figure 8B:
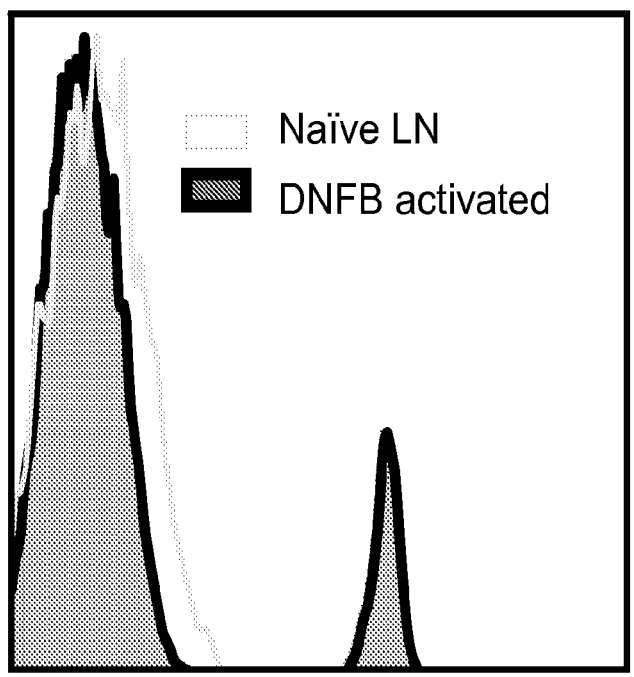

FIGS. 8A-8B are graphs showing the results of flow cytometric analysis of Gal-1 ligand expression on Th1 and Th2 cell subsets and on activated antigen-specific T cells. Flow cytometry was performed on ex vivo-polarized Th1 and Th2 cell subsets (8A) and on freshly-isolated activated antigen-specific T cells (8B) using Gal-Ig and APC-goat anti-hIg Ab. Th1 cells expressed the highest level of Gal-1 ligands, which were inhibited by 50 mM lactose co-incubation or diminished by metabolic treatment with 4-F-GlcNAc.

FIGS. 9A-9B are graphs showing the results of flow cytometric analysis of Gal-1 ligand expression on human prostate PC-3 tumor cells transfected with α1,3 fucosyltransferase VII or of Gal-1 ligand expression on Wehi-3 cells treated with a broadly-active neuraminidase (Neu). Flow cytometry was performed on prostate tumor PC-3 cells overexpressing FT7 (9A) and on WEHI-3 cells treated with neuraminidase for 1 hour at 37° C. (9B).

Figure 10B:
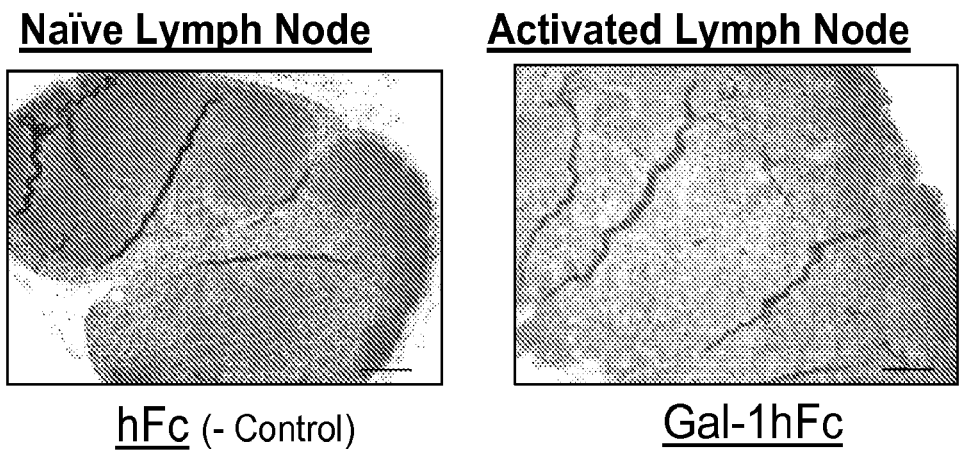

FIGS. 10A-B are photomicrographs showing detection of Gal-1 ligands on WEHI-3 Cells and in Jurkat cell lysates by immunohistochemistry and Western blotting. Sections of formalin-fixed paraffin-embedded Wehi-3 cells were analyzed for expression of Gal-1 ligands with Gal-Ig. Panel (10A) represents background staining with secondary Ab (anti-hIgG) alone, while Panel (10B) shows immunoreactivity of Gal-Ig and anti-hIg Ab. Insets show cells at 200× magnification.

Figure 11A:
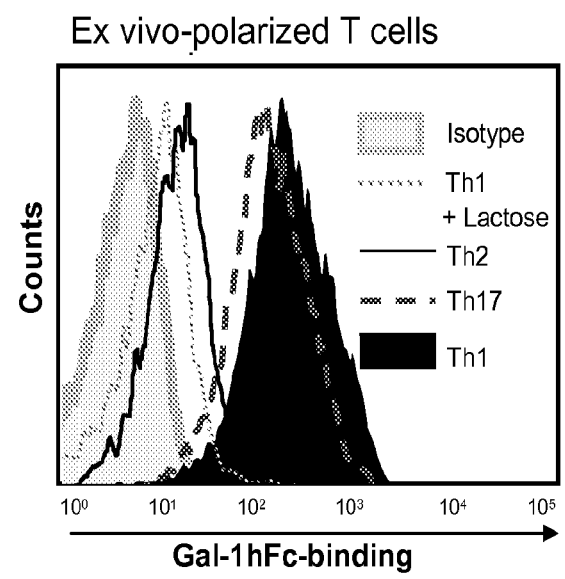
Figure 11B:
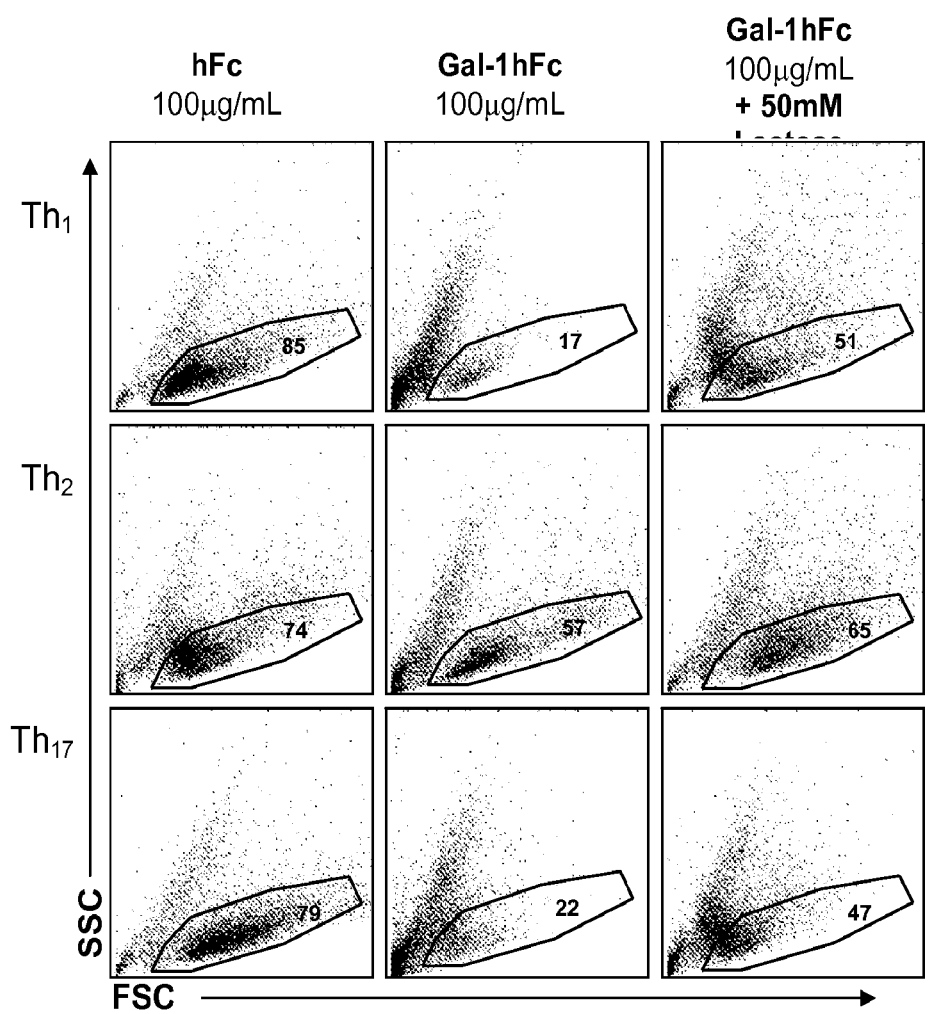
Figure 11C:
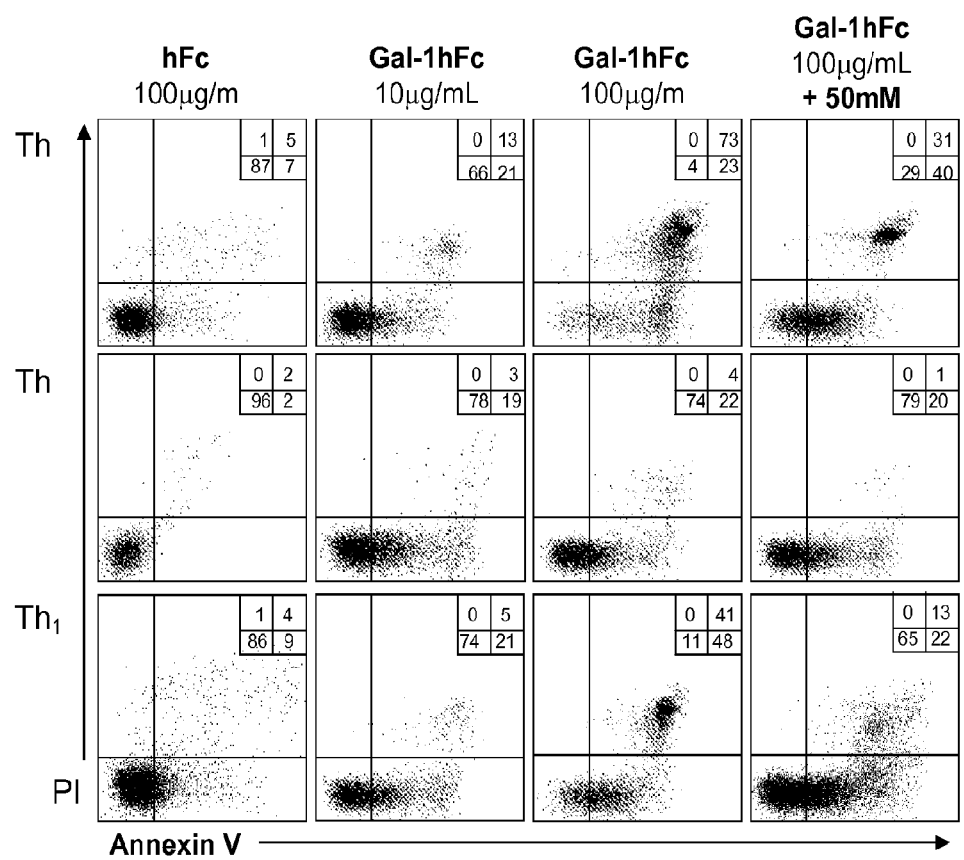

FIGS. 11A-C are graphs showing Gal-1hFc induces apoptosis in Th1 and Th17 cell subsets. (11A) Gal-1hFc-binding was assessed on mouse ex-vivo polarized Th cell subsets. (11B) Viability of Th1, Th2 and Th17 cell subsets treated with Gal-1hFc in the presence or absence of 50 mM lactose for 24 h was displayed in FSC/SSC dot plots. Alternatively, evidence of apoptosis on each Th subset was evaluated by Annexin V staining and PI uptake (11C). Histograms and dot plots are representative of at least 3 separate experiments.

Figure 12:
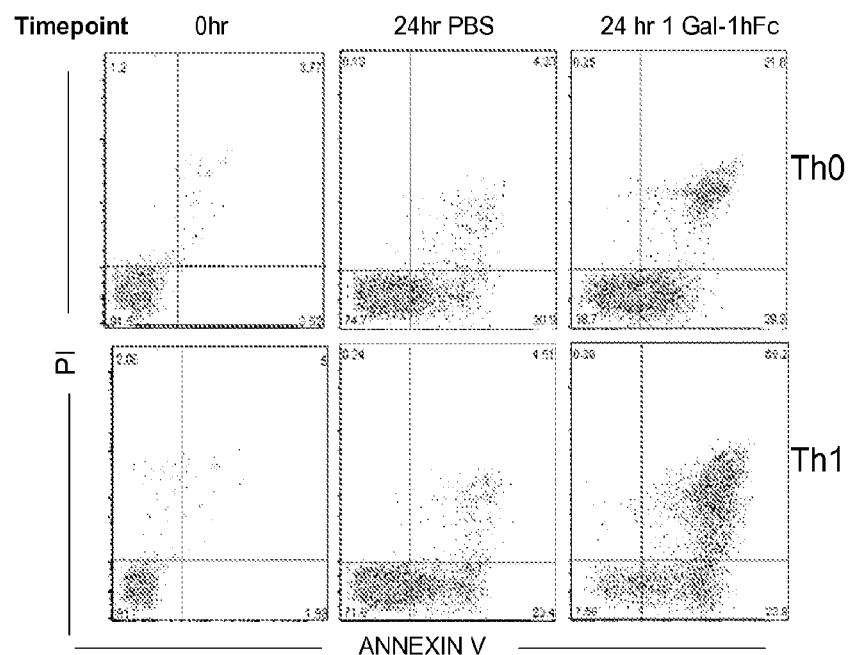

FIG. 12 is a set of six plots showing the results of flow cytometric analysis of phosphatidylserine and PI uptake on Th0 or Th1 Cells Pre-incubated with Gal-Ig. Ex vivo activated Th0 (top row) and Th1 (bottom row) cells were treated with 100 µg/ml Gal-Ig (right column) or vehicle (PBS) (middle column) and incubated for 24 hours. Cells were then stained with FITC-Annexin V and cell death marker, propidium iodide (PI) and analyzed by flow cytometry.

Figure 13:
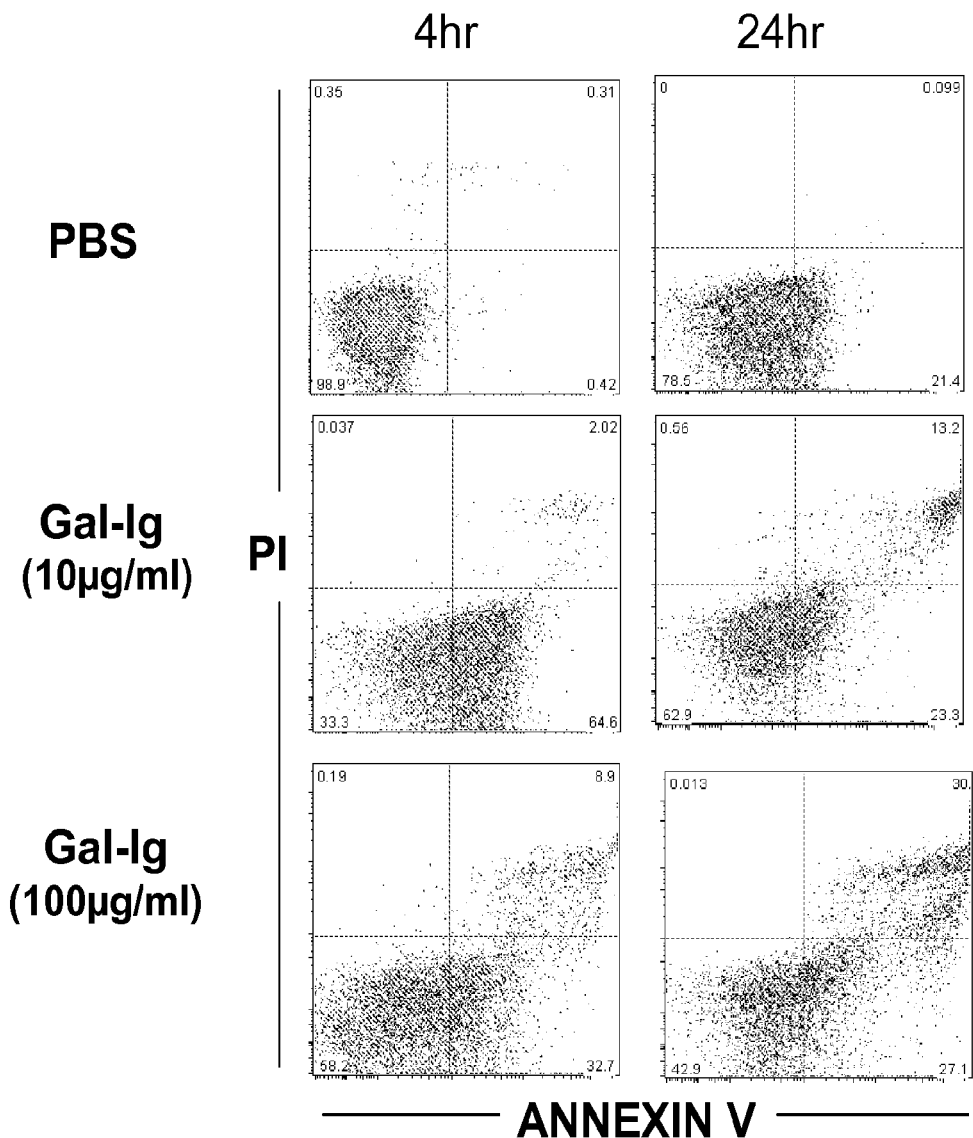

FIG. 13 is a set of six plots showing the results of flow cytometric analysis of Annexin V expression and PI uptake in the presence of Gal-Ig at concentrations of 10 mg/ml (middle row) or 100 mg/ml (bottom row) or vehicle (PBS, top row) after 4 (left column) or 24 (right column) hours. Gal-Ig induces apoptosis on human leukemic HL-60 cells.

Figure 14:
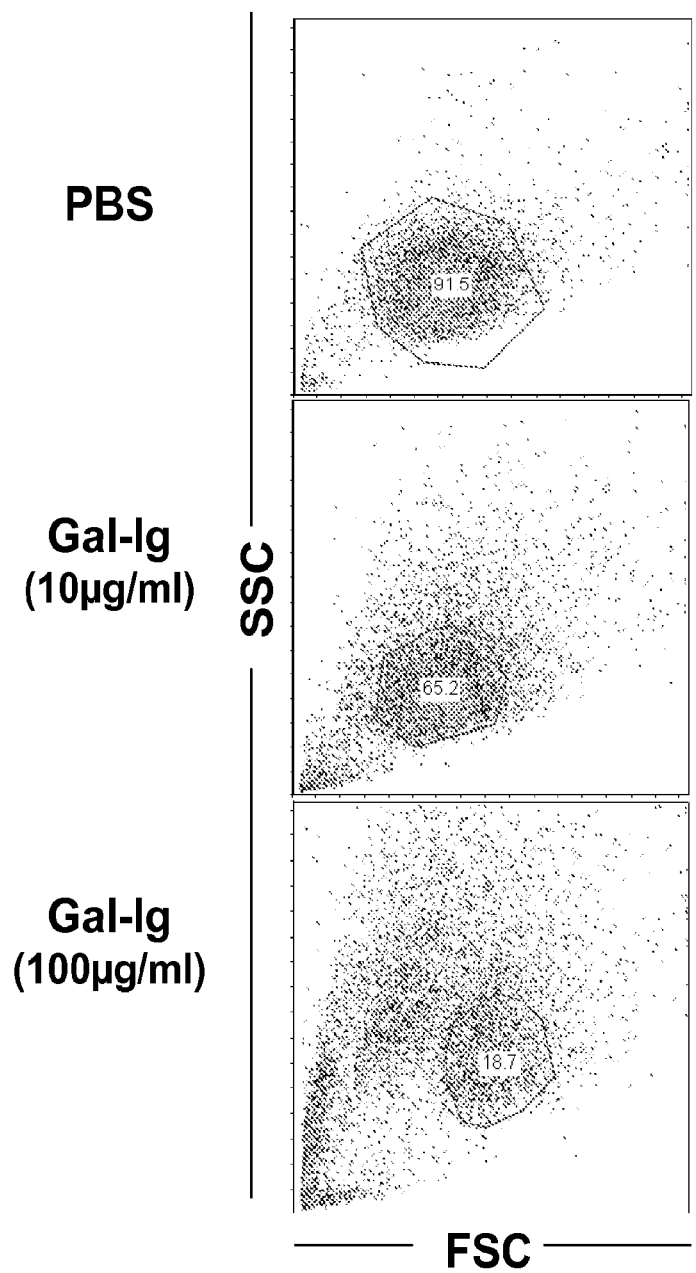

FIG. 14 is a set of three plots showing the results of forward and side scatter analysis of cells incubated for 24 hours in the presence of Gal-Ig at concentrations of 10 mg/ml (middle) or 100 mg/ml (bottom) or vehicle (PBS, top). The results reveal morphological changes suggestive of cell death.

Figure 15A:
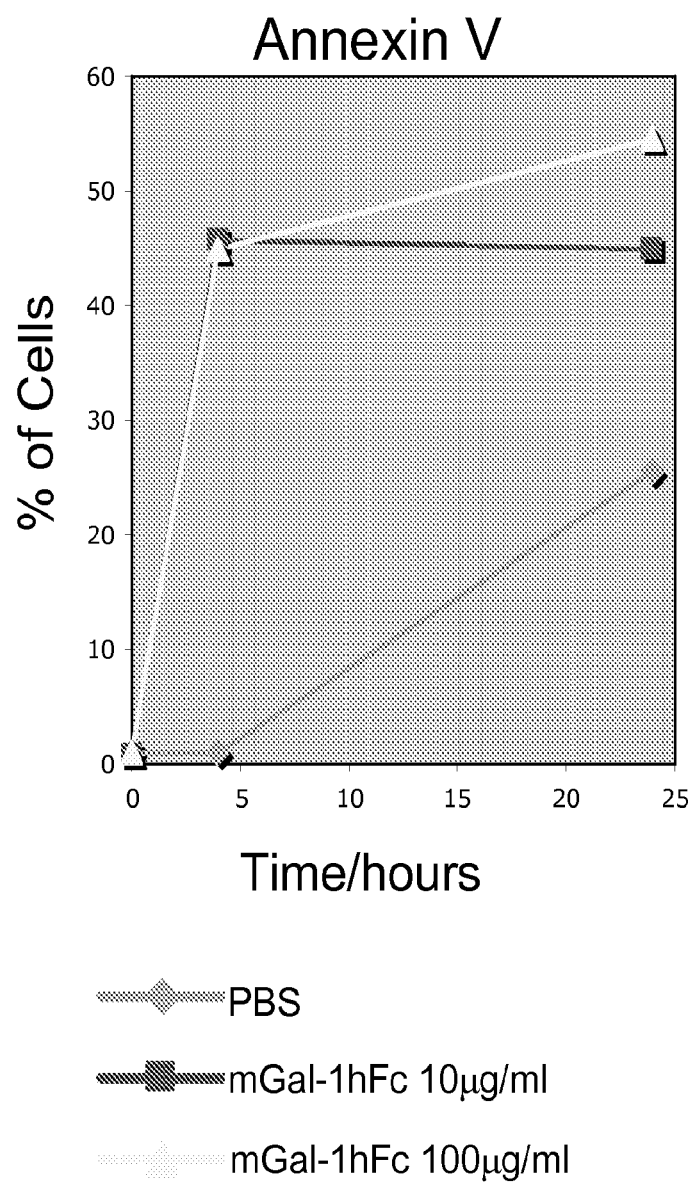
Figure 15B:
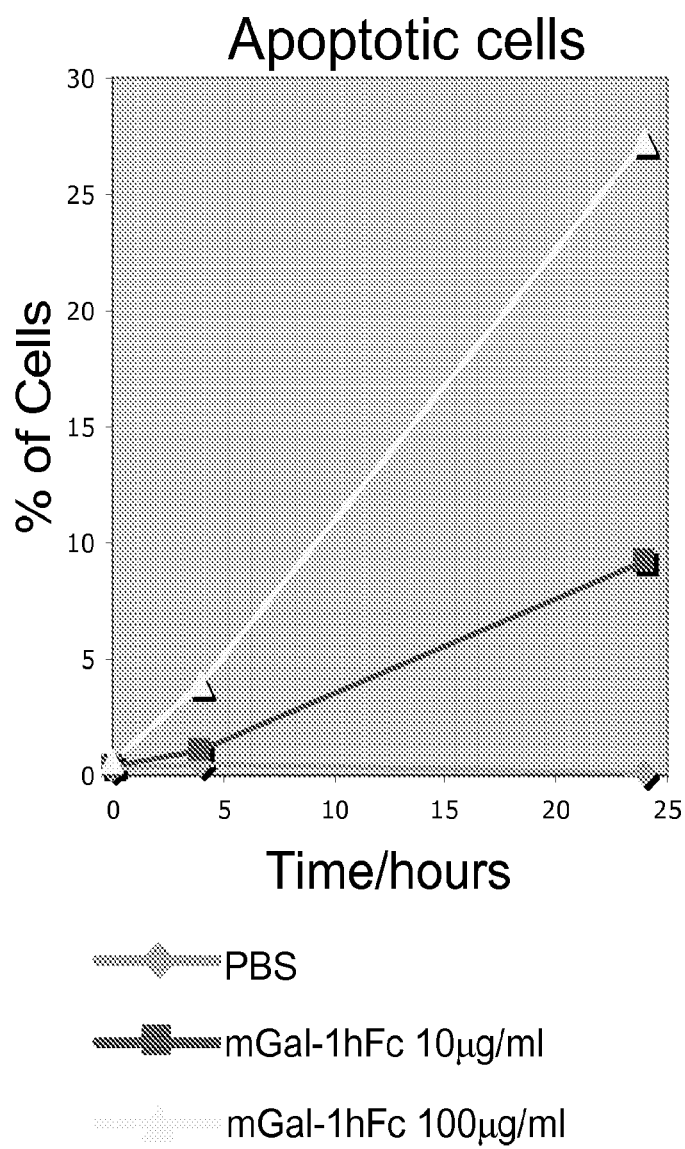

FIGS. 15A-B are line graphs showing that Gal-Ig induces pro-apoptotic changes at low concentrations and apoptosis at high concentrations of Gal-Ig in HL-60 cell cultures. HL-60 cells were incubated in the presence of Gal-Ig at concentrations of 10 µg/ml (squares) or 100 µg/ml (triangles) or vehicle (PBS, diamonds). Cells were analyzed by flow cytometry after 4 and 24 hours for pro-apoptotic changes (Annexin-V positivity) and for apoptosis (Annexin V and PI double positive cells). Experiment done by triplicate, where points show mean values.

Figure 16A:
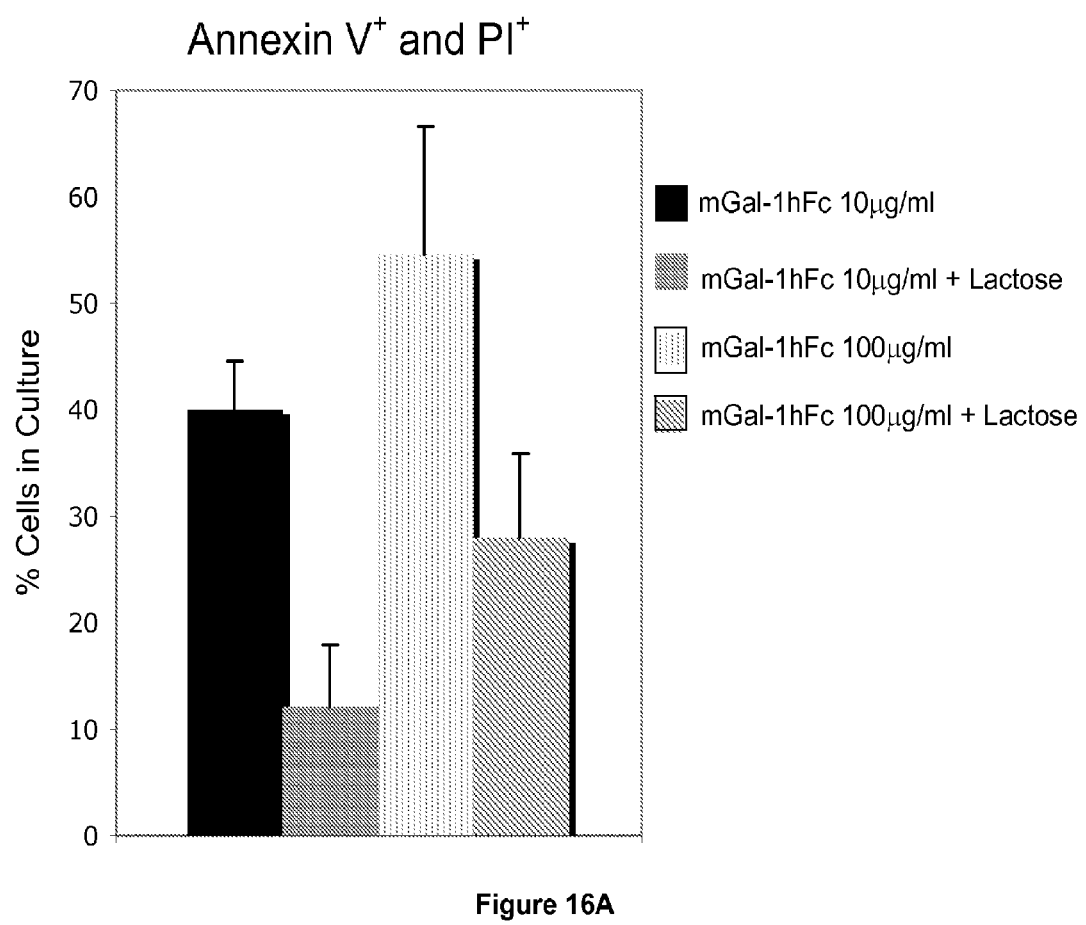

FIG. 16A is a bar graph showing that the Galectin-1-binding antagonist, lactose, protects human leukemic HL-60 cells treated with Gal-Ig from cell death.

Figure 16B:
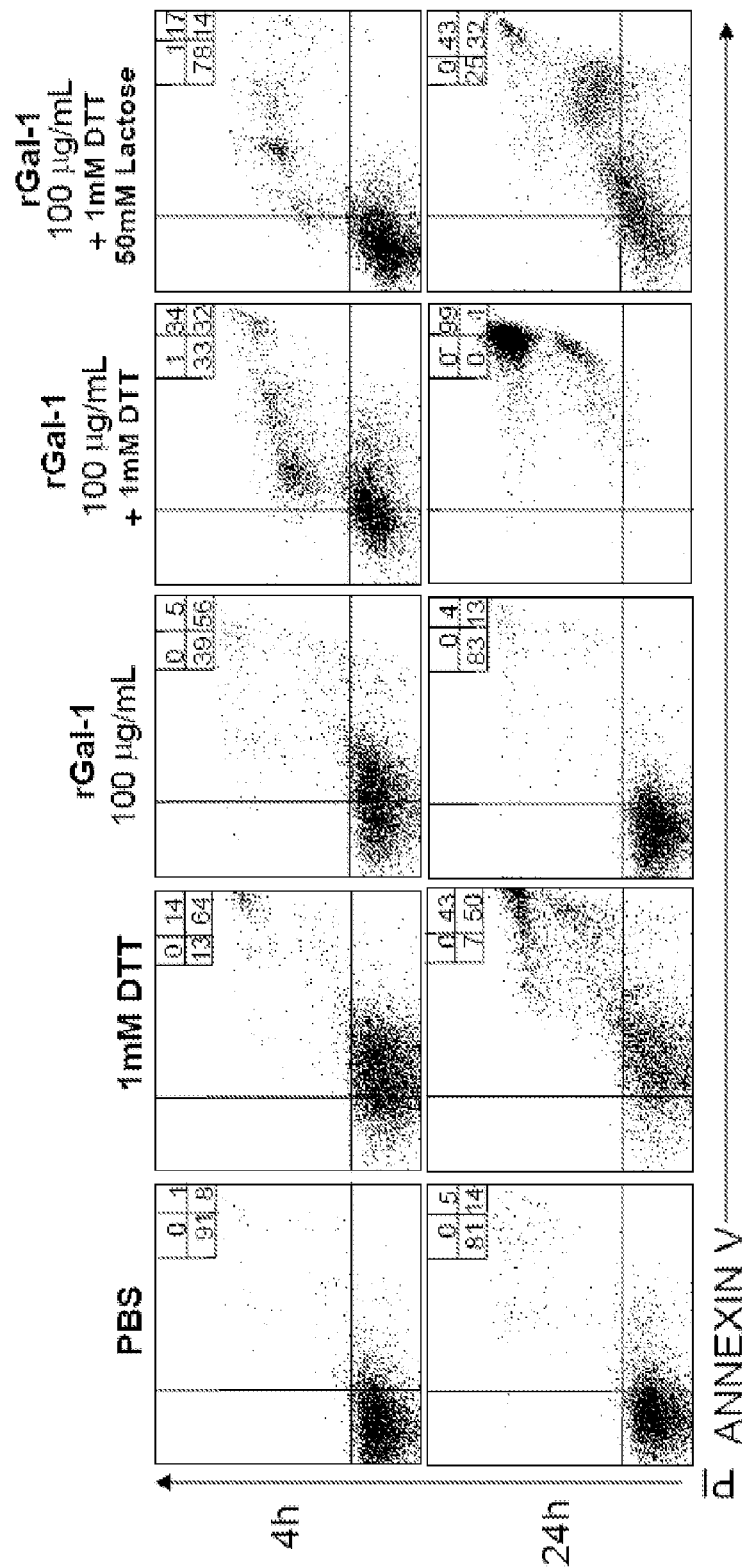

FIGS. 16B and C are dot plots showing the results of comparative analysis of apoptosis induction in pro-myeloleukemic HL-60 cells using rGal-1 and Gal-1hFc. (6A), HL-60 cells were incubated with rGal-1 in the presence or absence of DTT and/or 50 mM lactose. Cell death analysis (Annexin V staining/PI uptake) was evaluated by flow cytometry at 4 and 24 h post-incubation. (6B), HL-60 cells were incubated with Gal-1-hFc or mGal-1hFc in the presence or absence of 50 mM lactose. Cell death analysis (Annexin V staining/PI uptake) was evaluated by flow cytometry at 4 and 24 h post-incubation. Histograms or dot plots are representative from at least 3 separate experiments.

Figure 17A:
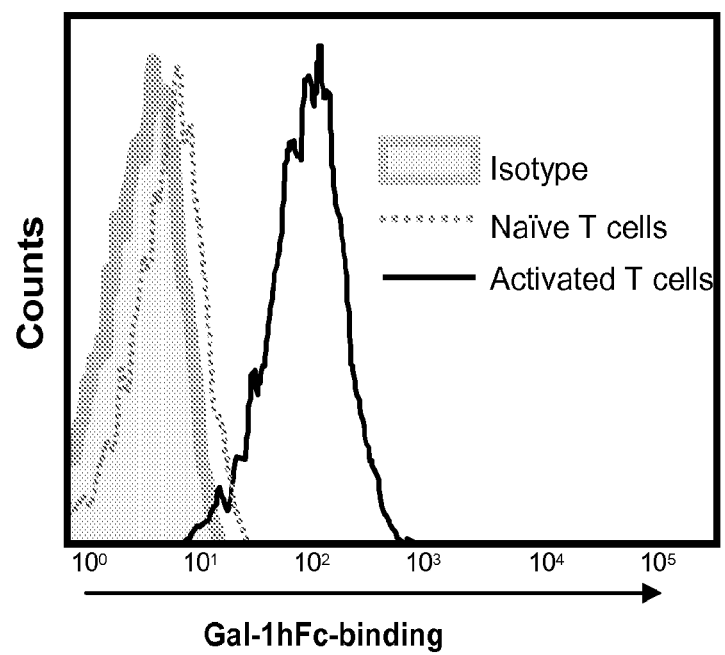

FIGS. 17A and B are Gal-1hFc stimulates the secretion of immunoregulatory molecules. (17A) Naïve CD4+ T cells were isolated by immunomagnetic beads from mouse spleens and activated for 72 h with anti-CD3/CD28. Gal-1hFc-binding was assayed on naïve and activated CD4+ T cells. (17B) Activated CD4+ T cells were then incubated for an additional 24 h with Gal-1hFc (+/−50 mM lactose), control hFc or mGal-1hFc. Supernatants were collected and analyzed for expression of 40 cytokines with a mouse cytokine panel array kit and quantified by optic densitometry, and mean densities were normalized to hFc-treated group. A graphical representation of data from a set of 3 separate experiments is shown as Mean Fold Difference. Statistically significant difference compared with lactose control, $*p \leq 0.01$.

Figure 18A:
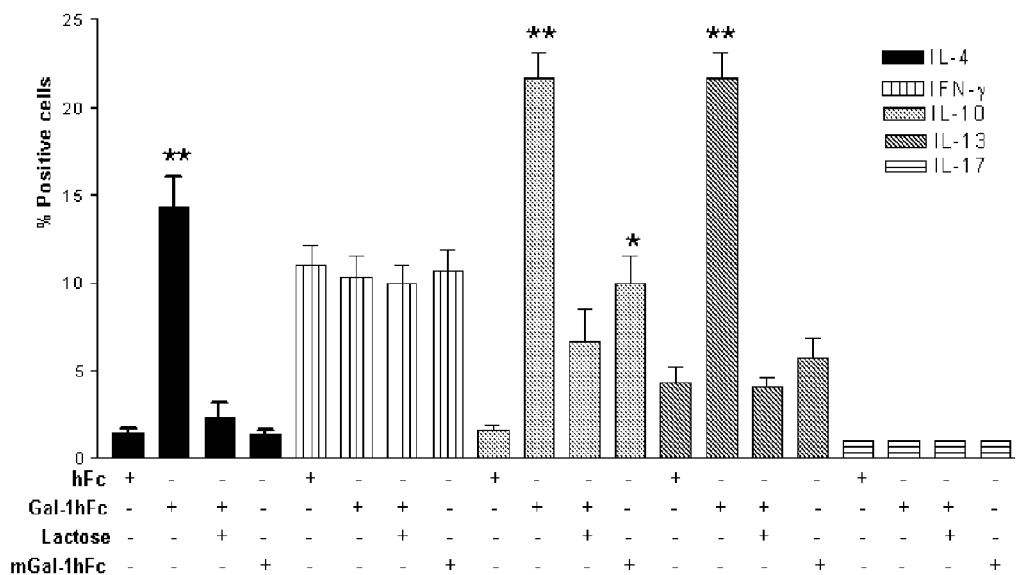
Figure 18B:
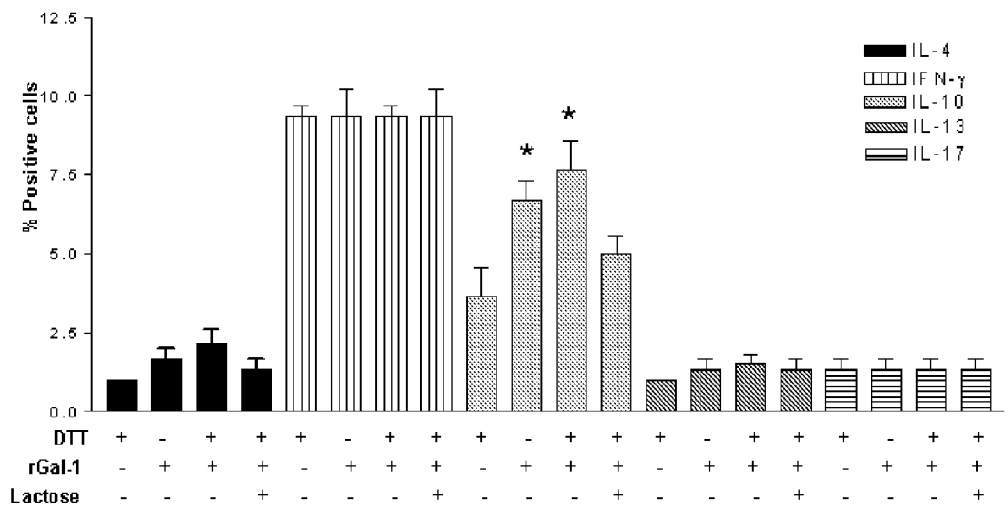
Figure 18C:
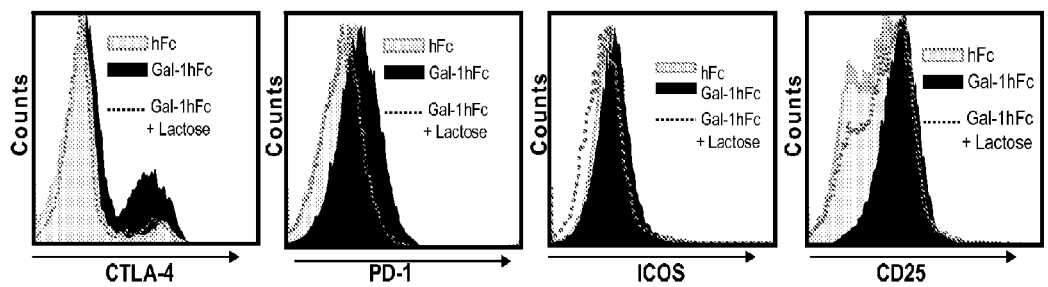

FIGS. 18A-C show that Gal-1hFc skews T cell differentiation. (18A), Naïve mouse CD4+ T cells were activated with anti-CD3/CD28 and incubated with Gal-1hFc (+/−50 mM lactose), control hFc or mGal-1hFc for 24 h, stained with antibodies against IL-4, IL-10, IL-13, IFN-γ and IL-17 and analyzed by flow cytometry. (18B), Activated CD4+ T cells were alternatively treated with rGal-1 and/or 1 mM DTT (+/−lactose) for 24 h and analyzed as above. Graphical representations of data sets from 3 separate experiments are shown. Statistical significant differences compared with hFc control, $*p \leq 0.05$, $p \leq 0.005$. (18C**) 48 h-activated mouse CD4+ T cells were incubated with Gal-1hFc (+/−50 mM lactose) for 24 h; stained with antibodies against CTLA4, PD-1, ICOS and CD25, and analyzed by flow cytometry.

Figure 19A:
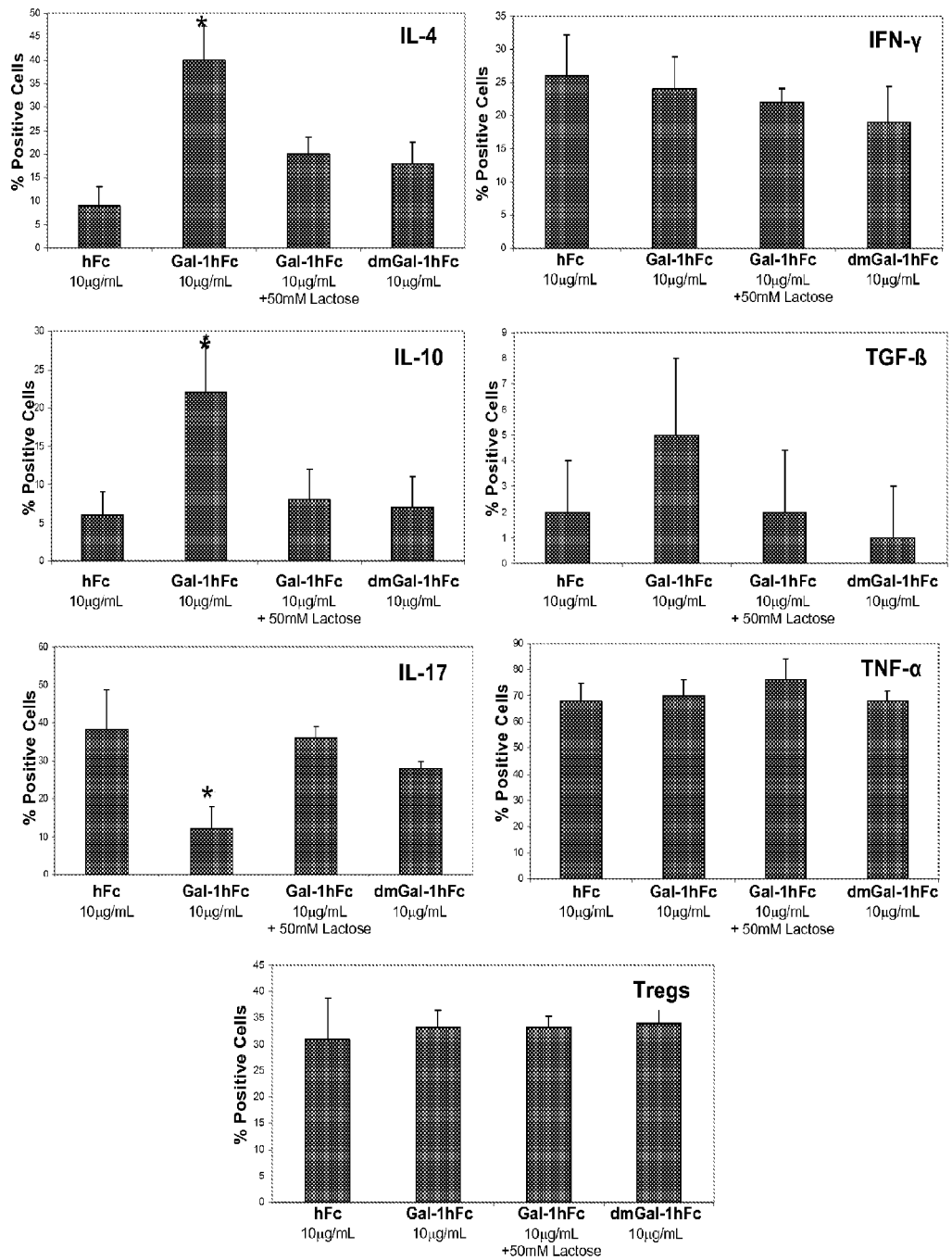

FIG. 19A is a set of seven bar graphs showing that Gal-1hFc modulates effector molecules in skin-resident human T cells. Human skin-resident effector memory T cells were incubated in the presence of Gal-1hFc or molecular controls for 24 h and stained with antibodies against CD25 and intracellular molecules FOXP3, IFN-γ, IL-4, IL-10, TGF-β, IL-17, and TNF-α and analyzed by flow cytometry. Analyzed T cells were first gated on CD3+ and CD8− cells. Graphical representations of data taken from 5 independent donors. Statistically significant difference compared with hFc control, $*p \leq 0.01$.

Figure 19B:
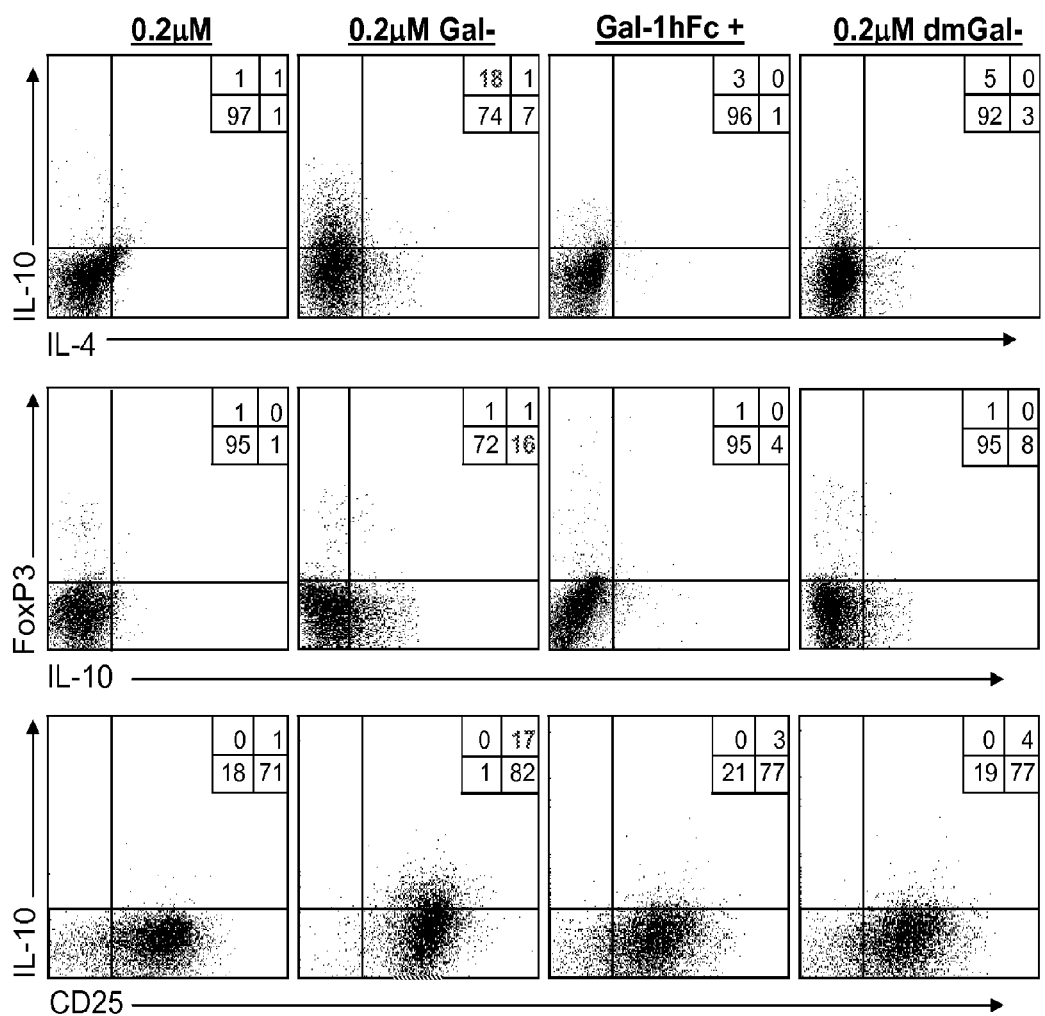

FIG. 19B is a set of twelve dot plots showing that Gal-1hFc-induced IL-10+ T cells express high levels of CD25 and do display Th2 and Treg cell phenotypes.

Figure 19C:
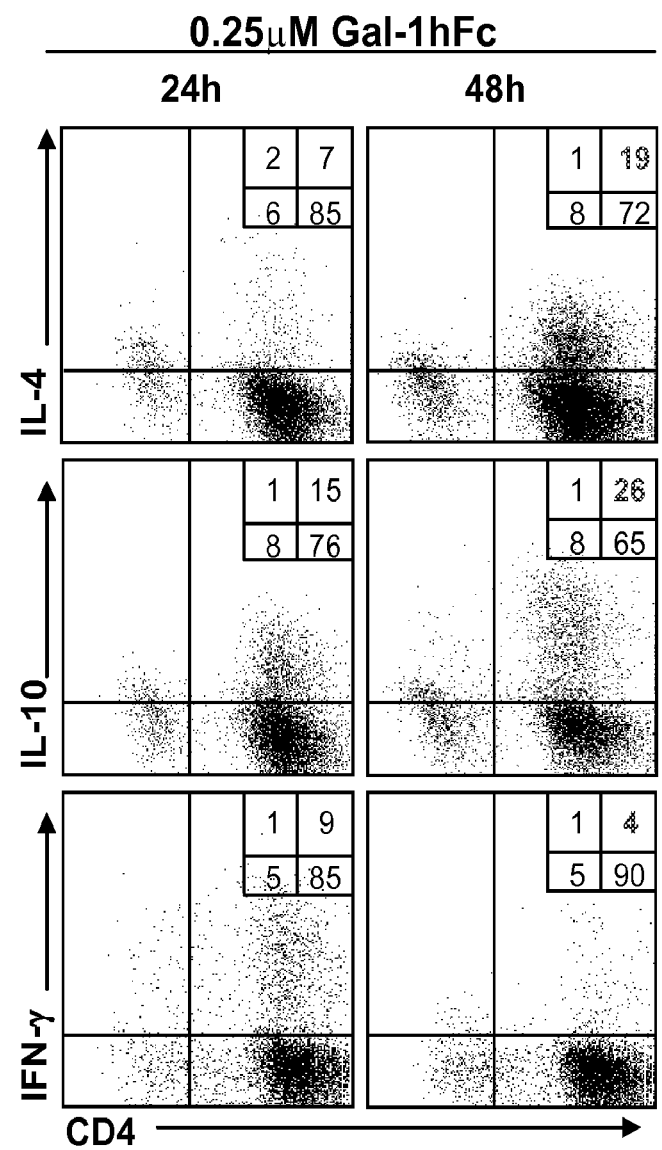

FIG. 19C is a set of six dot plots showing that Gal-1hFc promotes Th2 skewing and IL-10 production and inhibits IFN-g expression in mouse T cells activated ex vivo.

Figure 19D:
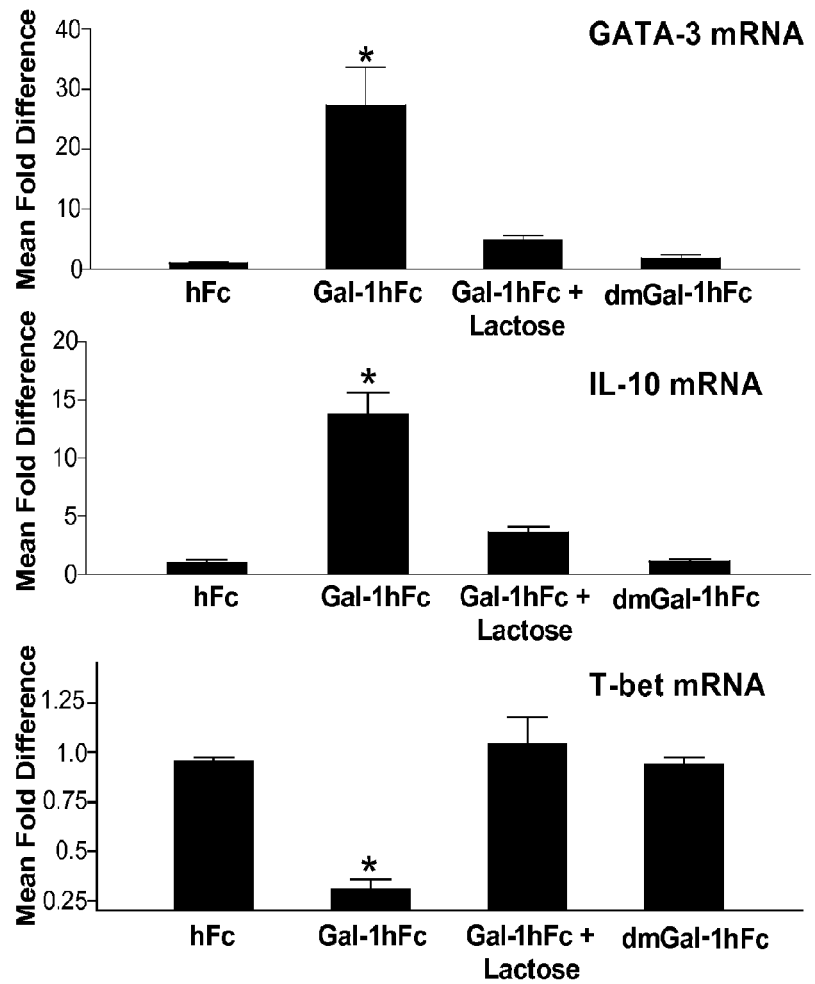

FIG. 19D is a set of three bar graphs showing levels of GATA-3, IL-10, and T-bet mRNA in naïve mouse T cells that were activated ex vivo and treated with Gal-1hFc or relevant controls as shown.

FIGS. 20A-E show that Gal-1hFc induces apoptosis of granulocytic infiltrates from synovial fluid of patients with rheumatoid arthritis (RA). (20A) Infiltrates of synovial fluids from patients with RA were analyzed by flow cytometry for the expression of CD19, CD15 and CD177. (20B) The same cells were stained with Gal-1hFc and anti-human CD15 antibodies (+/−50 mM lactose) and analyzed by flow cytometry. (20C) Data were graphed from a set of 4 independent donors. (20D) CD15+ cells from synovial fluid samples were incubated with 10 or 100 μg/ml Gal-1hFc (+/−lactose) Annexin V and PI positive cells were evaluated after 12 and 24 h post-incubation. (20E) Data were graphed from a set of 4 independent donors. Statistically significant difference compared with lactose controls, $*p \leq 0.01$.

FIGS. 21A-E show that Gal-1hFc2 modulates cytokine production in T cells draining antigen-sensitized skin and ameliorates antigen-dependent inflammation. On day 3 following DNFB sensitization, Gal-1 ligand expression on lymphocytes from LNs draining naïve and DNFB-sensitized skin was analyzed by flow cytometry with Gal-1hFc and anti-CD4 and CD69 mAbs (21A). Lactose (+lac) was added to incubation buffer to control for Gal-1 binding. On day 6 following oxazolone sensitization and challenge in mice treated with hFc (50 μg/22 g mouse) or Gal-1hFc2 (50 μg/22 g mouse), lymphocytes in LNs draining oxazolone-sensitized skin were enumerated (21B). Lymphocytes were then re-stimulated for 6 h with PMA/ionomycin/brefeldin A and analyzed for IL-4, IL-10, IL-17, IFN-γ, TGF-β, FOXP3 and CD25 expression by flow cytometry (21C). Ears from mice treated with either hFc or Gal-1hFc2 were fixed in 10% formalin and stained with hematoxylin and eosin (21D) and measured for change in thickness 24 h after vehicle alone- or oxazolone-challenge (21E). All experiments were repeated 3-times and consisted of 3 mice/per group. Statistically significant differences compared with hFc treatment controls, $*p \leq 0.01$.

FIG. 22 is an exemplary sequence of a Galectin-1-Ig fusion construct. The sequence of Galectin-1 (14.9 kDa) is shown in regular font, a linker having the sequence Arg-Ser (from Bgl II restriction digest) (0.3 kDa) is in a box, and the sequence of the Fc region containing CH2 and CH3 domains of the IgG heavy chain along with the hinge region (25.6 kDa) is in bold font.

DETAILED DESCRIPTION

The role of lectin-mediated control mechanisms in immunity has more recently been expanded to include a class of lectins called galectins.

Mammalian gene expression and recombinant protein technology have opened new directions in the development of innovative fusion proteins for use in diagnostic, therapeutic, and biochemical assaying methods. One useful fusion protein partner is the Fc (Ig) portion of immunoglobulin heavy chain (Walz et al., Science. 250(4984):1132-5 (1990)). When genetically-linked to a protein of interest, the resultant protein-of-interest-Ig fusion protein can dimerize and form a bivalent binding receptor. These fusion proteins have the ability to behave as a stable, high-affinity receptor that binds native ligands on cells (or in cell lysates), and as an anti-IgG Fc probe in immuno-detection assays, including Western blotting, flow cytometry, and immunohistochemistry. These new glycobiological probes have therapeutic application for biomedical research and clinical utility.

Galectin-1 (Gal-1) has not been extensively evaluated as a potential anti-inflammatory therapeutic in humans in part due to its inherent destabilizing properties, which ultimately affect its structure and thus its glycan-binding function and pro-apoptotic activity. Most studies using bacterial recombinant Gal-1 require the addition of reducing agents, e.g., DTT or β-mercaptoethanol, in assay media to prevent galectin-1 oxidation, destabilization and loss of function. Described herein is a Gal-Ig construct that, unlike the commercially-available bacterial recombinant mouse and human versions of Gal-1 (e.g., from R&D Systems, Inc.), retains all of the native traits of Gal-1 ligand-binding function, while maintaining long-term stability and pro-apoptotic-inducing activity without the use of reducing agents or other alkylation, structure stabilizing approaches. This Gal-1-IG construct is suitable for performance of preclinical glycobiologic, apoptotic and anti-inflammatory studies or of anti-inflammatory trials in humans.

The Gal-Ig fusion constructs described herein have a number of advantages, including at least the following: (1) stable multimeric forms of Gal-Ig can be produced in large quantities and efficiently isolated, e.g., using the transfectant mammalian hematopoietic J558L cell line; (2) Gal-Ig preparations do not require the addition of reducing agents to help stabilize and maintain Gal-1 ligand-binding and pro-apoptotic activity of Gal-Ig; (3) Gal-Ig can be used as a Gal-1 ligand probe in flow cytometry, cell binding, Western blotting or immunohistochemistry assays: (4) Gal-1 ligand binding properties of Gal-Ig follow the same biochemical binding characteristics as native Gal-1; (5) Gal-Ig can be used as a probe to ascertain whether 4-F-GlcNAc treatment diminishes Gal-1 ligand expression on T cell line models and on native T cells; (6) Gal-Ig-binding induces phosphatidyl serine (PS) exposure and PI uptake, while PS exposure is reversed after the inclusion of lactose; and (7) Gal-Ig-binding causes apoptosis in activated Th cells incubated without the addition of any reducing or alkylating agent.

Unlike other previously described recombinant forms of Gal-1, including a human Gal-1 linked to a mutant form of human IgG1 Fc1 chimeric molecule (Tsai et al., J. Immunol. 2008 Oct. 1; 181(7):4570-9 (2008)), the Gal-Ig constructs described herein are effective in the absence of exogenous reducing agents or structure stabilizing approaches in the context of Gal-1 ligand interactions. The Gal-Ig constructs described herein are useful, e.g., as probes in glycobiology studies as well as in clinical applications, e.g., for induction of apoptosis in inflammatory T cells and to help ameliorate cellular mediators in a variety of inflammatory disorders, including autoimmune disorders.

Galectins

Galectins belong to a novel family of carbohydrate binding proteins with affinity for β-galactosides (G. A. Rabinovich, F. T. Liu, M. Hirashima et al., Scand J Immunol 66 (2-3), 143 (2007)). To date, the galectin family includes 15 members, divided in 3 different groups according to the number of carbohydrate recognition domains. Most of them exist in monomeric and non-covalent multimeric forms, secreted by a non-classical pathway that resembles the $Na^+/K^+$-ATPase pump (R. C. Hughes, Biochimie 83 (7), 667 (2001); W. Nickel, Traffic 6 (8), 607 (2005)). Galectin-1 (Gal-1, galaptin, LGALS1 lectin) was the first to be described and has been widely studied in the context of both adaptive and innate immune activities (S. H. Barondes, V. Castronovo, D. N. Cooper et al., Cell 76 (4), 597 (1994)). Gal-1 in its monomeric form is a 14.3 kDa protein, encoded by the LSGALS1 gene located on chromosome 22q12. The full-length gene product is comprised of the splicing of four exons and encodes a 135 amino acid protein with a single carbohydrate recognition domain (CRD) specific for binding to glycoconjugates bearing N-acetyllactosamine (LacNAc) Type 1 (Galβ1,3GlcNAc) or Type 2 (Galβ1-4GlcNAc) disaccharides, with increased avidity for poly-LacNAc chains (FIG. 1) (F. P. Schwarz, H. Ahmed, M. A. Bianchet et al., Biochemistry 37 (17), 5867 (1998)).

Figure 1:
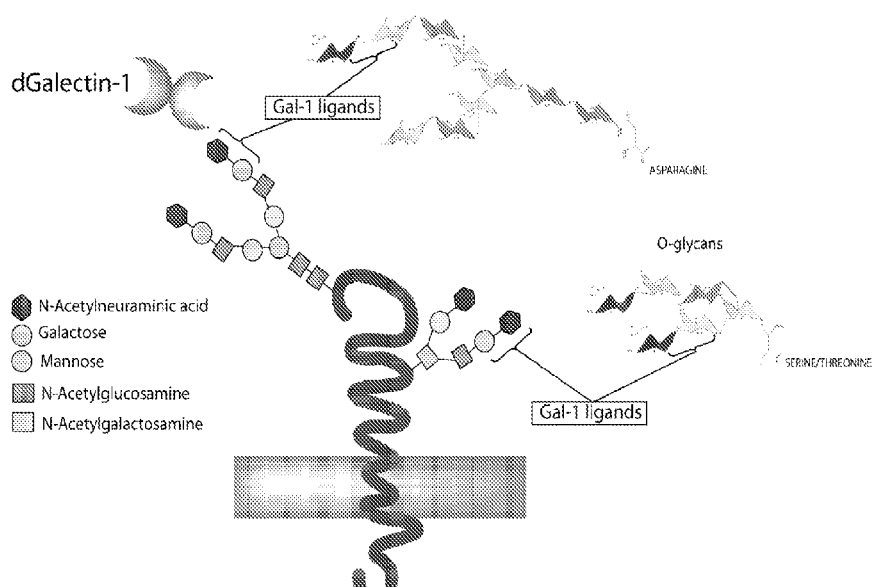
FIG. 1 is a schematic illustration of Galectin-1-Galectin-1 Ligand Interactions. Galectin-1 (Gal-1) in its native dimeric form binds Galβ1,4GlcNAc or Galβ1,3GlcNAc disaccharides on both O-and-N-glycans. Gal-1 binds a number of glycoproteins found on the cell surface of tumor cells and leukocytes.

Human Gal-1 exists as a homodimer in solution (M. F. Lopez-Lucendo, D. Solis, S. Andre et al., J Mol Biol 343 (4), 957 (2004)). The stability of this dimer (dGal-1) is maintained by interactions between the monomers at the interface and through the well-conserved phobic core. However, when concentrations drop below 7 µM, dGal-1 spontaneously dissociates into monomeric elements that are still able to bind carbohydrates, but with a significantly lower affinity (M. Cho and R. D. Cummings, J Biol Chem 270 (10), 5198 (1995); A. Leppanen, S. Stowell, O. Blixt et al., J Biol Chem 280 (7), 5549 (2005)). Gal-1, similar with many other lectins, mediate binding interactions through carbohydrate moieties on glycoconjugates on other cells or extracellular matrices (FIG. 1).

In the cell, Gal-1 regulates cell growth via activation/inhibition of the Ras-MEK-ERK pathway (C. Fischer, H. Sanchez-Ruderisch, M. Welzel et al., J Biol Chem 280 (44), 37266 (2005); J. Kopitz, S. Andre, C. von Reitzenstein et al., Oncogene 22 (40), 6277 (2003)), and it also increases cell motility by reorganizing the cytoskeleton via induction of RhoA expression (N. Tinari, I. Kuwabara, M. E. Huflejt et al., Int J Cancer 91 (2), 167 (2001); S. Harvey, Y. Zhang, F. Landry et al., Physiol Genomics 5 (3), 129 (2001)). Out of the cell, Gal-1 lines the surfaces of epithelial, stromal and hematopoietic cells and is a component of basement membranes and extracellular matrices, where it binds to proteoglycans to help mediate cell adhesion, migration and growth-regulatory activities (J. He and L. G. Baum, J Biol Chem 279 (6), 4705 (2004)). Among well-characterized carbohydrate ligands, Gal-1 interacts with various leukocyte surface molecules, such as $β_1$ integrins, CD45, CD43, CD7, CD4, CD2 and CD3, through van der Waals forces and hydrogen bond formation in the carbohydrate recognition domain (K. E. Pace, C. Lee, P. L. Stewart et al., J Immunol 163 (7), 3801 (1999); H. Walzel, M. Blach, J. Hirabayashi et al., Glycobiology 10 (2), 131 (2000); N. L. Perillo, K. E. Pace, J. J. Seilhamer et al., Nature 378 (6558), 736 (1995); E. P. Moiseeva, B. Williams, A. H. Goodall et al., Biochem Biophys Res Commun 310 (3), 1010 (2003); O. Avni, Z. Pur, E. Yefenof et al., J Immunol 160 (12), 6151 (1998)).

Figure 2:
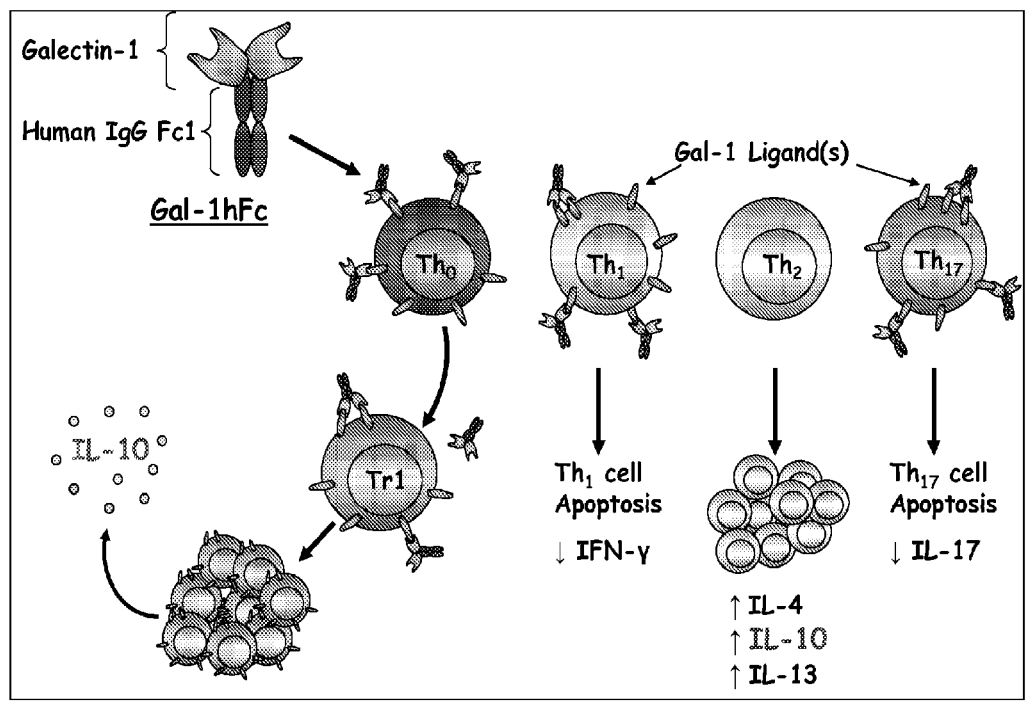
FIG. 2 is a schematic representation of Gal-1 effects on T cell differentiation. Gal-1 induces apoptosis of effector T cell subsets, Th1 and Th17, which are involved in inflammation, while facilitating the expansion of T regulatory cells, which help dampen Th1 and Th17 cell functions and promote immune suppression.

Gal-1 has a number of regulatory activities on the function of effector T cells. It has been shown that Gal-1 intervenes in the T cell maturation process in the thymus (N. L. Perillo, C. H. Uittenbogaart, J. T. Nguyen et al., J Exp Med 185 (10), 1851 (1997)), the preservation of fetomaternal tolerance (S. M. Blois, J. M. Ilarregui, M. Tometten et al., Nat Med 13 (12), 1450 (2007)), and the establishment of cancer "immune privilege" sites (E. P. Moiseeva, E. L. Spring, J. H. Baron et al., J Vasc Res 36 (1), 47 (1999); N. Clausse, F. van den Brule, D. Waltregny et al., Angiogenesis 3 (4), 317 (1999)). Immunoregulatory effects of Gal-1 include the downregulation of pro-inflammatory cytokines IFN-γ and IL-17 (M. A. Toscano, G. A. Bianco, J. M. Ilarregui et al., Nat Immunol 8 (8), 825 (2007)) and skewing T cell development towards a Th2 cytokine profile (C. C. Motran, K. M. Molinder, S. D. Liu et al., Eur J Immunol 38 (11), 3015 (2008)). Moreover, Gal-1 increases IL-10 production via stimulation of TR-1 cells (S. M. Blois, J. M. Ilarregui, M. Tometten et al., Nat Med 13 (12), 1450 (2007)), and it also induces expansion of $CD4^+CD25^+$ $FOXP3^+$ regulatory T cells (M. A. Toscano, A. G. Commodaro, J. M. Ilarregui et al., J Immunol 176 (10), 6323 (2006)) (FIG. 2). Furthermore, Gal-1 induces apoptosis on $Th_1$ and $Th_{17}$ cells, a paradigm that has recently been challenged.

Data supporting the pro-apoptotic theory indicates that Gal-1-binding generates the formation of CD45/CD43/CD7 membrane microdomains that triggers the activation of the transcription factor AP-1, of caspases and cytochrome C-associated death pathways, and increased sensitization to FasL-mediated cell death (G. A. Rabinovich, F. T. Liu, M. Hirashima et al., Scand J Immunol 66 (2-3), 143 (2007); P. Matarrese, A. Tinari, E. Mormone et al., J Biol Chem 280 (8), 6969 (2005)). Additionally, evidence indicates that a caspase-independent apoptotic pathway involving rapid nuclear translocation of endonuclease G from the mitochondria due to Gal-1 ligand binding (H. P. Hahn, M. Pang, J. He et al., Cell Death Differ 11 (12), 1277 (2004)). To the contrary, an alternative view shows that Gal-1 can induce reversible externalization of phosphatydilserine (PS) to the outer membrane evidenced by Annexin V staining, but does not trigger morphological changes in the mitochondria or the nucleus (S. R. Stowell, Y. Qian, S. Karmakar et al., J Immunol 180 (5), 3091 (2008)). The contrasting difference between these death-inducing data is likely due to the method of cell death assays, in which most laboratories use dithiothreitol (DTT) to prevent oxidative inactivation and stabilize Gal-1. DTT blocks the formation of intra and extracellular disulfide bonds within Gal-1. However, the use of this reducing agent itself significantly sensitizes activated T cells to undergo apoptosis. This effect was not noted when Gal-1 preparations were artificially polymerized with alkylating agents, such as iodoacetamide (S. R. Stowell, S. Karmakar, C. M. Arthur et al., Mol Biol Cell (2008)). Furthermore, the immunological effects of Gal-1 in vivo have not been fully understood, due to the lack of a phenotype in the Gal-1 null mouse, suggesting redundancy in function among members of the galectin family. Additionally, this protein is highly susceptible to oxidative inactivation, limiting its effects and necessity of reducing agents to stabilize Gal-1 preparations.

In some embodiments, the Galectin-1 comprises the mouse Galectin-1, the sequence of which is available in GenBank under Accession No. NM_008495.2 (nucleic acid; nucleotides 11-132 are the coding region) and NP_032521.1 (amino acid). In some embodiments, the sequence of Gal-1 is or comprises SEQ ID NO: 1:

```
                                                 (SEQ ID NO: 1)
MACGLVASNLNLKPGECLKVRGEVAS-
DAKSFVLNLGKDSNNLCLHFNPRFNA

HGDANTIVCNTKEDGTWGTEHREPAF-
PFQPGSITEVCITFDQADLTIKLPDG

HEFKFPNRLNMEAINYMAADGDFKIKCVAFE
```

Although in some embodiments, the Galectin-1 used is a mouse Galectin-1, the Galectin-1 can also be human; the sequence of the human Gal-1 is available in GenBank under Accession Nos. NM_002305.3 (nucleic acid; nucleotides 11-132 are the coding region) and NP_002296.1 (amino acid). In some embodiments, the sequence of Gal-1 is or comprises SEQ ID NO:2:

```
                                                 (SEQ ID NO: 2)
MACGLVASNLNLKPGECLRVRGEVAP-
DAKSFVLNLGKDSNNLCLHFNPRFNA

HGDANTIVCNSKDGGAWGTEQREAVF-
PFQPGSVAEVCITFDQANLTVKLPDG

YEFKFPNRLNLEAINYMAADGDFKIKCVAFD
```

In some embodiments, a variant of the mouse Gal-1 can be created to enhance or reduce (inhibit) any antigenicity experienced, so long as the variant retains the activity of the Gal-1-Ig fusion construct described herein, i.e., the same glycan binding profile (i.e., the same ability to bind or not bind to specific glycans) as the mGal-Ig fusion protein described herein, e.g., to mutated mouse Gal-1-Ig, which exhibits diminished binding to Gal-1 ligands and induction of apoptosis in T cells.

The following is an alignment of the mouse (top row) and human (bottom row) Gal-1 sequences. The middle row is a consensus sequence; bold type indicates differences. Variants useful in the present constructs can include sequences with variations at the positions indicated. In some embodiments, the variant comprises the mouse sequence with mutations at residues outside of the sugar binding pocket, e.g., not mutated at amino acids 45, 47, 49, 60, 62, 69, 72, or 74, or not mutated in any of the amino acids from 45-74. In some embodiments, the variant only has conservative mutations at amino acids 45, 47, 49, 60, 62, 69, 72, or 74, or in any of the amino acids from 45-74. In some embodiments, the variant has one or more, two or more, three or more, four or more, five or more, six or more, seven or more, eight or more, nine or more, or ten or more mutations, e.g., conservative mutations or mutations that make the residue the same as in a sequence from another species, e.g., a mutation in the mouse sequence that replaces an amino acid with the corresponding amino acid in the human sequence, or vice verse. In some embodiments, the Gal-1 is a human Gal-1 with the sugar-binding sequence from the mouse Gal-1, e.g., mutations made at amino acids 45, 47, 49, 60, 62, 69, 72, or 74, to the mouse sequence, or the amino acids from 45-74. As an example, Tsai et al., J. Immunol. 2008 Oct. 1; 181(7):4570-9 (2008), described a mutated human Gal-1-Ig in which a tryptophan at position 69 is replaced with a glycine and thus did not bind Gal-1 ligands.

```
ALIGNMENT OF mGAL-1 AND hGAL-1
MACGLVASNLNLKPGECLRVRGEVAPDAKSFVLNLGKDSNNLCLHFNPRFNAHGDANTIV      60
MACGLVASNLNLKPGECL+VRGEVA DAKSFVLNLGKDSNNLCLHFNPRFNAHGDANTIV
MACGLVASNLNLKPGECLKVRGEVASDAKSFVLNLGKDSNNLCLHFNPRFNAHGDANTIV      60

CNSKDGGAWGTEQREAVFPFQPGSVAEVCITFDQANLTVKLPDGYEFKFPNRLNLEAINY     120
CN+K+ G WGTE RE  FPFQPGS+ EVCITFDQA+LT+KLPDG+EFKFPNRLN+EAINY
CNTKEDGTWGTEHREPAFPFQPGSITEVCITFDQADLTIKLPDGHEFKFPNRLNMEAINY     120

MAADGDFKIKCVAFD  (mouse, SEQ ID NO: 1)                           135
MAADGDFKIKCVAF+  (consensus, SEQ ID NO: 3)
MAADGDFKIKCVAFE  (human, SEQ ID NO: 2)                           135
```

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a Gal-1 variant protein is preferably replaced with another amino acid residue from the same side chain family. Following mutagenesis, the encoded protein can be expressed recombinantly and the activity of the protein can be determined using methods described herein or known in the art.

In some embodiments, the variant is at least about 90%, 95%, 99%, or 100% identical to a reference Gal-1 sequence described herein, e.g., SEQ ID NO: 1 (mouse) or 2 (human).

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can determined using the Needleman and Wunsch ((1970) J. Mol. Biol. 48:444-453) algorithm which has been incorporated into the GAP program in the GCG software package (available on the world wide web at gcg.com), using the default parameters, e.g., a Blossum 62 scoring matrix with a gap penalty of 12, a gap extend penalty of 4, and a frameshift gap penalty of 5.

Although the above discussion focused on Gal-1, other galectins can also be used, e.g., as shown in Table 1.

TABLE 1

Mammalian Galectins

| Gene Name | Species | GenBank Id. |
|---|---|---|
| LGALS2 | Homo Sapiens | NM_006498.2 |
|  | Mus Musculus | NM_025622.3 |
| LGALS3 | Homo Sapiens | NM_002306.3 |
|  | Mus Musculus | NM_001145953.1 |
| LGALS4 | Homo Sapiens | NM_006149.3 |
|  | Mus Musculus | NM_010706.1 |
| Lgals6 | Mus Musculus | NM_010707.2 |
| LGALS7 | Homo Sapiens | NM_002307.3 |
|  | Mus Musculus | NM_008496.4 |
| LGALS7B | Homo Sapiens | NM_001042507.3 |
| LGALS8 | Homo Sapiens | NM_006499.3 |
|  | Mus Musculus | NM_018886.4 |
| LGALS9 | Homo Sapiens | NM_009587.2 |
|  | Mus Musculus | NM_010708.2 |
| LGALS9B | Homo Sapiens | NM_001042685.1 |
| LGALS9C | Homo Sapiens | NM_001040078.2 |
| LGALS12 | Homo Sapiens | NM_001142535.1 |
|  | Mus Musculus | NM_019516.3 |
| LGALS13 | Homo Sapiens | NM_013268.2 |
| LGALS14 | Homo Sapiens | NM_020129.2 |

Fc Regions

The Fc region comprises the CH2 and CH3 domains of the immunoglobulin heavy chain and the hinge region. The hinge serves as a flexible spacer between the two parts of the Fc-fusion protein, allowing each part of the molecule to function independently.

In general, an Fc region from a human IgG will be used. In humans, there are four IgG isotypes: IgG1, IgG2, IgG3 and IgG4. The Fc region mediates effector functions, such as antibody-dependent cellular cytotoxicity (ADCC) and complement-dependent cytotoxicity (CDC). IgG isoforms exert different levels of effector functions increasing in the order of IgG4<IgG2<IgG1≤IgG3. Human IgG1 displays high ADCC and CDC, and is the most suitable for therapeutic use against pathogens and cancer cells. In some embodiments, a functional Fc region that binds the Fc receptor and allows antibody and complement-mediated cytotoxicity is used. In some embodiments, a mutated Fc region that is incapable of binding the Fc receptor is used. Variants of the Fc receptor can be used, e.g., as known in the art, so long as the fusion construct retains the ability to form multimers (i.e., dimers, tetramers, or both), and to induce apoptosis in activated T cells.

In some embodiments, the Fc region comprises SEQ ID NO:4:

(SEQ ID NO: 4)
DKTHTCPPCPAPELLGGPSVFLFPPKP-
KDTLMISRTPEVTCVVVDVSHEDPE

VKFNWYVDGVEVHNAKTKPREEQYN-
STYRVVSVLTVLHQDWLNGKEYKCKVS

NKALPAPIEK-
TISKAKGQPREPQVYTLPPSREEMTKNQVSLTCLVKGFYPSD

IAVEWESNGQPENNYKTTPPVLDSDGS-
FFLYSKLTVDKSRWQQGNVFSCSVM

HEGLHNHYTQKSLSLSPGK

In some embodiments, the variant is at least about 90%, 95%, 99%, or 100% identical to a reference Fc sequence described herein, e.g., SEQ ID NO:4.

Linkers

In some embodiments, the fusion constructs include a linker between the Fc region and the Gal-1. A linker can include at least one amino acid, and should not interfere with dimerization or function of the protein. In some embodiments, the linker is a flexible linker, e.g., includes amino acids that allow flexion at the joint between the Fc and the Gal-1. In some embodiments, the linker comprises, e.g., a sequence of 2 to 12, e.g., 5 to 10, or 6 to 8 amino acids. In some embodiments, the linker comprises the sequence RS (i.e., Arginine-Serine).

In some embodiments, the sequence of the Gal-Ig fusion protein is as shown in FIG. 22.

Isolated Nucleic Acid Molecules, Vectors, and Host Cells

In one aspect, the invention provides isolated or purified nucleic acid molecules that encode the Gal-Ig fusion constructs described herein. In some embodiments, the sequences include the human or mouse "wild type" sequences. In some embodiments, the sequences are altered to be species specific, e.g., to use codons that are more commonly used in a particular species, e.g., humanized.

The nucleic acid molecules encoding a Gal-Ig fusion protein as described herein can be alone or in a vector, e.g., an expression vector. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA.

Viral vectors include, e.g., replication defective retroviruses, adenoviruses and adeno-associated viruses.

A vector can include a Gal-Ig nucleic acid in a form suitable for expression of the nucleic acid in a host cell. The recombinant expression vector can include one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. When used in mammalian cells, for example, the expression vector's control functions are often provided by viral regulatory elements. For example, commonly used promoters are derived from polyoma, Adenovirus 2, cytomegalovirus and Simian Virus 40. The expression vectors of the invention can be introduced into host cells to thereby produce Gal-Ig fusion proteins as described herein.

The recombinant expression vectors of the invention can be designed for expression of Gal-Ig fusion proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Purified fusion proteins can be used, e.g., in the glycobiological assays as known in the art, or as the active agent in a Gal-Ig therapeutic composition as described herein.

To maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif., pp. 119-128 (1990)). Another strategy is to alter the nucleic acid sequence of the nucleic acid to be inserted into an expression vector so that the individual codons for each amino acid are those preferentially utilized in the cell type which is being used, e.g., *E. coli* (Wada et al., (1992) *Nucleic Acids Res.* 20:2111-2118). Such alteration of nucleic acid sequences of the invention can be carried out by standard DNA synthesis techniques.

The expression vector can be a yeast expression vector, a vector for expression in insect cells, e.g., a baculovirus expression vector or a vector suitable for expression in mammalian cells.

A host cell can be any prokaryotic or eukaryotic cell. For example, a Gal-Ig fusion protein can be expressed in bacterial cells such as *E. coli*, insect cells, yeast or mammalian cells (such as Chinese hamster ovary cells (CHO) or COS cells). Other suitable host cells are known to those skilled in the art. In some embodiments, the host cells are cells that grow in high numbers in suspension and/or that are capable of producing antibodies in large amounts. An exemplary cell line is the mouse J558L plasmacytoma line, which lacks endogenous heavy chain immunoglobulin but, retains the capacity of producing and secreting ectopically-expressed immunoglobulin or immunoglobulin like-molecules, is available from ATCC, Inc.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a Gal-Ig fusion protein. Accordingly, the invention further provides methods for producing a Gal-Ig fusion protein using host cells as described herein. In some embodiments, the methods include culturing a host cell (into which a recombinant expression vector encoding a Gal-Ig fusion protein has been introduced) in a suitable medium such that a Gal-Ig fusion protein is produced. In some embodiments, the method further includes isolating a Gal-Ig fusion protein from the medium or the host cell.

Also described herein are cells or purified preparation of cells that include a nucleic acid encoding a Gal-Ig fusion transgene. The cells can be human or non human cells, e.g., rodent cells, e.g., mouse or rat cells, rabbit cells, or pig cells.

Also provided are cells, preferably mammalian cells, e.g., mouse or human cells, in which the Gal-Ig fusion is stably expressed. In some embodiments, the cells are mouse J558L plasmacytoma cells (described in Krtiger-Krasagakes et al., Eur. J. Immunol., 23: 992-995, 1993).

Transgenic Animals

The invention provides non-human transgenic animals. Such animals are useful for producing large quantities of Gal-Ig fusion proteins. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal.

A tissue-specific regulatory sequence(s) can be operably linked to a transgene of the invention to direct expression of a Gal-Ig fusion protein to particular cells. A transgenic founder animal can be identified based upon the presence of a Gal-Ig fusion protein transgene in its genome and/or expression of Gal-Ig fusion mRNA in tissues or cells of the animals. A transgenic founder animal can then be used to breed additional animals carrying the transgene. Moreover, transgenic animals carrying a transgene encoding a Gal-Ig fusion protein can further be bred to other transgenic animals carrying other transgenes.

Gal-Ig fusion proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal as described herein.

Gal-Ig Compounds as Glycobiological Probes

The Gal-Ig compounds described herein can be used in a number of assays, as a stable, high-affinity receptor that binds native ligands on cells (or in cell lysates), e.g., for cell separation or detection, and as an anti-IgG Fc probe in immuno-detection assays, including Western blotting, flow cytometry, and immunohistochemistry. As one of skill in the art will appreciate, the Gal-Ig compounds can be used to detect the presence of any Galactin-1 ligand in a sample, whether the sample is an intact cell or tissue, or some portion thereof, e.g., a cell lysate or membrane preparation. A number of detection reagents are known in the art that can be used to detect the presence of the Gal-Ig compounds by binding to the Ig portion of the Gal-Ig compounds, e.g., anti-Ig antibodies or avid-conjugates recognizing biotinylated Gal-Ig versions.

The ability to detect Gal-1 ligand as well as to examine growth inhibitory activity in the absence of reducing agents will help clarify the authentic repertoire of Gal-1 ligands and more accurately depict the sensitivity and specificity of Gal-Ig binding on native T cell subsets in ex vivo-polarization models and in in vivo models of inflammation and cancer. The Gal-Ig constructs described herein are also useful as probes in glycobiology studies, e.g., for analyzing cell surface glycan expression.

Methods of Treating Subjects Using the Gal-Ig Compounds

The Gal-Ig compositions described herein can be administered to a subject to treat or prevent disorders associated with an overabundance of Galactin-1 ligand positive cells. Such cells can include activated T cells, in disorders associated with an abnormal or unwanted immune response, e.g., autoimmune disorders. Such cells can also include cancerous cells, e.g., cancerous hematopoietic cells, e.g., leukemic cells.

Methods of Treating Autoimmune Disorders

The Gal-Ig fusion proteins described herein can be used to treat autoimmune disorders, e.g., by affecting the functional properties of the circulating Th1/Th17 T cells (e.g., reducing their proliferative capacity) or by inducing regulatory cells. Examples of autoimmune disorders include, but are not limited to, Alopecia Areata, Lupus, Ankylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behçet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinaemia Sarcoidosis, Fibromyalgia, Scleroderma, Grave's Disease, Sjögren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Vasculitis, and Vitiligo. The Gal-Ig compositions described herein can be administered to a subject to treat or prevent disorders associated with an abnormal or unwanted immune response associated with cell, tissue or organ transplantation, e.g., renal, hepatic, and cardiac transplantation, e.g., graft versus host disease (GVHD), or to prevent allograft rejection.

In some embodiments, a therapeutically effective amount of a Gal-Ig composition can be, e.g., the amount necessary to reduce T1/Th17 cell proliferation by about at least 20%. In some embodiments, T1/Th17 cell proliferation is reduced by at least about 30%, about 40%, about 50%, about 60%, about 70% about 80%, or about 90% from pre-treatment levels. In addition, concentrations of IL-10 and/or TGF-β, or levels of cells secreting these cytokines, can be measured in the peripheral blood, e.g., using an enzyme-linked immunosorbent assay (ELISA) or a cell-based assay such as FACS scanning, to monitor the induction of tolerance. In some embodiments, a therapeutically effective amount of a Gal-Ig composition is the amount necessary increase levels of cells secreting IL-10 and/or TGF-β as measured in the peripheral blood by about 20% or more. In some embodiments, levels of cells secreting IL-10 and/or TGF-β as measured in the peripheral blood are increased by at least about 60%, 70%, 80%, 90%, or 100%, e.g., doubled.

The methods of treatment or prevention typically include administering to a subject a Gal-Ig composition sufficient to stimulate the regulatory immune system. In some embodiments, the methods include administering a Gal-Ig composition sufficient to increase IL-10 and/or TGF-β production by T1/Th17 cells in the peripheral blood, e.g., regulatory T cells, e.g., by about 100%, 200%, 300% or more. In some embodiments, the methods include administering a Gal-Ig composition sufficient to decrease T cell proliferation in the peripheral blood, e.g., by about 20%; e.g., in some embodiments, by at least about 20%, 30%, 40%, 50%, 60%, 70%, 80%, 90%, or more. In some embodiments, the methods include administering a Gal-Ig composition sufficient to increase serum concentrations of IL-10 and/or TGF-β, e.g., measured using an enzyme-linked immunosorbent assay (ELISA), to monitor the induction of tolerance to the self-antigen. In some embodiments, the methods include administering an Gal-Ig composition sufficient to increase levels of regulatory cells in the serum. In some embodiments, the methods include administering a Gal-Ig composition sufficient to produce an improvement in one or more clinical markers of disability; for example, in multiple sclerosis, such markers could include gadolinium-enhancing lesions visualized by MRI, or Paty's, Fazekas' or Barkhofs MRI criteria, or McDonald's diagnostic criteria; in diabetes, such markers could include blood or plasma glucose levels, glucosuria, ketonuria, polyuria, polydipsia, weight loss with normal or even increased food intake, fatigue, and blurred vision.

Cytokine Release Syndrome (CRS) is not expected to be associated with Gal-Ig compositions, but the methods can include monitoring the subjects for signs and symptoms of Cytokine Release Syndrome, particularly after the first few doses but also after a treatment hiatus with resumption of therapy; such methods are particularly useful in determining the safety of oral or mucosal administration of the Gal-Ig compositions. CRS is associated with arthralgias, myalgias, fevers, chills, hypoxia, nausea, and vomiting; severe cytokine release syndrome can cause pulmonary edema and suffocation. In some embodiments, the methods include lowering the subject's temperature to less than about 37.8° C. (100° F.) before the administration of any dose of the Gal-Ig compositions. In some embodiments, the methods include screening the subject for clinical evidence of volume overload, uncontrolled hypertension, or uncompensated heart failure. In some embodiments, the methods include not administering the Gal-Ig compositions to subjects who have evidence of any of, volume overload, uncontrolled hypertension, or uncompensated heart failure. In some embodiments, the methods involve evaluating the subject's pulmonary function, and not administering the Gal-Ig compositions to subjects who do not have a clear chest X-ray. In some embodiments, the methods include monitoring T cell (Th1/Th17) clearance, plasma levels of IL-10 and/or plasma levels of TGF-beta, and/or levels of Treg, and adjusting the dosage of the Gal-Ig compositions accordingly.

In some embodiments, the methods include administering to the subject methylprednisolone sodium succinate 8.0 mg/kg, e.g., intravenously, e.g., 1 to 4 hours before administration of the Gal-Ig compositions. In some embodiments, the methods can include administering to the subject an anti-inflammatory agent, e.g., acetaminophen or antihistamine, before, concomitantly with, or after administration of the Gal-Ig compositions.

In some embodiments, the methods include evaluating and/or monitoring a subject for anti-mouse Gal-1 antibodies, and discontinuing administration of the Gal-Ig compositions if the subject has anti-mouse Gal-1 antibody titers of greater than about 1:1000.

In some embodiments, the Gal-Ig compositions are administered concurrently with one or more second therapeutic modalities, e.g., symptomatic treatment, high dose immunosuppressive therapy and/or autologous peripheral blood stem cell transplantation (HSCT). Such methods are known in the art and can include administration of agents useful for treating an autoimmune disorder, e.g., NSAIDs (including selective COX-2 inhibitors); other antibodies, e.g., anti-cytokine antibodies, e.g., antibodies to IFN-α, IFN-γ, and/or TNF-α; gold-containing compounds; heat shock proteins (e.g., as described in U.S. Pat. No. 6,007,821); immunosuppressive drugs (such as corticosteroids, e.g., prednisolone and methyl prednisolone; cyclophosphamide; azathioprine; mycophenolate mofetil (MMF); cyclosporin and tacrolimus; methotrexate; or cotrimoxazole) and therapeutic cell preparations, e.g., subject-specific cell therapy, hematopoietic stem cell therapy. In some embodiments, the methods include administering one or more treatments for multiple sclerosis, e.g., γ-interferons (e.g., interferon γ-1a, interferon γ-1b), mitoxantrone, or glatiramer acetate. In some embodiments, the methods include administering one or more non-Gal-Ig immunosuppressive drugs (such as corticosteroids, e.g., prednisolone and methyl prednisolone; cyclophosphamide; azathioprine; mycophenolate mofetil (MMF); cyclosporin and tacrolimus; methotrexate; or cotrimoxazole) to the subject, e.g., before, during, or after administration of the Gal-Ig compositions.

In some embodiments, the methods include administering one or more standard treatments for diabetes, e.g., administration of one or more agents useful in the treatment of diabetes, e.g., insulin, sulfonylureas (e.g., meglitinides and nateglinides), biguanides, thiazolidinediones, and alpha-glucosidase inhibitors, inter alia, as well as modification of diet or exercise regime.

Treatment or Prevention of Multiple Sclerosis

Multiple Sclerosis (MS) is typically characterized clinically by recurrent or chronically progressive neurologic dysfunction, caused by lesions in the CNS. Pathologically, the lesions include multiple areas of demyelination affecting the brain, optic nerves, and spinal cord. The underlying etiology is uncertain, but MS is widely believed to be at least partly an autoimmune or immune-mediated disease.

Thus, the invention includes methods of treating, delaying or preventing the onset of MS, by administering a Gal-Ig composition.

Included are methods wherein a subject who has or is at risk of having MS is administered Gal-Ig composition. In one aspect, the invention features methods of screening for subjects at risk for MS, e.g., by screening for one or more indicators of MS to evaluate if the subject is at risk for developing MS, and administering a Gal-Ig composition if the subject is determined to be at risk. As susceptibility to MS is at least partly familial, subjects who have a relative with MS can be considered at increased risk for developing MS.

In some embodiments, the methods include administering a therapeutically effective amount of a Gal-Ig composition to a subject diagnosed with MS. The diagnosis of MS is typically made on the basis of the clinical signs and symptoms, include heat sensitivity, internuclear ophthalmoplegia, optic neuritis, and Lhermitte symptom (see, e.g., McDonald et al., Recommended Diagnostic Criteria for Multiple Sclerosis: Guidelines From the International Panel on the Diagnosis of Multiple Sclerosis. Ann. Neurol. 50:121, 2001). A therapeutically effective amount can be an amount sufficient to prevent the onset of an acute episode or to shorten the duration of an acute episode, or to decrease the severity of one or more symptoms, e.g., heat sensitivity, internuclear ophthalmoplegia, optic neuritis, and Lhermitte symptom. In some embodiments, a therapeutically effective amount is an amount sufficient to prevent the appearance of or promote the healing of a demyelinated lesion in one or more of the brain, optic nerves, and spinal cord of the subject, e.g., as demonstrated on MRI.

In some embodiments, the Gal-Ig composition is administered in combination with a standard treatment for MS, e.g., administration of corticosteroid therapy, interferon beta-1b, Glatiramer, mitoxantrone, cannabis, or a combination thereof. In some embodiments, the Gal-Ig composition is administered in combination with a treatment for one or more symptoms of MS, e.g., depression and fatigue, bladder dysfunction, spasticity, pain, ataxia, and intention tremor; such treatments include pharmacological agents, exercise, and appropriate orthotics. Additional information on the diagnosis and treatment of MS can be found at the National MS Society website, on the world wide web at nationalmssociety.org, the contents of which are incorporated by reference herein.

The median time from onset of disease to disability severe enough for the subject to require aids for ambulation is about 15 years; thus, in some embodiments the invention includes a method of delaying the onset of disability due to MS comprising administering a therapeutically effective amount of a Gal-Ig composition.

Treatment of Autoimmune Arthritis

Rheumatoid arthritis (RA) is the most common chronic inflammatory arthritis and affects about 1% of adults; it is two to three times more prevalent in women than in men. RA may begin as early as infancy, but onset typically occurs in the fifth or sixth decade. Diagnosis may be made according to the American Rheumatism Association Criteria for the Classification of Rheumatoid Arthritis. A therapeutically effective amount will cause an improvement in one or more of the following: the number of inflamed joints, the extent of swelling, and the range of joint motion. Laboratory measurements (e.g., ESR and hematocrit value) and assessments of subjective features (e.g., pain and morning stiffness) can also be made. The invention includes methods of treating autoimmune arthritis, e.g., RA, in a subject by administering to the subject a therapeutically effective amount of a Gal-Ig composition.

In some embodiments, the methods include the administration of a second therapeutic agent, e.g., for analgesia, to additionally control inflammation, and/or to alter the natural history of the disease. A number of such agents are known in the art. For example, one or more of NSAIDs, methotrexate, prednisone, TNF inhibitors, leflunomide, or sulfasalazine (with or without hydroxychloroquine) can be administered. Immunosuppressive agents such as azathioprine or cyclosporine can also be used.

Methods of Treating Autoimmune Disorders and Cancer

The Gal-Ig compositions described herein can also be used to treat autoimmune disorders and cancers, i.e., cancers associated with unwanted proliferation of cells that express a galactin-1 ligand on the cell surface. Such cells include activated or malignant leukocytes or solid cancer cells including but not limited to malignant melanoma, adenocarcinoma and sarcoma cancer cells, as well as hematologic malignancies (e.g. lymphomas and leukemias).

In some embodiments, a therapeutically effective amount of a Gal-Ig composition can be, e.g., the amount necessary to reduce cancer cell proliferation by about at least 20%. In some embodiments, cancer cell proliferation is reduced by at least about 30%, about 40%, about 50%, about 60%, about 70% about 80%, or about 90% from pre-treatment levels.

In some embodiments, a therapeutically effective amount of a Gal-Ig composition can be, e.g., the amount necessary to reduce cancer cell populations (i.e., the number of cancer cells in a tissue or subject) by about at least 20%. In some embodiments, cancer cell populations are reduced by at least about 30%, about 40%, about 50%, about 60%, about 70% about 80%, or about 90% from pre-treatment levels.

In some embodiments, the methods include administering one or more treatments for cancer, e.g., surgery, a chemotherapeutic agent or radiation therapy, in addition to the Gal-Ig composition.

In some embodiments, the Gal-Ig composition is administered systemically or locally to a cancerous tissue. In some embodiments, e.g., for the treatment of a hematopoietic cancer, the Gal-Ig is administered extracorporeally, e.g., as part of a plasmapheresis regimen, to remove cells that have the Gal-1 ligand on their surface.

Pharmaceutical Compositions and Methods of Administration

The methods described herein include the manufacture and use of pharmaceutical compositions, which include Gal-Ig fusion compounds described herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., anti-inflammatory compounds as known in the art and described herein.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587.

Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

EXAMPLES

The invention is further described in the following examples, which do not limit the scope of the invention described in the claims. In the following, statistically significant comparisons were ascertained between groups using a paired t-test.

Example 1

Cloning of Gal-1 and Production of Mouse Gal-1-Human IgG Fc1 (Gal-Ig) Chimeric Fusion Protein Using chemical stabilization to help promote Gal-1 dimers from a monomer/dimer/multimer equilibrium is critical in Gal-1 research. Inclusion of DTT in rGal-1 preparations could potentially bias cell death-related conclusions and even underestimate Gal-1's effects on cytokine modulation.

To circumvent this pitfall, a chimeric protein was engineered wherein mouse Gal-1 cDNA was linked in frame to the Fc portion of human IgG1 using the pFUSE-hIgG1-Fc1 expression system (Gal-1hFc)

RT-PCR with the primers shown in Table 2 was used to clone mouse Gal-1 from spleen mRNA. The forward primer included a Kozak sequence (gccacc)

TABLE 2

Primers for Cloning of Gal-I

| Sequence | Primer | restriction site | SEQ ID NO: |
|---|---|---|---|
| 5' cgacctcgaggccacccgtctctcgggtggagtc 3' | Forward | XhoI<br>C \| TCGAG | 5 |
| 5' ccgagatctctcaaaggccacgcacttaatctt 3' | Reverse | BglII<br>A \| GATCT | 6 |

Figure 3:
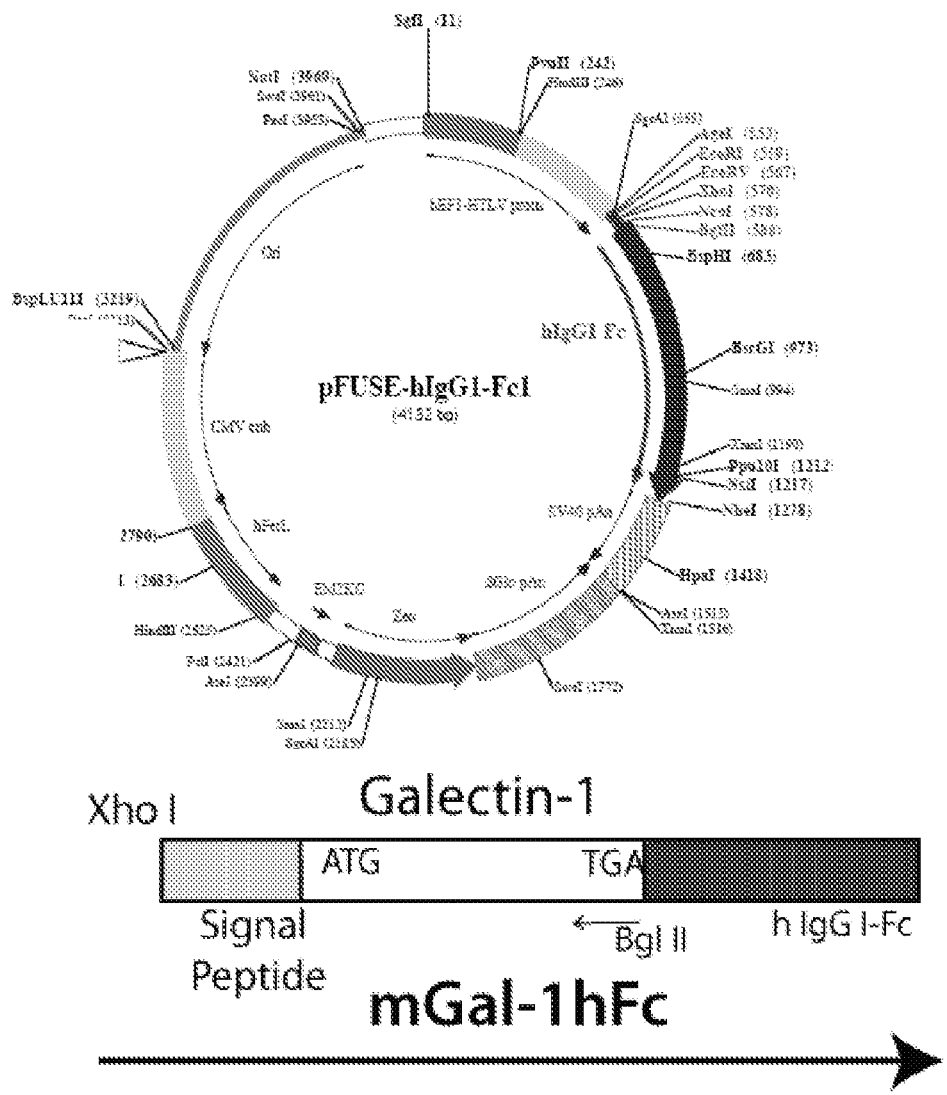
FIG. 3 is a diagram showing an exemplary Gal-Ig fusion construct in a mammalian expression vector, the pFUSE-IgG1 Fc1 (InvivoGen, Inc. Cat# pfuse-hg1fc) plasmid DNA (InvivoGen, Inc.). Mouse Gal-1 cDNA insertion and orientation was validated by Xho-1/Bgl11 plasmid restriction digest and by DNA sequencing.

The sequence of the obtained Gal-1 cDNA was as follows (a signal peptide sequence is underlined, start and stop codons are in bold font, and restriction enzyme recognition sites are in upper case):

(SEQ ID NO: 7)
cgacCTCGAGgccacccgtctctcgggtggagtcttctgactgctggtgga gcaggtctcaggaatctcttcgcttcagcttcaatcatggcctgtggtctg gtcgccagcaacctgaatctcaaacctggggaatgtctcaaagttcgggga gaggtggcctcggacgccaagagctttgtgctgaacctgggaaaagacagc aacaacctgtgccctacacttcaatcctcgcttcaatgccatggagacgcc aacaccattgtgtgtaacaccaaggaagatgggacctggggaaccgaacac cgggaacctgccttcccccttccagcccgggagcatcacagaggtgtgcatc acctttgaccaggctgacctgaccatcaagctgccagacggacatgaattc aagttccccaaccgcctcaacatggaggccatcaactacatggcggcggat ggagacttcaagattaagtgcgtggcctttgagtgaagAGATCTcgg The obtained Gal-1 cDNA was ligated into a eukaryotic expression vector containing the Fc region of human IgG1 and the drug resistance gene for Zeocin (pFUSE-hIgG-Fc1; InvivoGen, Inc.) (FIG. 3). Competent DH5a E. coli were transformed, and plasmid DNA encoding for the Gal-1-hFc (Gal-Ig) was purified and diagnosed for presence and orientation of the ligated Gal-Ig insert.

The following sequence data was obtained using a 5' forward primer. The sequence for the Gal-1 portion is shown in bold, and the non-bolded sequence following is the IgG. N represents nucleotides that were not resolved in this sequencing assay.

```
                                                                    (SEQ ID NO: 8)
NNNNNNNNNNNNTGCNNNNNNNNATCCAGCTGTGACCGGCGCCTACCTGAGATCACCGGTGAATTCGATATC

TCGAGGCCACCCGTCTCTCGGGTGGAGTCTTCTGACTGCTGGTGGAGCAGGTCTCAGGAATCTCTTCGCTT
XhoI    Kozak CAGCTTCAATCATGGCCTGTGGTCTGGTCGCCAGCAACCTGAATCTCAAACCTGGGGAATG
          Start - Galectin-1 portion

TCTCAAAGTTCGGGGAGAGGTGGCCTCGGACGCCAAGAGCTTTGTGCTGAACCTGGGAA

AAGACAGCAACAACCTGTGCCTACACTTCAATCCTCGCTTCAATGCCCATGGAGACGCC

AACACCATTGTGTGTAACACCAAGGAAGATGGGACCTGGGGAACCGAACACCGGGAACC

TGCCTTCCCCTTCCAGCCCGGGAGCATCACAGAGGTGTGCATCACCTTTGACCAGGCTG

ACCTGACCATCAAGCTGCCAGACGGACATGAATTCAAGTTCCCCAACCGCCTCAACATG

GAGGCCATCAACTACATGGCGGCGGATGGAGACTTCAAGATTAAGTGCGTGGCCTTTGA

GAGATCTGACAAAACTCACACATGCCCACCGTGCCCAGCACCTGAACTCCTGGGGGACCGTCAGTCTTCC
Bgl-11 Linking Gal-1 and encoding sequence for human IgG Fc1

TCTTCCCCCCAAAACCCAAGGACACCCTCATGATCTCCCGGACCCCTGAGGTCACATGCGTGGTGGTGGAC

GTGAGCCACGAAGACCCTGAGGTCAAGTTCAACTGGTACGTGGACGGCGTGGAGGTGCATAATGCCAAGAC

AAAGCCGCGGGANGAGCAGTACAACAGCACGTACCGTGTGGTCAGCGTCCTCACCGTCCTGCACCAGGACT

GGCTGAATGGCAAGGANTACAAGTGCAAGGTCTCCAACAAAGCCCTCCCAGCCCCCATCGAGAAAACCATC

TCCAAAGCCAAAGGGCAGCCCCGANAACACAGGTGTACACCCTGCCCCCATCCCGGGNNGAGANGANCNA

GAACCANGTCAGCCNGANNTGNNTNGNCAAANNCTNCTATNCCNNCNNNNTC
```

To control for carbohydrate-binding activity of Gal-1hFc, genetic mutants were created in which a key tryptophan residue for carbohydrate recognition via van der Waals interactions in the 69$^{th}$ amino acid position was substituted for a glycine (mGal-1hFc) and a histidine also important for carbohydrate-binding through the formation of hydrogen bonds in the 45$^{th}$ position was substituted for a leucine (dmGal-1hFc). The sequences used were as follows:

```
Gal-1                                     (SEQ ID NO: 1)
MACGLVASNLNLKPGECLKVRGEVAS-
DAKSFVLNLGKDSNNLCLHFNPRFNA

HGDANTIVCNTKEDGTWGTEHREPAF-
PFQPGSITEVCITFDQADLTIKLPDG

HEFKFPNRLNMEAINYMAADGDFKIKCVAFE mGal-1                                    (SEQ ID NO: 9)
MACGLVASNLNLKPGECLKVRGEVAS-
DAKSFVLNLGKDSNNLCLHFNPRFNA

HGDANTIVCNTKEDGTGGTEHREPAF-
PFQPGSITEVCITFDQADLTIKLPDG

HEFKFPNRLNMEAINYMAADGDFKIKCVAFE dmGal-1                                   (SEQ ID NO: 10)
MACGLVASNLNLKPGECLKVRGEVAS-
DAKSFVLNLGKDSNNLCLLFNPRFNA

HGDANTIVCNTKEDGTGGTEHREPAF-
PFQPGSITEVCITFDQADLTIKLPDG

HEFKFPNRLNMEAINYMAADGDFKIKCVAFE
```

Since J558L murine plasmacytoma cells are capable of producing greater amounts of ectopic fusion protein compared with CHO or HEK293 cells (Howard, M. R., A. P. Lodge, J. E. Reed, C. J. McNamee, and D. J. Moss. 2002. High-level expression of recombinant Fc chimeric proteins in suspension cultures of stably transfected J558L cells. Biotechniques 32:1282-1286, 1288), J558L cells were transfected, drug-selected, sub-cloned and assayed for Gal-1hFc expression by RT-PCR and Western blotting.

Using a LIPOFECTAMINE™ transfection method, murine plasmacytoma J558L cells from ATCC, Inc. were transfected with purified Gal-Ig plasmid and selected drug resistant cells with Zeocin. To confirm RNA and protein expression of Gal-Ig, Zeocin-resistant J558L cells were then harvested and RNA and protein were extracted for analysis by RT-PCR and Western blotting, respectively. When compared with J558L cells transfected with empty vector, RT-PCR analysis of Gal-Ig revealed that Gal-Ig-transfected J558L cells contain mRNA of Gal-Ig. Moreover, when compared to empty vector transfectant protein, protein from Gal-Ig-transfected J558L cells contained Gal-Ig as determined by Western blotting with anti-Gal-1 Abs.

Following expansion of Zeocin-resistant cells in 10% FBS containing medium, the transfectants were subsequently growth in serum-free conditions to help eliminate IgG present in the supernatant that could contaminate Gal-Ig isolates. Gal-Ig-transfected J558L serum free supernatants were harvested and subjected to protein-G affinity chromatography. Briefly, Gal-Ig-transfected J558L cell supernatants and protein-G-agarose were incubated, and then Gal-Ig bound to protein G was eluted using low pH conditions and neutralized. Gal-Ig expression was then confirmed by Western blotting with anti-Gal-1 moAb.

A mutated Gal-1hFc construct, wherein tryptophan-69 was substituted for a glycine (W69G Gal-1hFc or mGal-1hFc), was produced using the PCR-site directed mutagenesis GeneTailor System (Invitrogen) with the following primers: Forward 5' ACCAAGGAAGATGGGACCGGGGGAACC GAACAC 3' (SEQ ID NO: 11), Reverse 5' GGTCCCATCT-TCCTTGGTGTTACACACAAT 3' (SEQ ID NO: 12). DH5α-T1r competent cells were transformed with the methylated Gal-1hFc PCR product, plasmid DNA was purified using a Plasmid mini kit, and further validated by DNA sequencing. Using the mGal-1hFc plasmid DNA as a template, a double mutant (W69G H45L Gal-1hFc or dmGal-1hFc) construct, wherein histidine-45 was substituted for a leucine, was produced as above with following primers: Forward 5'ACAACCTGTGCCTACTCTTCAAT CCTCGCT 3' (SEQ ID NO: 13), Reverse 5' GTAGGCACAGGTTGT-TGCTGTCTCTTCCCA 3' (SEQ ID NO: 14).

Stable clones secreted a Gal-1hFc and mutant protein, which was isolated by protein G affinity chromatography and resolved at the predicted sizes of 40.7 kDa and 81.4 kDa under reducing and non-reducing conditions, respectively (FIGS. 4 and 5), suggesting that this Gal-Ig fusion construct may be suitable for use in cellular assays and apoptosis induction studies without the use of reducing agents.

Example 2

Expression Analysis of Gal-1 Ligands on Hematopoietic Cell Lines, Ex Vivo T Cell Subsets and Fresh Isolates of Activated T Cells To validate Gal-1hFc-binding function, binding assays were performed using mouse and human hematopoietic cells and solid tumor cell lines. Cells ($1 \times 10^6$) previously incubated with a human FcγR-binding inhibitor (eBioscience, Inc., San Diego, Calif.) were subsequently incubated at 4° C. for 45 min with Gal-1hFc or mutants (all at 20 μg/mL) in the presence or absence of 50 mM lactose or sucrose. Then, cells were incubated for 30 min at 4° with APC-conjugated goat F(ab')$_2$ anti-human Fc, and analyzed by flow cytometry in a FACS-Canto (BD Biosciences) and then using Flowjo 8.1 (Tree Star Inc., Ashland, Oreg.).

Figure 6A:
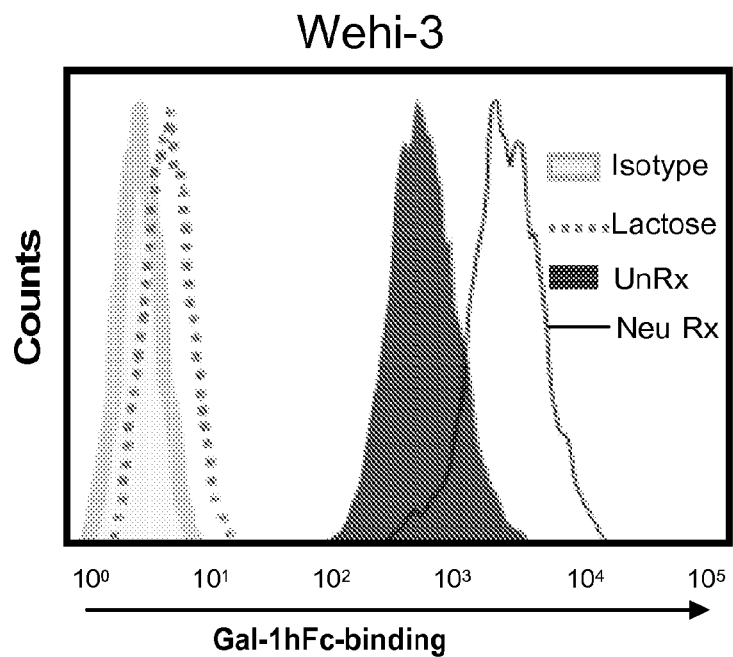
FIGS. 6A-6E are a set of graphs showing the results of flow cytometric analysis of Gal-ligand expression with Gal-Ig. (6A), Gal-1hFc-binding to untreated Wehi-3 cells or cells treated with *Vibrio cholerae* neuraminidase (0.2 U/mL) for 30 min. at 37° C. was assessed in the presence or absence of 50 mM lactose; (6B), Gal-1hFc-binding was assayed on PCa PC3 cells and on PC-3α1,3 fucosyltransferase 7 (FT7) transfectants (Barthel, S. R., G. K. Wiese, J. Cho, M. J. Opperman, D. L. Hays, J. Siddiqui, K. J. Pienta, B. Furie, and C. J. Dimitroff. 2009. Alpha 1,3 fucosyltransferases are master regulators of prostate cancer cell trafficking Proc Natl Acad Sci USA 106:19491-19496); (6C), Gal-1hFc- and mGal-1hFc-binding were examined on HL-60 cells in the presence or absence of 50 mM lactose or sucrose; (6D) dmGal-1hFc-binding was also examined on HL-60 cells. Gal-Ig-binding to cells was dose-dependent (6E).
Figure 6B:
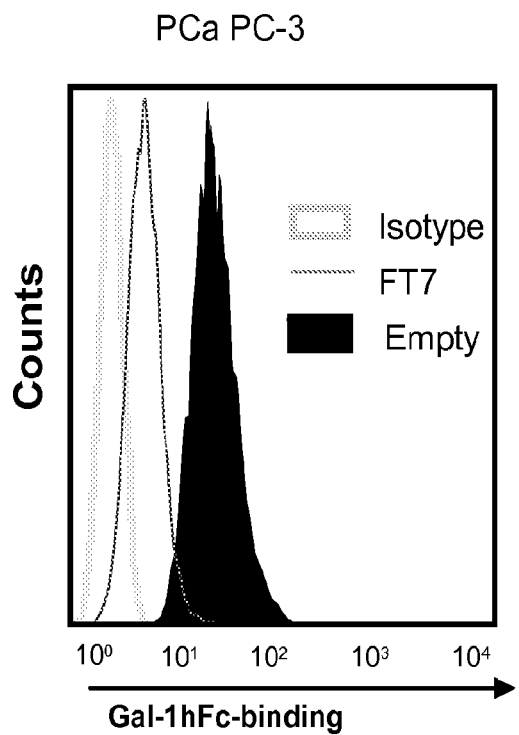
Figure 6C:
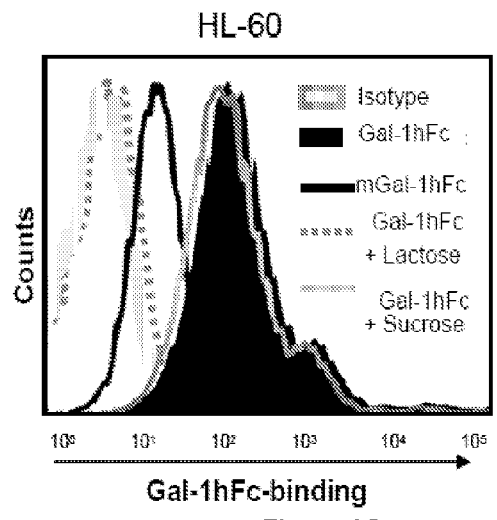
Figure 6D:
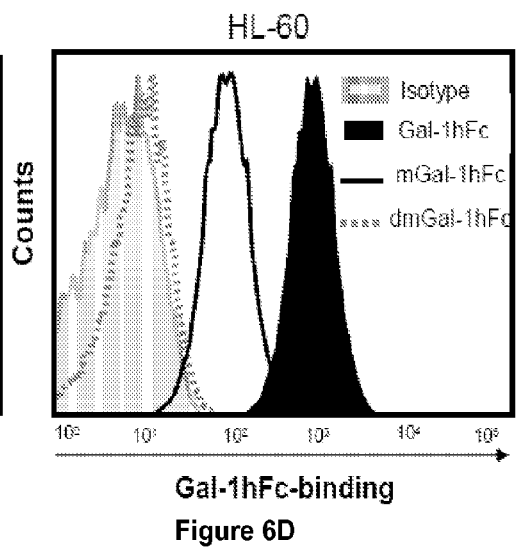
Figure 6E:
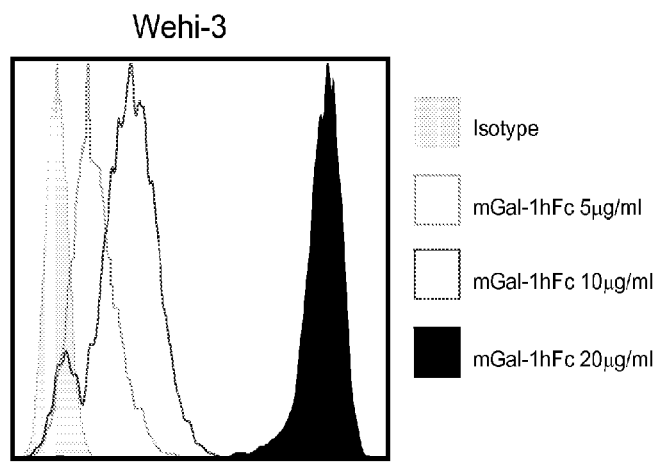

Gal-1hFc bound mouse WEHI-3 and human HL-60 leukemic cell lines and binding was inhibited by 50 mM lactose, but not sucrose (FIGS. 6A and 6C), and was dependent on Gal-Ig concentration (FIG. 6E). Importantly, removal of terminal sialic acid residues by neuraminidase treatment enhanced WEHI-3 binding, whereas binding to human PC-3 prostate cancer cells (PC-3) overexpressing α1,3 fucosyltransferase 7 (Hirabayashi, J., T. Hashidate, Y. Arata, N. Nishi, T. Nakamura, M. Hirashima, T. Urashima, T. Oka, M. Futai, W. E. Muller, F. Yagi, and K. Kasai. 2002. Oligosaccharide specificity of galectins: a search by frontal affinity chromatography. Biochim Biophys Acta 1572:232-254) was diminished compared with parental cells, validating published data on Gal-1 carbohydrate-binding properties (Hirabayashi, J., T. Hashidate, Y. Arata, N. Nishi, T. Nakamura, M. Hirashima, T. Urashima, T. Oka, M. Futai, W. E. Muller, F. Yagi, and K. Kasai. 2002. Oligosaccharide specificity of galectins: a search by frontal affinity chromatography. Biochim Biophys Acta 1572:232-254) (FIG. 6B). Binding of mGal-1hFc to HL-60 cells was diminished by ~50%, as previously described (FIG. 6C) (Levi, G., and V. I. Teichberg. 1981. Isolation and physicochemical characterization of electrolectin, a beta-D-galactoside binding lectin from the electric organ of Electrophorus electricus. J Biol Chem 256:5735-5740; Hirabayashi, J., and K. Kasai. 1991. Effect of amino acid substitution by sited-directed mutagenesis on the carbohydrate recognition and stability of human 14-kDa beta-galactoside-binding lectin. J Biol Chem 266:23648-23653), while dmGal-1hFc binding was completely abolished (FIG. 6D).

To further characterize the specificity of glycan binding, Gal-1hFc-binding was assayed on 442 immobilized glycans as previously described (Tsai, C. M., Y. K. Chiu, T. L. Hsu, I. Y. Lin, S. L. Hsieh, and K. I. Lin. 2008. Galectin-1 promotes immunoglobulin production during plasma cell differentiation. J Immunol 181:4570-4579). Briefly, Gal-1hFc (200 μg/ml) or control hFc (200 μg/ml) in binding buffer (1% BSA, 150 mM NaCl, 2 mM CaCl$_2$, 2 mM MgCl$_2$, 0.05% Tween 20, and 20 mM Tris-HCL (pH 7.4) was incubated for 1 h at room temperature on the printed glycan array (Version 4.0) followed by a 1 h incubation with APC-conjugated goat F(ab')$_2$ anti-human Fc (5 ug/mL). After washing to remove excess reagents, the slides were dried and scanned at an excitation wavelength of 633 nm to detect the APC fluorophore. The array is comprised of glycans printed in replicates of 6 and relative fluorescence was reported as the average of 4 after removal of the highest and lowest point from each set of 6 replicates. Mean fluorescence intensities of Gal-1hFc-binding were normalized to control hFc binding and graphically represented as mean fold difference.

Figure 6F:
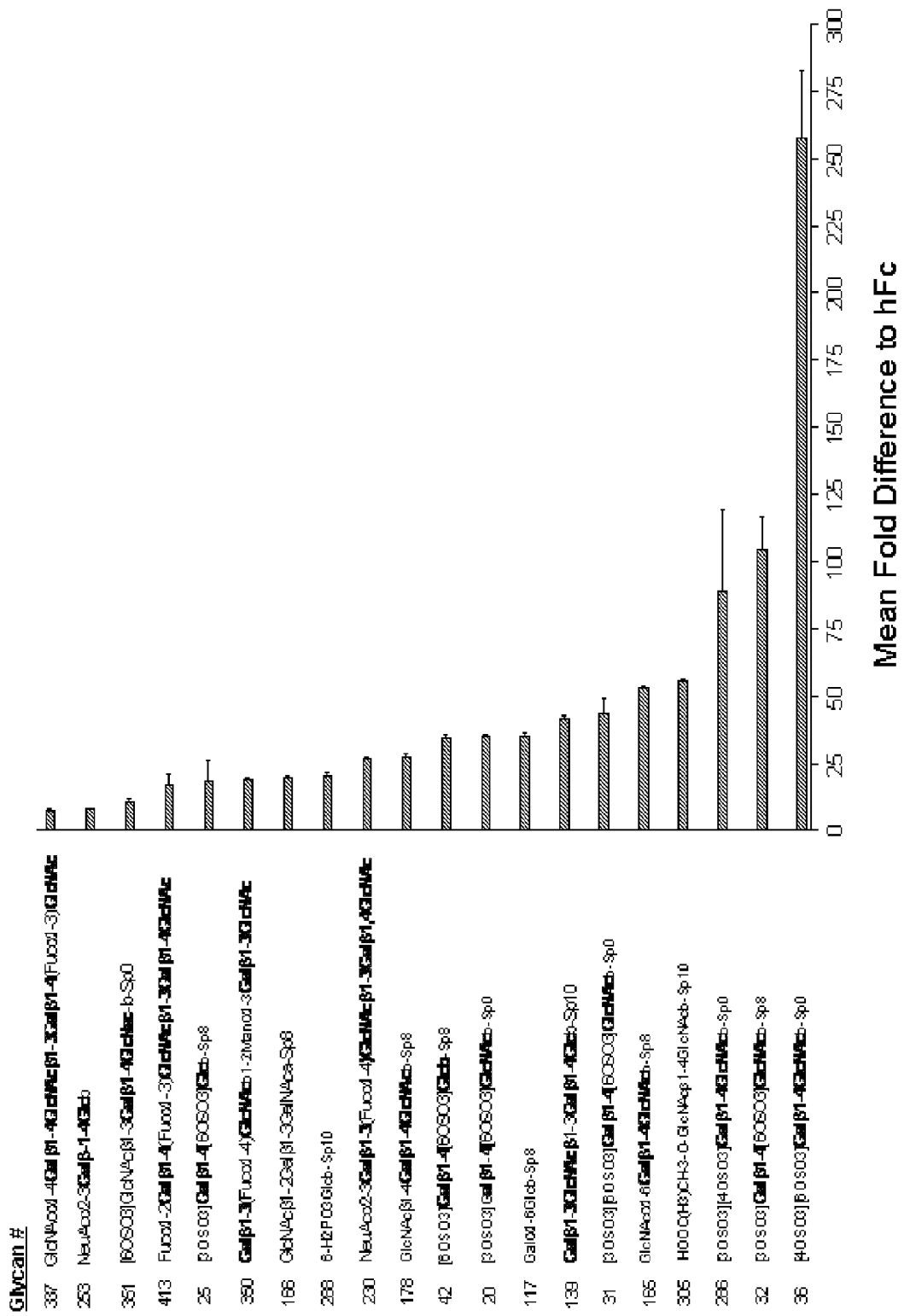
FIG. 6F is a bar graph showing the results of an experiment in which Gal-1hFc or hFc was incubated on a covalent printed glycan array. Mean fluorescence intensities of Gal-1hFc-binding were normalized to control hFc-binding and graphed as Mean Fold Difference to hFc. The top 20 glycans were listed, as follows; the left column is the glycan number.

Due to the relative carbohydrate-binding properties of human IgG (von Gunten, S., D. F. Smith, R. D. Cummings, S. Riedel, S. Miescher, A. Schaub, R. G. Hamilton, and B. S. Bochner. 2009. Intravenous immunoglobulin contains a broad repertoire of anticarbohydrate antibodies that is not restricted to the IgG2 subclass. J Allergy Clin Immunol 123: 1268-1276 e1215), Gal-1hFc binding was normalized to that of human IgG. As expected, Gal-1hFc exhibited highest affinity for structures bearing multiple type 1 (Galβ1,3) or type 2 (Galβ1,4) lactosaminyl moieties (FIG. 6F). Interestingly, Gal-1hFc also bound sulfated lactosamine structures, similar to a human Gal-1Ig molecule previously reported (Tsai et al., 2008, supra) and to most recombinant Gal-1 forms reported by Core H of the Consortium for Functional Glycomics (FIG. 6F). Noteworthy, to avoid saturation levels and nonspecific glycan binding observed when molar concentrations of lectins are used in glycan arrays, 20 μg/ml Gal-1hFc (0.48 μM) was used, similar to other reports (Song, X., B. Xia, S. R. Stowell, Y. Lasanajak, D. F. Smith, and R. D. Cummings. 2009. Novel fluorescent glycan microarray strategy reveals ligands for galectins. Chem Biol 16:36-47). mGal-1hFc bound ~50% less to the printed glycan microarray, which was compatible with binding activity measured by flow cytometry.

To determine whether Gal-Ig can recognize Gal-1 ligands on 4-F-GlcNAc-treated cells, human hematopoietic KG1a cells were treated with non-growth-inhibitory concentrations of 4-F-GlcNAc for 48 hr and then analyzed Gal-ligand expression by flow cytometry with Gal-Ig. 4-F-GlcNAc elicited dose-dependent inhibition of Gal-1 ligand expression (FIGS. 7A-B).

In an ex vivo cytokine-induced model of T cell polarization, we observed differential expression of Gal-1 ligands in ex vivo-generated Th$_1$ and Th$_2$ cells (FIG. 8A). As expected, treatment of these Th$_1$ cell cultures with 4-F-GlcNAc markedly diminished Gal-Ig binding (FIG. 8A). To examine Gal-Ig recognition of Gal-1 ligands on activated antigen-specific T cells, we used a dendritic DC-induced T cell activation model, in which naïve T cells were primed by dendritic cells (DC) in lymph nodes (LN)-draining dinitrofluorobenzene (DNFB)-sensitized skin. LNs draining DNFB-sensitized skin were isolated, and lymphocytes were released by mechanical disruption. Compared with T cells from naïve LNs, DNFB-activated T cells expressed Gal-1 ligands (FIG. 8B).

To solidify prior findings suggesting that α1,3 fucosylation dampens Gal-1 binding and de-sialylation enhances Gal-1 binding, we analyzed human prostate tumor PC-3 cells stably transfected with human fucosyltransferase VII (FT7) or treated WEHI-3 cells with α2,3/α2,6 Vibrio cholerae neuraminidase. We found that FT7 expression reduced Gal-Ig-binding, while neuraminidase treatment augmented Gal-Ig binding (FIGS. 9A-B).

Example 3

Use of Gal-Ig as an Immunohistochemical and Western Blotting Probe

To further characterize the binding properties of Gal-Ig and test its utility in other biochemical assays, Leukemic HL-60/Wehi-3 cell pellets or mouse LNs (unactivated or DNFB-activated) were fixed in 10% formalin, embedded in paraffin, sectioned and immunostained with Gal-1hFc or controls (hFc/dmGal-1hFc) and counterstained with hematoxylin. Bars=20 mm. The results are shown in FIGS. 10A-B. Gal-1hFc staining showed distinct cellular reactivity with spatial emphasis in the paracortical region surrounding high endothelial venules where T cells reside, whereas hFc control staining did not show any reactivity (FIGS. 10A and B).

This is the first demonstration of a Gal-1 formulation used as an immunohistochemical tool for analysis of Gal-1 ligands. Non-specific binding through the Fc domain is controlled for by staining with hFc alone or with a non-binding lectin mutant, dmGal-1hFc.

In addition, Gal-1hFc can be used as a probe in Western Blotting methods. CD45 was immunoprecipitated from mouse activated Th cells with anti-CD45 mAb or isotype control, analyzed by SDS-PAGE/Western blotting and immunostained with anti-mouse CD45 or Gal-1hFc. Similar results were seen with both, with a clear band apparent at about 190 kDa, the expected size of CD45, a candidate Gal-1 ligand. These data confirm that Gal-1hFc can function as a Gal-1 ligand probe on Western blots, eliminating the burdensome creation of lectin affinity columns for the detection of authentic Gal-1 ligands. Noteworthy, this application is not easily attained with biotinylated recombinant Gal-1 due to cross-reactivity with avidin-reactive structures in protein lysates.

Finally, Gal-1hFc can be used to detect Gal-1 ligands in multi-color FACS methods, as analysis of Gal-1 ligands in Th subsets by 2-color flow cytometry was performed successfully. The results validated previously published data regarding presence of Gal-1 ligands on Th1 and Th17 cell subsets. While only a small percentage of Th2 cells bind to Gal-1hFc.

Gal-1hFc is a powerful tool to discern presence and relevance of Gal-1 ligands in mouse and human cells and tissue.

Example 4

Th1 and Th17 Cells are Susceptible to Gal-1hFc-Mediated Apoptosis

Pro-inflammatory Th1 and Th17 cell subsets share common glycan motifs, such as abundant asialocore-1 O-glycans along with small amounts of sialic acida-2,6-galactose residues on their surfaces (Toscano, M. A., G. A. Bianco, J. M. Ilarregui, D. O. Croci, J. Correale, J. D. Hernandez, N. W. Zwirner, F. Poirier, E. M. Riley, L. G Baum, and G A. Rabinovich. 2007. Differential glycosylation of TH1, TH2 and TH-17 effector cells selectively regulates susceptibility to cell death. Nat Immunol 8:825-834). To determine whether Gal-1hFc can bind these Th subsets, mouse Th1, Th2 and Th17 subsets were polarized ex-vivo, their identity was confirmed by intracellular cytokine staining, and Gal-1hFc-binding activity was assayed.

Polarization was achieved as follows. Naïve CD4+ T cells were isolated from 6-week old C57BL/6 mouse spleens by immunomagnetic bead positive selection (Miltenyi Biotec, Inc., Auburn, Calif.) and polarized into Th1, Th2, Th17 subsets as previously described (Toscano et al., 2007, supra). Briefly, cells were resuspended ($1.5 \times 10^6$ cells/ml), and stimulated for 72 h with plate-bound anti-CD3 (5 µg/ml) and soluble anti-CD28 (1 µg/ml). For Th1 polarization, 10 ng/mL IL-12 and 40 U/mL anti-IL-4 were added; for Th2 polarization, 20 ng/ml IL-4, 2 µg/ml anti-IL-12, and 25 U/mL IL-2 were added; for Th17 polarization, 20 ng/ml IL-6, 10 ng/ml IL-23, 5 ng/ml TGF-beta$_1$, 10 µg/ml anti-IFN-gamma, 10 µg/ml anti-IL-4, and 10 µg/ml anti-IL-2 were added. Th1 and Th2 cells were expanded with RPMI-1640 supplemented with 25 U/ml IL-2; and Th17 cells were expanded with 10 ng/ml IL-23 for 4 additional days. All cytokines and antibodies were purchased from BD Biosciences.

Th1 and Th17 cells expressed high levels of Gal-1 ligands as determined by Gal-1hFc-binding, while Th2 cells showed poor binding activity as shown previously (FIG. 11A) (Motran, C. C., K. M. Molinder, S. D. Liu, F. Poirier, and M. C. Miceli. 2008. Galectin-1 functions as a Th2 cytokine that selectively induces Th1 apoptosis and promotes Th2 function. Eur J Immunol 38:3015-3027). Furthermore, compared with hFc, incubating Gal-1hFc with Th1 and Th17 cell cultures for 24 h reduced their viability as observed by assessing viable gating fractions (FIG. 11B) and by analysis of Annexin V-staining and propidium (PI) uptake (a marker of cell death) in a dose-dependent manner (FIG. 11C). Th2 cells and cultures containing lactose were largely resistant to cell death.

To further analyze the pro-apoptotic functions of Gal-Ig, growth-inhibitory effects on the Gal-1 ligand (+) J558L cells overexpressing Gal-Ig were investigated. Compared with control untransfected J558L cells, Gal-Ig-expressing J558L cells were actively exposing phosphatidylserine residues as evidenced by Annexin V staining. This feature was reversed by including 50 mM lactose in cultures.

This indicated that Gal-Ig, not only induced pro-apoptotic activity, but also triggered cell death. These effects were caused by Gal-Ig alone without any reducing agents and suggest that Gal-1-hFc can induce apoptosis on both Th1 and Th17 cells in the absence of reducing agents in vivo.

Example 5

Gal-Ig Induces Apoptosis on Human Leukemic HL-60 Cells

To evaluate the effect of the Gal-Ig construct on apoptosis in human leukemic cells, about $1 \times 10^6$ HL-60 cells were incubated in RPMI-1640 with 10% FBS, 1% Pen/Strep in the presence of Gal-Ig at concentrations of 10 mg/ml or 100 mg/ml, or vehicle (PBS). Apoptosis was assessed by flow cytometry with FITC-Annexin V and PI after 4 hours and at 24 hours post-incubation as follows. Synovial fluid cells, HL-60 cells or polarized mouse Th cell subsets ($1.5 \times 10^6$ cells/ml) were incubated with Gal-1hFc at 10 µg/ml or 100 µg/ml (+/−50 mM lactose) or with molecular controls for 12 h or 24 h in RPMI-1640/10% FBS/1% penicillin/streptomycin. Apoptotic cells were identified by staining with FITC-conjugated Annexin V and propidium iodide (PI). Cell viability was also determined by Trypan blue dye exclusion and forward/side scatter plots.

FIG. 13 shows the Gal-Ig concentration-dependent movement of cells from Annexin V negativity to positivity after a 4 hour incubation. Gal-Ig also caused a concentration-dependent movement from PI negativity to positivity after 24 hour incubation.

After 24 hours of incubation in Gal-Ig, forward and side scatter analysis revealed morphological changes suggestive of cell death. A reduction in the numbers of cells in the red outlined gate, where viable cells characteristically reside, is shown in FIG. 14.

In addition, the cells were analyzed by flow cytometry after 4 and 24 hours for pro-apoptotic changes (Annexin-V positivity) and for apoptosis (Annexin V and PI double positive cells. The results shown in FIGS. 15A-B are from experiments done in triplicate, where points show mean values.

To determine whether this effect is specific, the effect of the Galectin-1-binding antagonist, lactose, on Gal-Ig-induced cell death was tested.

$5 \times 10^5$ cells were incubated for 4 hours in the presence of 10 mg/ml or 100 mg/ml of Gal-Ig, then washed with cold PBS and resuspended in RPMI (10% FBS/1% Pen/strep) with or without 50 mM Lactose for 24 hours. Apoptosis was analyzed by FACS with Annexin V-FITC and PI. Experiments were done by triplicate, error bar showing S.D. The results, shown in FIG. 16A, demonstrated that lactose protects human leukemic HL-60 cells treated with Gal-Ig from cell death It is widely accepted that exogenous rGal-1 induces apoptosis on activated T cells and several hematopoietic cell lines after a short 4 h exposure (Perillo, N. L., K. E. Pace, J. J. Seilhamer, and L. G. Baum. 1995. Apoptosis of T cells mediated by galectin-1. Nature 378:736-739). However, more recently, this paradigm has been challenged, arguing that DTT, a reducing agent commonly added to culture conditions to prevent rGal-1 oxidative inactivation during cell death assays, is itself able to induce apoptosis. Moreover, studies show that while monomeric Gal-1 is unable to induce apoptosis, dimeric Gal-1 can induce transient phosphatidylserine (PS) exposure in leukocytes that is reversible upon Gal-1 removal or oxidative inactivation of the carbohydrate-recognition domain after a short 4 h incubation (Stowell, S. R., S. Karmakar, C. M. Arthur, T. Ju, L. C. Rodrigues, T. B. Riul, M. Dias-Baruffi, J. Miner, R. P. McEver, and R. D. Cummings. 2009. Galectin-1 induces reversible phosphatidylserine exposure at the plasma membrane. Mol Biol Cell 20:1408-1418; Stowell, S. R., M. Cho, C. L. Feasley, C. M. Arthur, X. Song, J. K. Colucci, S. Karmakar, P. Mehta, M. Dias-Baruffi, R. P. McEver, and R. D. Cummings. 2009. Ligand reduces galectin-1 sensitivity to oxidative inactivation by enhancing dimer formation. J Biol Chem 284:4989-4999). Importantly, data suggest that activated human T cells are resistant to Gal-1-mediated PS exposure when no DTT is present and that PS exposure does not lead to changes in the integrity of the plasma membrane, mitochondrial potential or nuclei, a scenario referred to as preaparesis (Stowell, S. R., S. Karmakar, C. J. Stowell, M. Dias-Baruffi, R. P. McEver, and R. D. Cummings. 2007. Human galectin-1, -2, and -4 induce surface exposure of phosphatidylserine in activated human neutrophils but not in activated T cells. Blood 109:219-227).

Figure 16C:
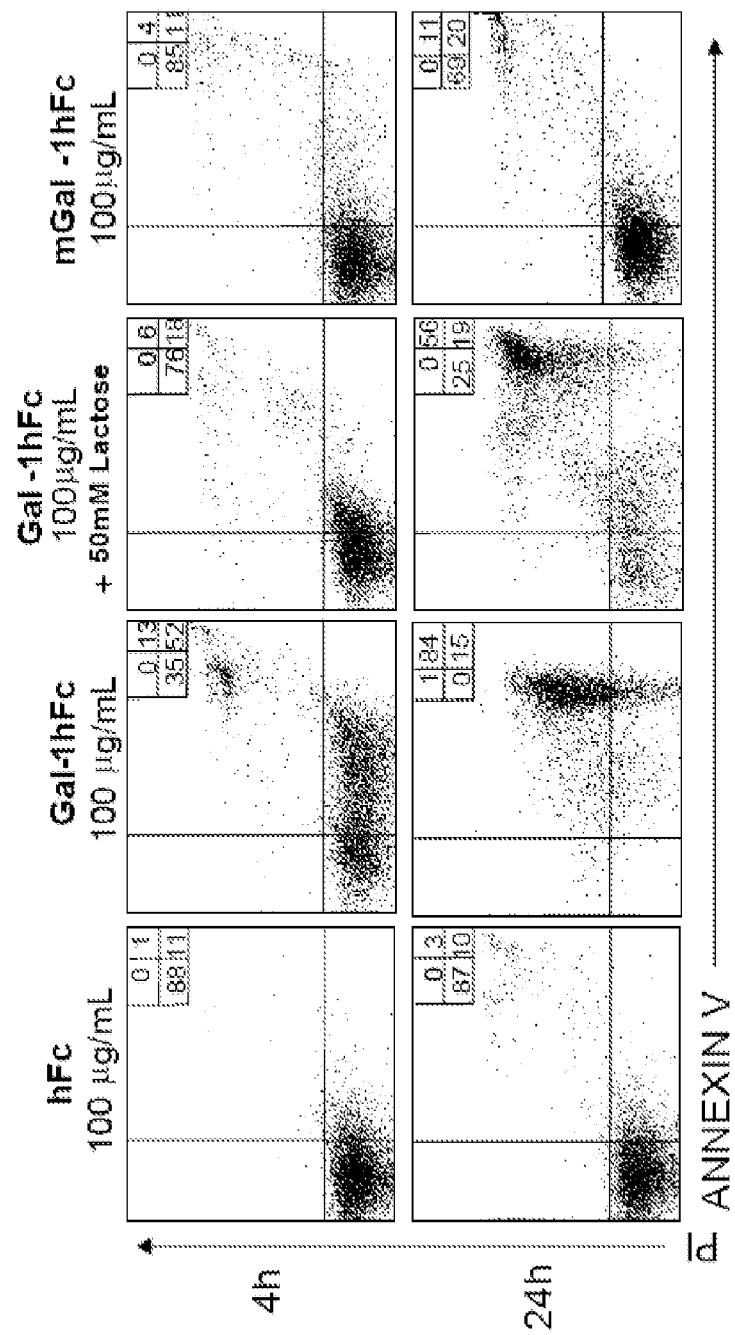

To help clarify these conflicting data, Gal-1hFc was compared with rGal-1 efficacy on cell death induction using human HL-60 leukemic cells. Incubations were performed at 100 µg/ml (~7 µM rGal-1/~2.4 µM Gal-1hFc), which enables rGal-1 homodimers to form, for a period of 4 or 24 hours in the presence or absence of DTT. At 4 h, rGal-1 caused marked PS exposure, as evidenced by Annexin V positivity, though PI staining was negative (FIG. 16B). To the contrary, when 1 mM DTT was incubated alone, both PS exposure and PI uptake were elevated (FIG. 16B). Furthermore, cells incubated with rGal-1 and DTT exhibited high levels of Annexin V staining (64%) and PI positivity (34%), which was partially blocked by including lactose (FIG. 16B). When incubations were increased to 24 h, rGal-1 and DTT caused complete PI positivity, while rGal-1 did not sustain PS exposure, indicating the labile nature of rGal-1 in the absence of DTT. In contrast, Gal-1hFc alone induced both PS exposure and PI uptake as early as 4 h and was sustained and enhanced over a 24 h period in the absence of DTT (FIG. 16C). These effects were averted by addition of lactose or by using mGal-1hFc, a lectin-binding control.

These results suggested that Gal-1hFc can engage cell surface ligands and trigger irreversible cell death, and provides evidence that Gal-Ig can control growth activities on human galectin-1 ligand+ cancer cells.

Example 6

Gal-1 hFc Induces an Array of Immunomodulatory Molecules and Alters Th Cell Subset Polarity Typically, when investigating pro-apoptotic effects, high concentrations of Gal-1 (>7 µM) with DTT are needed to ensure dimerization and a functional lectin domain. Though DTT helps prevent intracellular disulfide bond formation and retain carbohydrate-binding activity, they favor monomer formation, which are significantly less avid than native homodimers. This biochemical relationship could, therefore, undermine Gal-1's effects on other non-death-related pathways at lower, more physiologic concentrations. Some insights on Gal-1-related cytokine modulation have been gleaned from studies of the pathophysiology of Hodgkin's lymphoma, and from using mouse models of autoimmune diseases wherein Gal-1 presence upregulates Th2 cytokines and IL-10 (Juszczynski, P., J. Ouyang, S. Monti, S. J. Rodig, K. Takeyama, J. Abramson, W. Chen, J. L. Kutok, G. A. Rabinovich, and M. A. Shipp. 2007. The AP1-dependent secretion of galectin-1 by Reed Sternberg cells fosters immune privilege in classical Hodgkin lymphoma. Proc Natl Acad Sci USA 104:13134-13139; Perone, M. J., S. Bertera, W. J. Shufesky, S. J. Divito, A. Montecalvo, A. R. Mathers, A. T. Larregina, M. Pang, N. Seth, K. W. Wucherpfennig, M. Trucco, L. G Baum, and A. E. Morelli. 2009. Suppression of autoimmune diabetes by soluble galectin-1. J Immunol 182: 2641-2653). Similarly, studies using a leucine zipper-based Gal-1 homodimer showed 100-fold more secreted IL-10 than rGal-1 when incubated with human peripheral blood mononuclear cells (van der Leij, J., A. van den Berg, T. Blokzijl, G. Harms, H. van Goor, P. Zwiers, R. van Weeghel, S. Poppema, and L. Visser. 2004. Dimeric galectin-1 induces IL-10 production in T-lymphocytes: an important tool in the regulation of the immune response. J Pathol 204:511-518; van der Leij, J., A. van den Berg, G. Harms, H. Eschbach, H. Vos, P. Zwiers, R. van Weeghel, H. Groen, S. Poppema, and L. Visser. 2007. Strongly enhanced IL-10 production using stable galectin-1 homodimers. Mol Immunol 44:506-513). To expand on Gal-1-induced upregulation of IL-10, we investigated Gal-1hFc effects on a number of cytokines and immunomodulatory molecules in immuno-purified mouse and human T cells.

Mouse T cell cytokine analysis was performed as follows. CD4+ T cells isolated from naïve 6-week old C57/BL6 mouse spleens by immunomagnetic bead technology (Miltenyi Biotec) were stimulated with plate bound anti-mouse CD3 and soluble anti-mouse CD28 for 72 h. Then, after a 24 h incubation with Gal-1hFc or its controls, supernatants were collected in triplicate and analyzed for cytokine levels by using a mouse cytokine array (R&D Systems). Blots were processed as indicated by the manufacturer, and developed by chemiluminescence. Signal intensities were analyzed by optic densitometry (OD), using ImageJ Software®. OD values were normalized to control hFc treated group. In parallel, cells were stimulated with PMA/ionomycin and brefeldin A for 6 h to analyze intracellular cytokine levels by flow cytometric analysis.

Figure 17B:
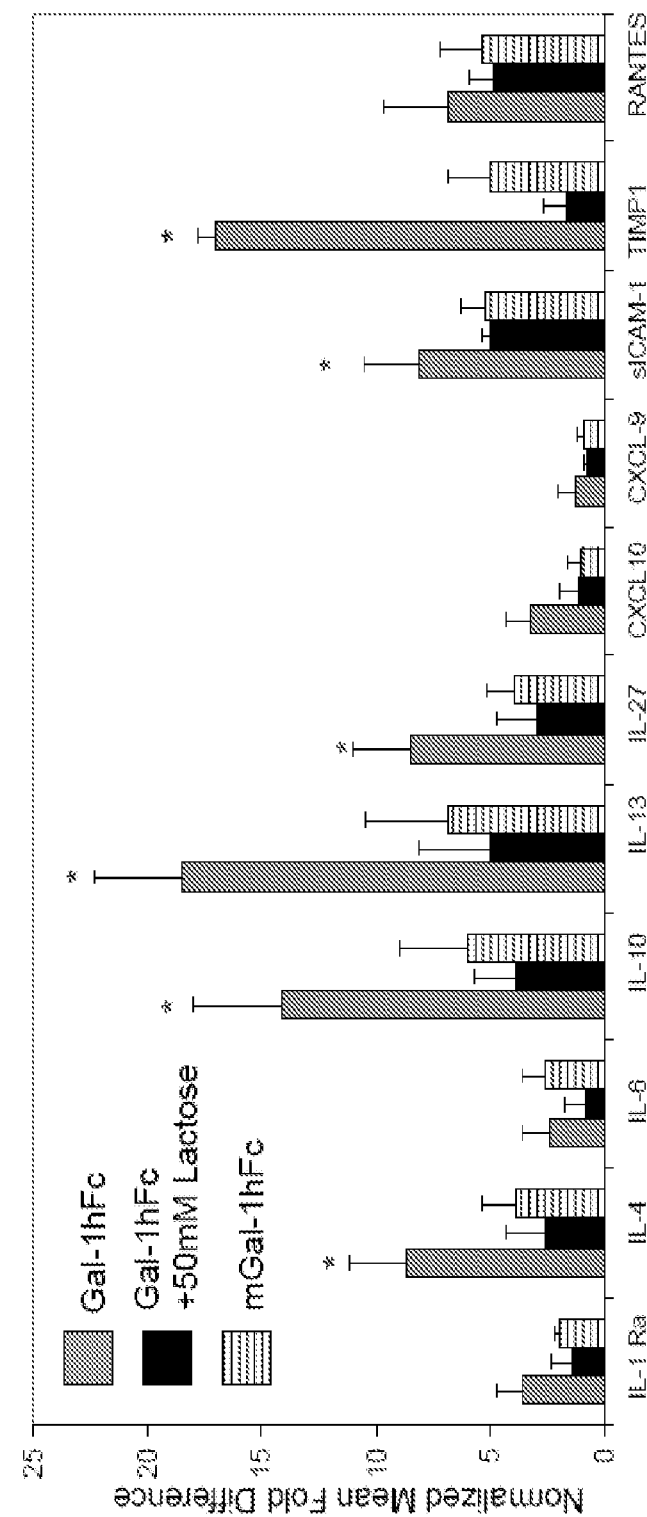

At 10-fold less Gal-1hFc used in death assays (10 µg/mL, 0.24 µM), activated mouse CD4+ T cells avidly bound Gal-1hFc, whereas naïve T cells did not express Gal-1 ligands (FIG. 17A). Using this concentration of Gal-1hFc, activated T cells were incubated for 24 h with or without lactose. Lectin-binding controls, mGal-1hFc, Gal-1hFc with lactose or hFc, were also employed in this assay. Supernatants were collected and examined for the expression of 40 different cytokines and other immunologic molecules by immunoblotting. Blots were scanned by optic densitometry and signal levels were normalized to hFc staining levels. Cells were concomitantly analyzed for cytokine modulation by intracellular cytokine staining Results showed that Gal-1hFc triggered the production/secretion of a number of immunoregulatory molecules, including IL-10, IL-1RA, soluble intercellular adhesion molecule-1 (sICAM-1), Th2 cytokines IL-4 and IL-13, chemokines CXCL-10 and RANTES and the anti-invasion molecule, tissue inhibitor of metalloproteinases (TIMP-1) in a carbohydrate-dependent manner (FIG. 17B-C). Similarly, intracellular cytokine analysis showed that Gal-1hFc enhanced expression of IL-4, IL-10 and IL-13 with little effect on IFN-gamma and IL-17 production. Experiments were performed in parallel using 10 µg/mL (0.71 µM) rGal-1 with or without DTT or lactose and showed that rGal-1 did not significantly up-regulate the expression of similar cytokines compared with Gal-1hFc. Graphical representations of data sets clearly depicted that Gal-1hFc caused significantly more potent IL-4, IL-10 and IL-13 induction than rGal-1 ($p<0.005$) (FIGS. 18 A and B). Moreover, in order to elucidate a role for Gal-1hFc in the induction of CD28 family members that mediate immunomodulation, we analyzed the expression of surface CTLA-4, PD-1 and ICOS in ex-vivo activated mouse T cell cultures after a 24 h incubation with 10 µg/mL Gal-1hFc. Interestingly, Gal-1hFc up-regulated the expression of CTLA-4 and PD-1 in a carbohydrate-dependent manner, as evidenced by its suppression after inclusion of 50 mM lactose (FIG. 18C). Nonetheless, expression of ICOS after Gal-1hFc treatment remained unaltered. Though CTLA-4 and PD-1 are associated with the phenotype and function of regulatory T cells (Kingsley, C. I., M. Karim, A. R. Bushell, and K. J. Wood. 2002. CD25+CD4+ regulatory T cells prevent graft rejection: CTLA-4- and IL-10-dependent immunoregulation of alloresponses. J Immunol 168:1080-1086; Chai, J. G., J. Y. Tsang, R. Lechler, E. Simpson, J. Dyson, and D. Scott. 2002. CD4+ CD25+ T cells as immunoregulatory T cells in vitro. Eur J Immunol 32:2365-2375; Kryczek, I., R. Liu, G. Wang, K. Wu, X. Shu, W. Szeliga, L. Vatan, E. Finlayson, E. Huang, D. Simeone, B. Redman, T. H. Welling, A. Chang, and W. Zou. 2009. FOXP3 defines regulatory T cells in human tumor and autoimmune disease. Cancer Res 69:3995-4000), the levels of $CD25^{high}$/FOXP3+ cells were relatively unchanged. However, most of Gal-1hFc-treated cells showed high levels of CD25 compared with cells treated with hFc or with Gal-1hFc and lactose (FIG. 18C).

To further explore Gal-1hFc-mediated IL-10 secretion and its potential of skewing T cell differentiation towards a Th2 profile, we studied Gal-1hFc effects on human skin-resident memory T cells. Normal healthy skin discarded from cosmetic surgeries was cultured on Cellfoam three-dimensional growth matrices in the presence of IL-2 and IL-15 for 21 days as previously described (Clark, R. A., B. F. Chong, N. Mirchandani, K. Yamanaka, G. F. Murphy, R. K. Dowgiert, and T. S. Kupper. 2006. A novel method for the isolation of skin resident T cells from normal and diseased human skin. J Invest Dermatol 126:1059-107). T cells were harvested from the matrices, washed with cold PBS and cultured for 24 h in the presence of Gal-1hFc (+/−50 mM lactose) or its molecular controls. Cells were stimulated with PMA/ionomycin and brefeldin A for 6 h before performing surface marker/cytokine/FOXP3 staining and analysis by flow cytometry.

Using human skin-explant cultures of skin-resident memory T cells (CD45RO+, CCR7−, cutaneous lymphocyte antigen (CLA+) (Clark, R. A., B. F. Chong, N. Mirchandani, K. Yamanaka, G. F. Murphy, R. K. Dowgiert, and T. S. Kupper. 2006. A novel method for the isolation of skin resident T cells from normal and diseased human skin. J Invest Dermatol 126:1059-107), we incubated Gal-1hFc for 24 h and analyzed cytokine levels by intracellular staining. This cell model characteristically produces high numbers of TNF-alpha/IL-17+ T cells (~70%) and a relatively high presence of $CD25^{high}$/FOXP3+ cells (Clark, R. A., B. F. Chong, N. Mirchandani, K. Yamanaka, G. F. Murphy, R. K. Dowgiert, and T. S. Kupper. 2006. A novel method for the isolation of skin resident T cells from normal and diseased human skin. J Invest Dermatol 126:1059-107: Clark, R. A., and T. S. Kupper. 2007. IL-15 and dermal fibroblasts induce proliferation of natural regulatory T cells isolated from human skin. Blood 109:194-202). Similar to mouse T cell data, when incubated with low concentrations of Gal-1hFc, a higher percentage of human skin-resident memory T cells expressed IL-4 and IL-10. To the contrary, a dramatically lower number of IL-17 producing T cells was observed, while TNF-alpha or IFN-gamma levels were largely unaffected. The number of $CD25^{high}$/FOXP3+ regulatory T cells did not appear to be altered. Statistical analysis of data sets from 6 different donors showed the significance of Gal-1hFc-induction of IL-4+ and IL-10+ T cells ($p<0.01$) and downregulation of IL-17+ T cells, indicating that Gal-1hFc can markedly affect cytokine production in human T cells (FIG. 19A).

Similar results were seen when naïve mouse T cells were activated ex vivo and incubated with low concentrations (0.2 µM) of Gal-1hFc or relevant controls. After 24 h, cells were stained IL-10/IL-4, IL-10/FoxP3, and IL-10/CD25. Gal-1hFc induced a Th2 cell phenotype and IL-10+ T cells that are IL-4 and FOXP3 negative (FIG. 19B). In addition, naïve mouse T cells were activated ex vivo, and incubated with low concentrations (0.2 µM) of Gal-1hFc for 24 h or 48 h. Cells were analyzed for CD4, IL-4, IL-10 and IFN-g was followed by flow cytometry. The results are shown in FIG. 19C.

Naïve mouse T cells were activated ex vivo and treated with Gal-1hFc or relevant controls for 8 hours. Total RNA from each group was extracted and reverse transcribed. Quantitative PCR (qRT-PCR) analysis to evaluate mRNA activity of GATA-3, IL-10 and T-bet transcripts was performed. The results, shown in FIG. 19D, indicate that Gal-1 hFc induces changes at the transcriptional level, favoring Th2 skewing and IL-10 expression.

These data demonstrate that Galectin-1-Ig induces a regulatory (suppressive) phenotype, while promoting an anti-inflammatory phenotype.

Example 7

Granulocytes Infiltrating Synovial Fluid from RA Patients are Susceptible to Gal-1 hFc-Mediated Cell Death Since Gal-1 plays a key regulatory molecule controlling the proliferation and viability of effector leukocytes, multiple researchers have tried to translate in vitro generated data to experimental animal models of inflammatory diseases. Prior data using mouse models of inflammation shows that Gal-1 can suppress experimental type 1 diabetes, autoimmune encephalomyelitis, uveitis, concanavalin A-induced hepatitis and graft-vs-host disease (Toscano, M. A., G. A. Bianco, J. M. Ilarregui, D. O. Croci, J. Correale, J. D. Hernandez, N. W. Zwirner, F. Poirier, E. M. Riley, L. G. Baum, and G. A. Rabinovich. 2007. Differential glycosylation of TH1, TH2 and TH-17 effector cells selectively regulates susceptibility to cell death. Nat Immunol 8:825-834; Perone, M. J., S. Bertera, W. J. Shufesky, S. J. Divito, A. Montecalvo, A. R. Mathers, A. T. Larregina, M. Pang, N. Seth, K. W. Wucherpfennig, M. Trucco, L. G Baum, and A. E. Morelli. 2009. Suppression of autoimmune diabetes by soluble galectin-1. J Immunol 182: 2641-2653; Toscano, M. A., A. G. Commodaro, J. M. Ilarregui, G. A. Bianco, A. Liberman, H. M. Serra, J. Hirabayashi, L. V. Rizzo, and G. A. Rabinovich. 2006. Galectin-1 suppresses autoimmune retinal disease by promoting concomitant Th2- and T regulatory-mediated anti-inflammatory responses. J Immunol 176:6323-6332; Santucci, L., S. Fiorucci, F. Cammilleri, G. Servillo, B. Federici, and A. Morelli. 2000. Galectin-1 exerts immunomodulatory and protective effects on concanavalin A-induced hepatitis in mice. Hepatology 31:399-406; Baum, L. G., D. P. Blackall, S. Arias-Magallano, D. Nanigian, S. Y. Uh, J. M. Browne, D. Hoffmann, C. E. Emmanouilides, M. C. Territo, and G. C. Baldwin. 2003. Amelioration of graft versus host disease by galectin-1. Clin Immunol 109:295-307). Of note, while T cells play an important role in the development of these disorders, relatively little is known about the anti-inflammatory properties of Gal-1 on other key cellular constituents, such as B cells and granulocytes. RA is an autoimmune disease that includes many different effector cell types, including B cells, neutrophils, monocytes/macrophages and mast cells, which play key roles in both induction and maintenance of disease.

To investigate Gal-1 efficacy as a putative anti-inflammatory agent in patients with RA, assayed apoptotic induction properties of Gal-1hFc on freshly-isolated leukocytes infiltrating synovial fluids of RA patients and incubated Gal-1hFc or control molecules.

Human knee synovial fluids were obtained as discarded material from patients with RA undergoing diagnostic or therapeutic arthrocentesis. RA was diagnosed by an American Board of Internal Medicine certified rheumatologist and/or by review of laboratory, radiologic and clinic notes and by applying ACR classification criteria (Arnett, F. C., S. M. Edworthy, D. A. Bloch, D. J. McShane, J. F. Fries, N. S. Cooper, L. A. Healey, S. R. Kaplan, M. H. Liang, H. S. Luthra, and et al. 1988. The American Rheumatism Association 1987 revised criteria for the classification of rheumatoid arthritis. Arthritis Rheum 31:315-324). All studies received Institutional Review Board approval. For FACS analyses and functional studies of cells contained in freshly-collected RA synovial fluids, cells were washed in cold PBS, stained with trypan blue for cell death exclusion, adjusted to $1\times10^6$ cells/100 µl FACS buffer, incubated for 20 min in FcγR-binding block and then subsequently stained for surface markers and analyzed by flow cytometry.

Figure 20A:
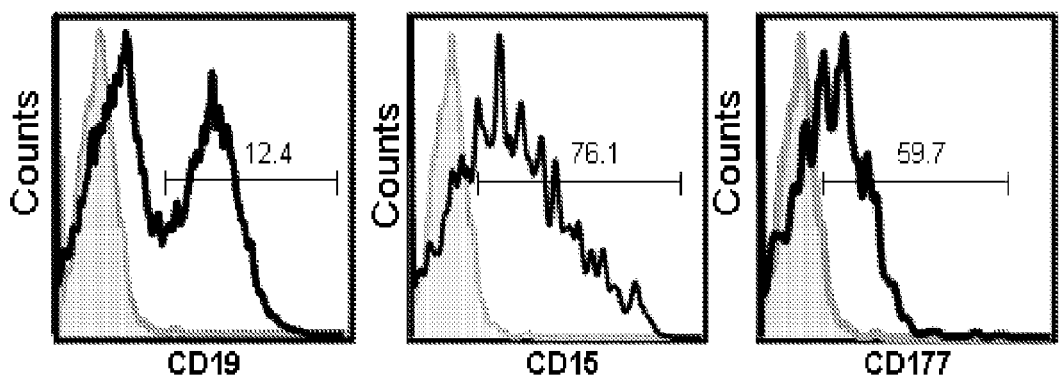
Figure 20B:
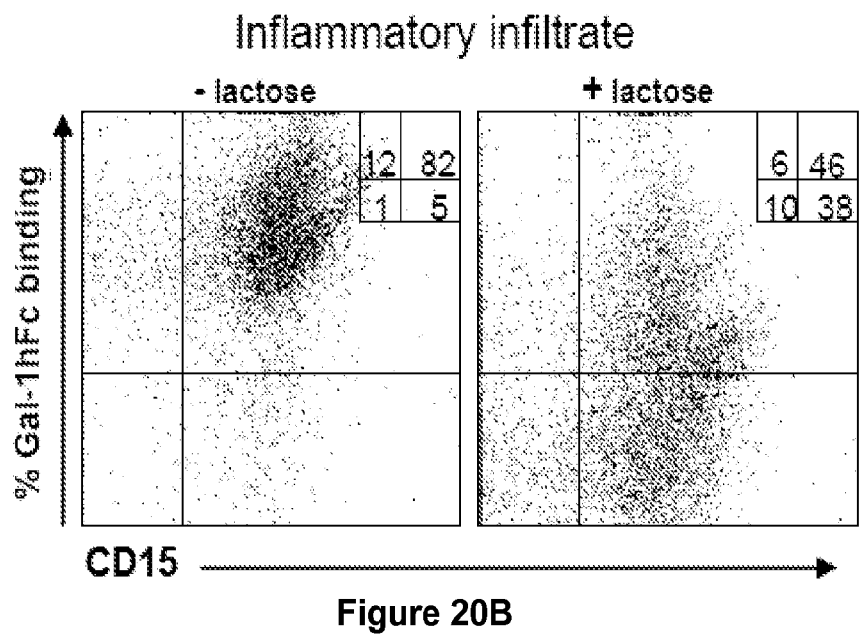
Figure 20C:
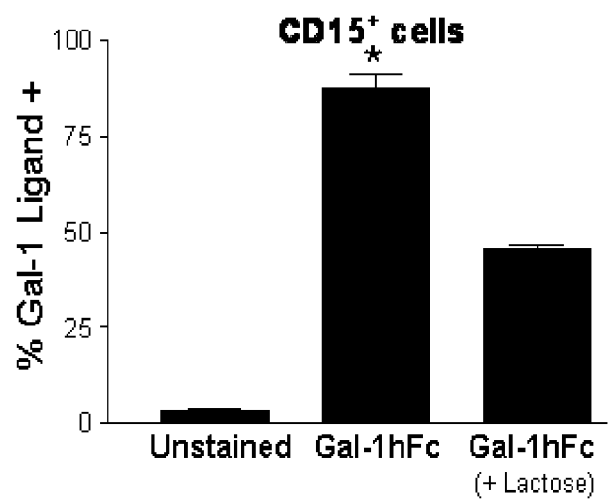
Figure 20D:
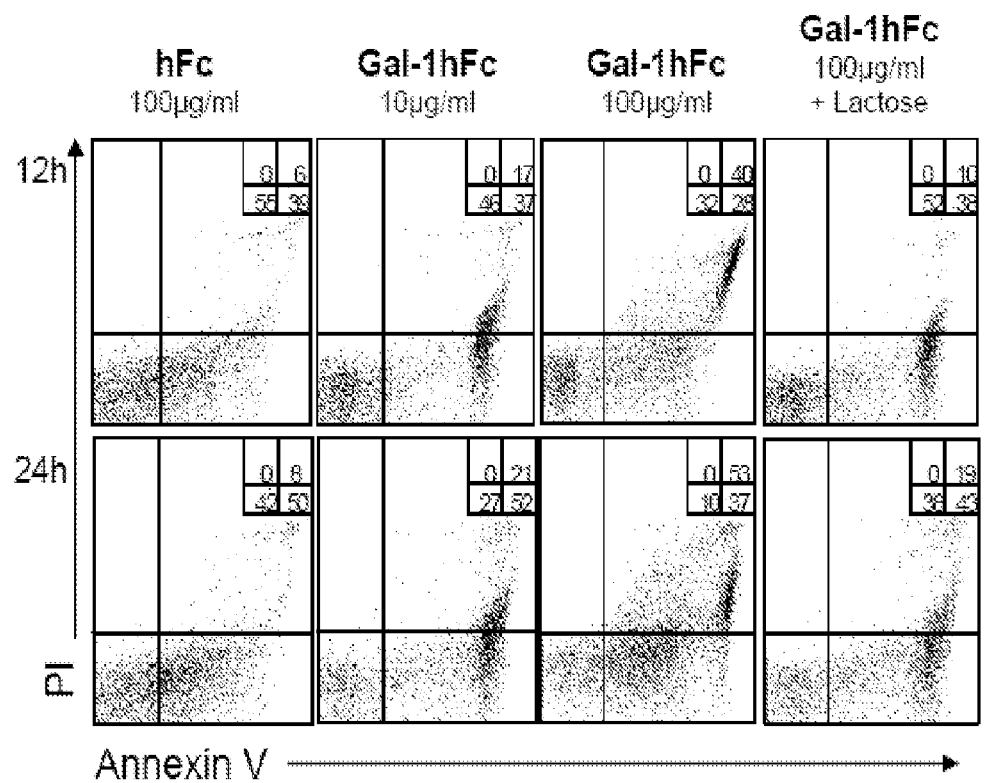
Figure 20E:
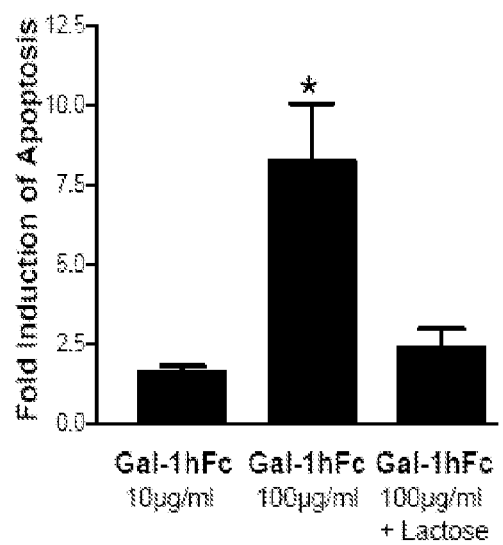

Infiltrates were freshly obtained and typically characterized by a moderate number of CD19+ B cells (12-20%) and abundant granulocytes (70-80%) identified by surface expression of CD15 (FIG. 20A). Among these, the most abundant cell type in synovial fluid infiltrates were neutrophils (CD177+). We first assessed whether Gal-1hFc could bind inflamed leukocytic infiltrates. The majority of inflammatory infiltrates (>80%) bound Gal-1hFc in a lactose-dependent manner and also expressed granulocytic marker, CD15 (FIGS. 20B and C). For cell death analysis leukocytic infiltrates were incubated for 12 or 24 h with Gal-1hFc or controls and assayed for trypan blue staining, Annexin V positivity and PI uptake by flow cytometric analysis. Results showed that, compared with hFc incubations, a large percentage of cells incubated with Gal-1hFc underwent apoptosis as determined by Annexin V/PI positivity, and this apoptosis was inhibited by the inclusion of lactose (FIGS. 20D and E).

These data suggest that, in addition to killing Th1 and Th17 subsets, Gal-1hFc can also be used to eliminate Gal-1 ligand (+) inflammatory granulocytes involved in arthritic conditions.

Example 8

In Vivo Gal-1hFc Treatment Triggers the Production of Immunomodulatory Molecules and Helps Ameliorate Hapten-Mediated Contact Hypersensitivity To address whether Gal-1hFc can bind activation-induced Gal-1 ligands in vivo, Gal-1hFc binding to activated mouse T cells was assayed in LNs draining antigen-sensitized skin.

For in vivo studies, mouse Gal-1 cDNA was fused in frame to the pFUSE hIgG1e3-Fc2 plasmid (Invivogen, San Diego, Calif.) to produce Gal-1hFc2. This vector carries specific mutations in the Fc domain that prevents Fc receptor-binding and complement and antibody-mediated cytotoxicity. Briefly, Gal-1 was subcloned from the Gal-1hFc vector with the following primers: Forward 5' ATTCGATATCTATGGC CTGTGGTCTGGTCGCCA 3' (SEQ ID NO: 15), Reverse 5' CCGAGATCTCTCAAAGGCCAC GCACTTAATCTT 3' (SEQ ID NO: 16), then digested PCR product with EcoRV and Bgl II, dephosphorylated with shrimp alkaline phosphatase, gel purified and ligated in frame to EcoRV/Bgl II digested pFUSE-e3 vector.

Shaved abdomens of 6-week old from C57BL/6 mice were painted on day 0 and day 1 with 25 uL of 0.5% 2,4-dinitrofluorobenzene (DNFB) or with 1% oxazolone (Sigma) in a 4:1 acetone:olive oil vehicle. To assess T cell activation during the afferent phase, draining inguinal lymph nodes (LN) were harvested on day 3, minced with frosted slides, and cells were stained with Gal-1hFc (+/−50 mM lactose) and antibodies to CD4 and CD69 and analyzed by flow cytometry. In vivo treatments with Gal-1hFc2 were administered i.p. at 50 µg per 22 g mouse on days 2, 4 and 5. Mice were alternatively treated with human Fc at an identical dose and served as a treatment control. Hapten-induced inflammation was then induced on day 5 by challenging mice with 10 µl of 0.25% DNFB or 0.5% oxazolone on both sides of the right ear, and as a negative inflammatory control, mice received 10 µl of vehicle alone on both sides of the left ear. Ear swelling responses were determined by calculating the difference in ear thickness between day 5 and day 6. To assess T cell cytokine levels, antigen-draining inguinal LNs were harvested and minced with frosted slides, and then lymphocytes were activated with PMA/ionomycin in the presence of brefeldin A for 6 h, stained for surface markers or intracellular cytokines and analyzed by flow cytometry. Following a 24 h challenge, ears were harvested, fixed in 10% formalin, embedded in paraffin, sectioned and stained with hematoxylin and eosin. Experiments were repeated 3-times.

Figure 21A:
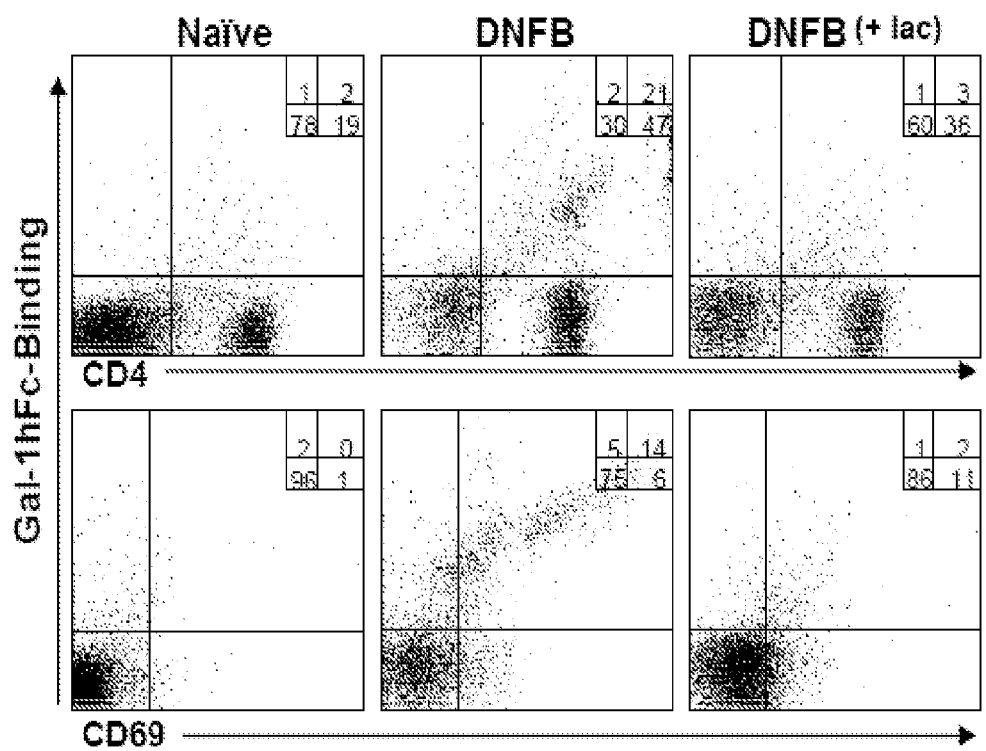

Gal-1hFc bound lymphocytes from LNs draining antigen-sensitized skin (FIG. 9A) and essentially only CD4+ cells, expressing the early activation marker CD69, were stained with Gal-1hFc in a carbohydrate-dependent manner (FIG. 21A).

Figure 21B:
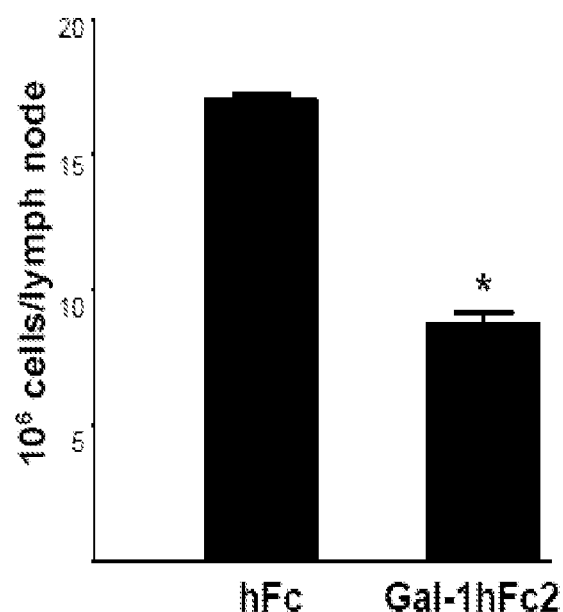
Figure 21C:
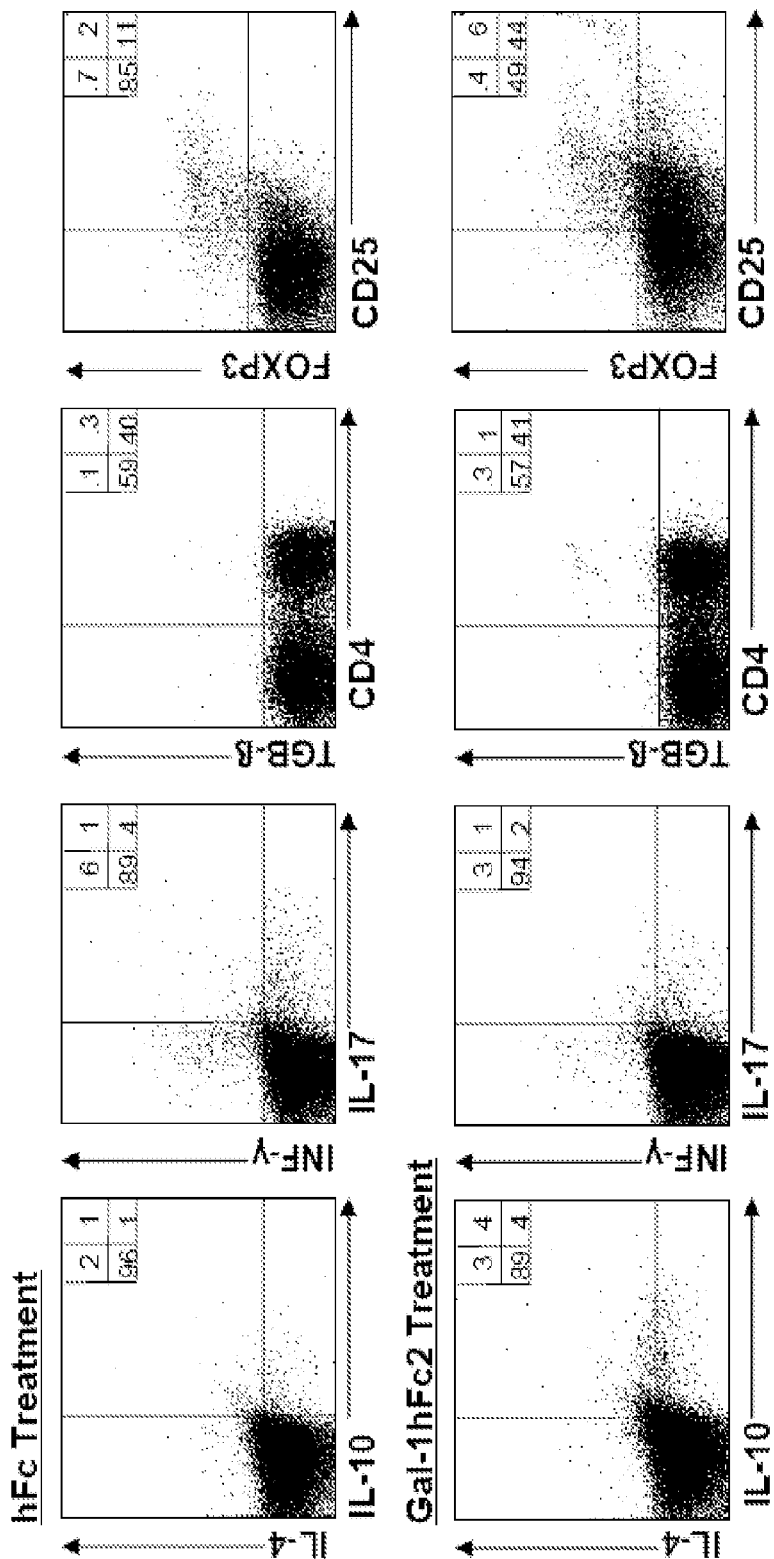
Figure 21D:
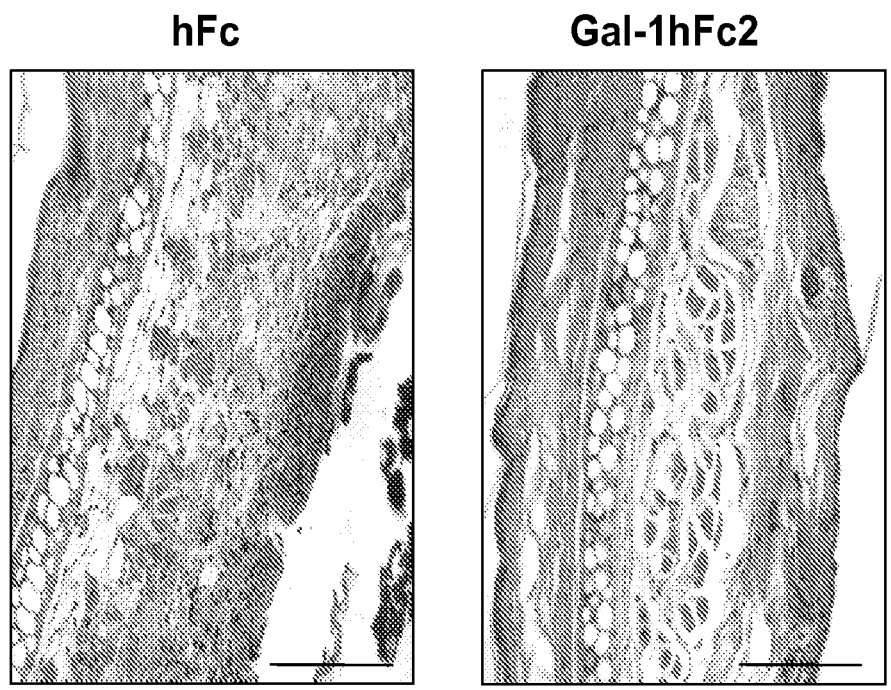
Figure 21E:
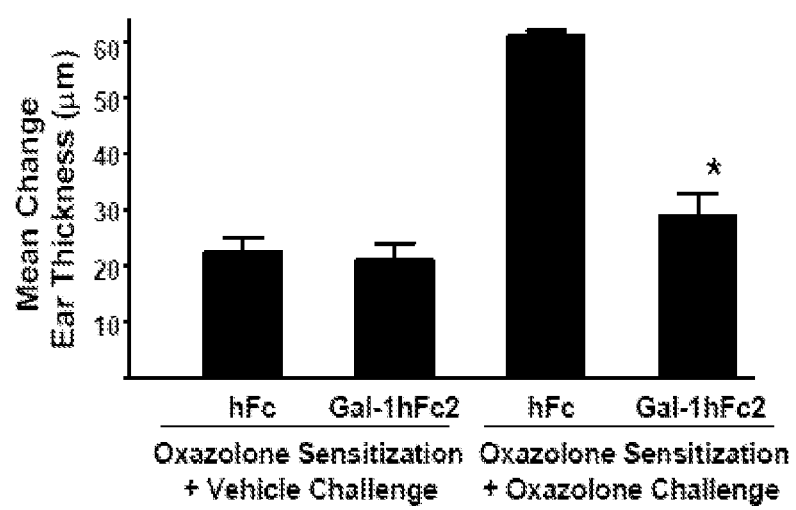

To study Gal-1 specific effects in vivo, a Gal-1hFc variant, Gal-1hFc2, was developed as described above that contains a mutated Fc region that prevents binding to Fc receptors and minimize potential complement and antibody-dependent cytotoxicity. Gal-1hFc2 retained identical morphological and binding activity as Gal-1hFc (data not shown). To investigate Gal-1hFc2 anti-inflammatory efficacy, a model of hapten-mediated contact hypersensitivity was employed that consisted of oxazolone-sensitization on the abdomen on day 0 and 1 and oxazolone (or vehicle alone)-challenge on the ear on day 5. Gal-1hFc2 or hFc control (both at 50 μg/22 g mouse) was administered to mice on day 2, 4 and 5. On day 5, baseline ear thickness measurements were calculated on the right ear or vehicle alone on the left ear. After 24 h, to assess inflammation, ear thickness was re-measured and a mean change in ear thickness was computed. In addition, ear skin was analyzed for leukocytic infiltrate, and lymphocytes were harvested from oxazolone-draining LNs, enumerated and then analyzed for cytokine expression. Gal-1hFc2-treated mice exhibited a significantly lower level of lymphocytes in draining LNs compared with hFc-treated mice (p<0.01; paired t-test) (FIG. 21B). Flow cytometric analysis revealed that lymphocytes from Gal-1hFc2-treated mice exhibited increased levels of IL-4+, IL-10+ and TGF-β+ cells and lower levels of IFN-γ+ and IL-17+ cells (FIG. 21C). Of note, the percentage of CD25high/FOXP3+ cells was increased 2-fold in Gal-1hFc2-treated mice compared to the hFc-treatment control. Along with induction of immunoregulatory cytokines, leukocytic infiltrate in inflamed skin was markedly decreased (FIG. 21D), and change in ear thickness was significantly abrogated in Gal-hFc2-treated mice compared with that in vehicle alone challenged ears (FIG. 21E).

These results indicate that in vivo administration of a Gal-1hFc fusion protein can be therapeutically useful in models of an autoimmune disease characterized by the presence of activated auto-reactive T cells.

ADDITIONAL REFERENCES

M. J. Perone, S. Bertera, W. J. Shufesky et al., J Immunol 182 (5), 2641 (2009)

L. G. Baum, D. P. Blackall, S. Arias-Magallano et al., Clin Immunol 109 (3), 295 (2003)

C.-M. Tsai, Y.-K. Chiu, T.-L. Hsu et al., J. Immunology. 181(7):4570-4579 (2008)

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated Galectin-1-Ig (Gal-Ig) fusion construct, comprising: a first portion comprising a mouse Galectin-1 polypeptide comprising SEQ ID NO:2, and a second portion comprising an Fc fragment of a human IgG1 immunoglobulin linked in frame with the first portion, optionally with a linker sequence between the first and second portions.

2. The isolated fusion construct of claim 1, wherein the mouse Galectin-1 binds to glycoconjugates bearing N-acetyl-lactosamine (LacNAc) Type 1 (Galβ1,3GlcNAc) or Type 2 (Galβ1-4GlcNAc) disaccharides.

3. The isolated fusion construct of claim 1, wherein the human IgG1 Fc fragment comprises SEQ ID NO: 4.

4. A pharmaceutical composition comprising the Gal-Ig fusion construct of claim 1, and a physiologically acceptable carrier.

5. The isolated fusion construct of claim 1, comprising SEQ ID NO:17.

* * * * *

UNITED STATES PATENT AND TRADEMARK OFFICE
CERTIFICATE OF CORRECTION

| | | |
|---|---|---|
| PATENT NO. | : 8,598,323 B2 | Page 1 of 1 |
| APPLICATION NO. | : 13/378229 | |
| DATED | : December 3, 2013 | |
| INVENTOR(S) | : Charles J. Dimitroff et al. | |

It is certified that error appears in the above-identified patent and that said Letters Patent is hereby corrected as shown below:

In the Specification

In Column 1, Line 15, delete "This invention was made with Government support under Grant No. ROI AT004628-01A1 awarded by the National Center for Complementary and Alternative Medicine at the National Institutes of Health. The Government has certain rights in the invention." and insert -- This invention was made with Government support under Grant No(s). AT004628 and CA118124 awarded by the National Institutes of Health. The Government has certain rights in this invention. --

Signed and Sealed this
Seventeenth Day of June, 2014

Michelle K. Lee
*Deputy Director of the United States Patent and Trademark Office*

SEQUENCE LISTING

```
<160> NUMBER OF SEQ ID NOS: 17

<210> SEQ ID NO 1
<211> LENGTH: 135
<212> TYPE: PRT
<213> ORGANISM: Mus musculus

<400> SEQUENCE: 1

Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
    130                 135

<210> SEQ ID NO 2
<211> LENGTH: 135
<212> TYPE: PRT
<213> ORGANISM: Homo sapiens
```

-continued

```
<400> SEQUENCE: 2

Met Ala Cys Gly Leu Val Ala Ser Asn Leu Asn Leu Lys Pro Gly Glu
  1               5                  10                  15

Cys Leu Lys Val Arg Gly Glu Val Ala Ser Asp Ala Lys Ser Phe Val
                 20                  25                  30

Leu Asn Leu Gly Lys Asp Ser Asn Asn Leu Cys Leu His Phe Asn Pro
             35                  40                  45

Arg Phe Asn Ala His Gly Asp Ala Asn Thr Ile Val Cys Asn Thr Lys
 50                  55                  60

Glu Asp Gly Thr Trp Gly Thr Glu His Arg Glu Pro Ala Phe Pro Phe
 65                  70                  75                  80

Gln Pro Gly Ser Ile Thr Glu Val Cys Ile Thr Phe Asp Gln Ala Asp
                 85                  90                  95

Leu Thr Ile Lys Leu Pro Asp Gly His Glu Phe Lys Phe Pro Asn Arg
            100                 105                 110

Leu Asn Met Glu Ala Ile Asn Tyr Met Ala Ala Asp Gly Asp Phe Lys
            115                 120                 125

Ile Lys Cys Val Ala Phe Glu
            130                 135

<210> SEQ ID NO 3
<211> LENGTH: 135
<212> TYPE: PRT
<213> ORGANISM: Artificial Sequence
<220> FEATURE:
<223> OTHER INFORMATION: mouse/human consensus sequence
<220> FEATURE:
<221> NAME/KEY: VARIANT
<222> LOCATION: 19
<223> OTHER INFORMATION: Xaa = Arg or Lys
<220> FEATURE:
<221> NAME/KEY: VARIANT
<222> LOCATION: 26
<223> OTHER INFORMATION: Xaa = Pro or Ser
<220> FEATURE:
<221> NAME/KEY: VARIANT
<222> LOCATION: 63
<223> OTHER INFORMATION: Xaa = Ser or Thr
<220> FEATURE:
<221> NAME/KEY: VARIANT
<222> LOCATION: 65
<223> OTHER INFORMATION: Xaa = Asp or Glu
<220> FEATURE:
<221> NAME/KEY: VARIANT
<222> LOCATION: 66
<223> OTHER INFORMATION: Xaa = Gly or Asp
<220> FEATURE:
<221> NAME/KEY: VARIANT
<222> LOCATION: 68
<223> OTHER INFORMATION: Xaa = Ala or Thr
<220> FEATURE:
<221> NAME/KEY: VARIANT
<222> LOCATION: 73
<223> OTHER INFORMATION: Xaa = Gln or His
<220> FEATURE:
<221> NAME/KEY: VARIANT
<222> LOCATION: 76
<223> OTHER INFORMATION: Xaa = Ala or Pro
<220> FEATURE:
<221> NAME/KEY: VARIANT
<222> LOCATION: 77
<223> OTHER INFORMATION: Xaa = Val or Ile
<220> FEATURE:
<221> NAME/KEY: VARIANT
<222> LOCATION: 85
<223> OTHER INFORMATION: Xaa = Val or Ile
<220> FEATURE:
<221> NAME/KEY: VARIANT
<222> LOCATION: 86
<223> OTHER INFORMATION: Xaa = Ala or Thr
```

```
<220> FEATURE:
<221> NAME/KEY: VARIANT
<222> LOCATION: 96
<223> OTHER INFORMATION: Xaa = Asn or Asp
<220> FEATURE:
<221> NAME/KEY: VARIANT
<222> LOCATION: 99
<223> OTHER INFORMATION: Xaa = Val or Ile
<220> FEATURE:
<221> NAME/KEY: VARIANT
<222> LOCATION: 105
<223> OTHER INFORMATION: Xaa = Tyr or His
<220> FEATURE:
<221> NAME/KEY: VARIANT
<222> LOCATION: 115
<223> OTHER INFORMATION: Xaa = Leu or Met
<220> FEATURE:
<221> NAME/KEY: VARIANT
<222> LOCATION: 135
<223> OTHER INFORMATION: Xaa = Asp or Glu

<400> SEQUENCE: 3

Met Ala Cys Gly Leu Val Ala Ser Asn Leu Asn Leu Lys Pro Gly Glu
 1               5                  10                  15

Cys Leu Xaa Val Arg Gly Glu Val Ala Xaa Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Xaa Lys
    50                  55                  60

Xaa Xaa Gly Xaa Trp Gly Thr Glu Xaa Arg Glu Xaa Xaa Phe Pro Phe
65                  70                  75                  80

Gln Pro Gly Ser Xaa Xaa Glu Val Cys Ile Thr Phe Asp Gln Ala Xaa
                85                  90                  95

Leu Thr Xaa Lys Leu Pro Asp Gly Xaa Glu Phe Lys Phe Pro Asn Arg
            100                 105                 110

Leu Asn Xaa Glu Ala Ile Asn Tyr Met Ala Ala Asp Gly Asp Phe Lys
        115                 120                 125

Ile Lys Cys Val Ala Phe Xaa
    130                 135

<210> SEQ ID NO 4
<211> LENGTH: 227
<212> TYPE: PRT
<213> ORGANISM: Homo sapiens

<400> SEQUENCE: 4

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
```

```
                115              120              125
Tyr Thr Leu Pro Pro Ser Arg Glu Glu Met Thr Lys Asn Gln Val Ser
    130              135              140

Leu Thr Cys Leu Val Lys Gly Phe Tyr Pro Ser Asp Ile Ala Val Glu
145              150              155              160

Trp Glu Ser Asn Gly Gln Pro Glu Asn Asn Tyr Lys Thr Thr Pro Pro
            165              170              175

Val Leu Asp Ser Asp Gly Ser Phe Phe Leu Tyr Ser Lys Leu Thr Val
                180              185              190

Asp Lys Ser Arg Trp Gln Gln Gly Asn Val Phe Ser Cys Ser Val Met
            195              200              205

His Glu Gly Leu His Asn His Tyr Thr Gln Lys Ser Leu Ser Leu Ser
    210              215              220

Pro Gly Lys
225

<210> SEQ ID NO 5
<211> LENGTH: 34
<212> TYPE: DNA
<213> ORGANISM: Artificial Sequence
<220> FEATURE:
<223> OTHER INFORMATION: synthetically generated oligonucleotide

<400> SEQUENCE: 5
cgacctcgag gccacccgtc tctcgggtgg agtc                              34

<210> SEQ ID NO 6
<211> LENGTH: 33
<212> TYPE: DNA
<213> ORGANISM: Artificial Sequence
<220> FEATURE:
<223> OTHER INFORMATION: synthetically generated oligonucleotide

<400> SEQUENCE: 6
ccgagatctc tcaaaggcca cgcacttaat ctt                               33

<210> SEQ ID NO 7
<211> LENGTH: 506
<212> TYPE: DNA
<213> ORGANISM: Mus musculus

<400> SEQUENCE: 7
cgacctcgag gccacccgtc tctcgggtgg agtcttctga ctgctggtgg agcaggtctc    60
aggaatctct tcgcttcagc ttcaatcatg gcctgtggtc tggtcgccag caacctgaat   120
ctcaaacctg gggaatgtct caaagttcgg ggagaggtgg cctcggacgc caagagcttt   180
gtgctgaacc tgggaaaaga cagcaacaac ctgtgcctac acttcaatcc tcgcttcaat   240
gcccatggag acgccaacac cattgtgtgt aacaccaagg aagatgggac ctggggaacc   300
gaacaccggg aacctgcctt ccccttccag cccgggagca tcacagaggt gtgcatcacc   360
tttgaccagg ctgacctgac catcaagctg ccagacggac atgaattcaa gttccccaac   420
cgcctcaaca tggaggccat caactacatg gcggcggatg gagacttcaa gattaagtgc   480
gtggcctttg agtgaagaga tctcgg                                        506

<210> SEQ ID NO 8
<211> LENGTH: 1035
<212> TYPE: DNA
<213> ORGANISM: Artificial Sequence
<220> FEATURE:
<223> OTHER INFORMATION: synthetically generated construct
```

<220> FEATURE:
<221> NAME/KEY: misc_feature
<222> LOCATION: 1-11, 15-22, 783, 858, 937, 940, 971-972, 977, 980, 982,
      990, 998, 1001-1002, 1005-1006, 1008, 1010, 1015-1016, 1019, 1024,
      1027-1028, 1030-1033
<223> OTHER INFORMATION: n = A,T,C or G

<400> SEQUENCE: 8

```
nnnnnnnnnn ntgcnnnnnn nnatccagct gtgaccggcg cctacctgag atcaccggtg    60
aattcgatat ctcgaggcca cccgtctctc gggtggagtc ttctgactgc tggtggagca   120
ggtctcagga atctcttcgc ttcagcttca atcatggcct gtggtctggt cgccagcaac   180
ctgaatctca aacctgggga atgtctcaaa gttcggggag aggtggcctc ggacgccaag   240
agctttgtgc tgaacctggg aaaagacagc aacaacctgt gcctacactt caatcctcgc   300
ttcaatgccc atggagacgc caacaccatt gtgtgtaaca ccaaggaaga tgggacctgg   360
ggaaccgaac accgggaacc tgccttcccc ttccagcccg ggagcatcac agaggtgtgc   420
atcacctttg accaggctga cctgaccatc aagctgccag acggacatga attcaagttc   480
cccaaccgcc tcaacatgga ggccatcaac tacatggcgg cggatggaga cttcaagatt   540
aagtgcgtgg cctttgagag atctgacaaa actcacacat gcccaccgtg cccagcacct   600
gaactcctgg ggggaccgtc agtcttcctc ttccccccaa acccaaggac caccctcatg   660
atctcccgga cccctgaggt cacatgcgtg gtggtggacg tgagccacga agaccctgag   720
gtcaagttca actggtacgt ggacggcgtg gaggtgcata atgccaagac aaagccgcgg   780
gangagcagt acaacagcac gtaccgtgtg gtcagcgtcc tcaccgtcct gcaccaggac   840
tggctgaatg gcaagganta caagtgcaag gtctccaaca agccctccc agcccccatc    900
gagaaaacca tctccaaagc caagggcag ccccgana acacaggtgta caccctgccc    960
ccatcccggg nngagangan cnagaaccan gtcagccnga nntgnntngn caaanctnc   1020
tatnccnncn nnntc                                                    1035
```

<210> SEQ ID NO 9
<211> LENGTH: 135
<212> TYPE: PRT
<213> ORGANISM: Mus musculus

<400> SEQUENCE: 9

```
Met Ala Cys Gly Leu Val Ala Ser Asn Leu Asn Leu Lys Pro Gly Glu
  1               5                  10                  15

Cys Leu Lys Val Arg Gly Glu Val Ala Ser Asp Ala Lys Ser Phe Val
             20                  25                  30

Leu Asn Leu Gly Lys Asp Ser Asn Asn Leu Cys Leu His Phe Asn Pro
         35                  40                  45

Arg Phe Asn Ala His Gly Asp Ala Asn Thr Ile Val Cys Asn Thr Lys
     50                  55                  60

Glu Asp Gly Thr Gly Gly Thr Glu His Arg Glu Pro Ala Phe Pro Phe
 65                  70                  75                  80

Gln Pro Gly Ser Ile Thr Glu Val Cys Ile Thr Phe Asp Gln Ala Asp
                 85                  90                  95

Leu Thr Ile Lys Leu Pro Asp Gly His Glu Phe Lys Phe Pro Asn Arg
            100                 105                 110

Leu Asn Met Glu Ala Ile Asn Tyr Met Ala Ala Asp Gly Asp Phe Lys
        115                 120                 125

Ile Lys Cys Val Ala Phe Glu
    130                 135
```

```
<210> SEQ ID NO 10
<211> LENGTH: 135
<212> TYPE: PRT
<213> ORGANISM: Drosophila

<400> SEQUENCE: 10

Met Ala Cys Gly Leu Val Ala Ser Asn Leu Asn Leu Lys Pro Gly Glu
  1               5                  10                  15

Cys Leu Lys Val Arg Gly Glu Val Ala Ser Asp Ala Lys Ser Phe Val
                 20                  25                  30

Leu Asn Leu Gly Lys Asp Ser Asn Asn Leu Cys Leu Leu Phe Asn Pro
             35                  40                  45

Arg Phe Asn Ala His Gly Asp Ala Asn Thr Ile Val Cys Asn Thr Lys
         50                  55                  60

Glu Asp Gly Thr Gly Gly Thr Glu His Arg Glu Pro Ala Phe Pro Phe
 65                  70                  75                  80

Gln Pro Gly Ser Ile Thr Glu Val Cys Ile Thr Phe Asp Gln Ala Asp
                 85                  90                  95

Leu Thr Ile Lys Leu Pro Asp Gly His Glu Phe Lys Phe Pro Asn Arg
            100                 105                 110

Leu Asn Met Glu Ala Ile Asn Tyr Met Ala Ala Asp Gly Asp Phe Lys
            115                 120                 125

Ile Lys Cys Val Ala Phe Glu
            130         135

<210> SEQ ID NO 11
<211> LENGTH: 33
<212> TYPE: DNA
<213> ORGANISM: Artificial Sequence
<220> FEATURE:
<223> OTHER INFORMATION: synthetically generated oligonucleotide

<400> SEQUENCE: 11
accaaggaag atgggaccgg gggaaccgaa cac                                 33

<210> SEQ ID NO 12
<211> LENGTH: 30
<212> TYPE: DNA
<213> ORGANISM: Artificial Sequence
<220> FEATURE:
<223> OTHER INFORMATION: synthetically generated oligonucleotide

<400> SEQUENCE: 12
ggtcccatct tccttggtgt tacacacaat                                     30

<210> SEQ ID NO 13
<211> LENGTH: 30
<212> TYPE: DNA
<213> ORGANISM: Artificial Sequence
<220> FEATURE:
<223> OTHER INFORMATION: synthetically generated oligonucleotide

<400> SEQUENCE: 13
acaacctgtg cctactcttc aatcctcgct                                     30

<210> SEQ ID NO 14
<211> LENGTH: 30
<212> TYPE: DNA
<213> ORGANISM: Artificial Sequence
<220> FEATURE:
<223> OTHER INFORMATION: synthetically generated oligonucleotide

<400> SEQUENCE: 14
```

-continued

```
gtaggcacag gttgttgctg tctcttccca                                    30

<210> SEQ ID NO 15
<211> LENGTH: 33
<212> TYPE: DNA
<213> ORGANISM: Artificial Sequence
<220> FEATURE:
<223> OTHER INFORMATION: synthetically generated oligonucleotide

<400> SEQUENCE: 15
attcgatatc tatggcctgt ggtctggtcg cca                                33

<210> SEQ ID NO 16
<211> LENGTH: 33
<212> TYPE: DNA
<213> ORGANISM: Artificial Sequence
<220> FEATURE:
<223> OTHER INFORMATION: synthetically generated oligonucleotide

<400> SEQUENCE: 16
ccgagatctc tcaaaggcca cgcacttaat ctt                                33

<210> SEQ ID NO 17
<211> LENGTH: 364
<212> TYPE: PRT
<213> ORGANISM: Artificial Sequence
<220> FEATURE:
<223> OTHER INFORMATION: generated Galectin-1/Fc chimera

<400> SEQUENCE: 17

Met Ala Cys Gly Leu Val Ala Ser Asn Leu Asn Leu Lys Pro Gly Glu
  1               5                  10                  15

Cys Leu Lys Val Arg Gly Glu Val Ala Ser Asp Ala Lys Ser Phe Val
             20                  25                  30

Leu Asn Leu Gly Lys Asp Ser Asn Asn Leu Cys Leu His Phe Asn Pro
         35                  40                  45

Arg Phe Asn Ala His Gly Asp Ala Asn Thr Ile Val Cys Asn Thr Lys
     50                  55                  60

Glu Asp Gly Thr Trp Gly Thr Glu His Arg Glu Pro Ala Phe Pro Phe
 65                  70                  75                  80

Gln Pro Gly Ser Ile Thr Glu Val Cys Ile Thr Phe Asp Gln Ala Asp
                 85                  90                  95

Leu Thr Ile Lys Leu Pro Asp Gly His Glu Phe Lys Phe Pro Asn Arg
            100                 105                 110

Leu Asn Met Glu Ala Ile Asn Tyr Met Ala Ala Asp Gly Asp Phe Lys
        115                 120                 125

Ile Lys Cys Val Ala Phe Glu Arg Ser Asp Lys Thr His Thr Cys Pro
    130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
```

-continued

```
225                 230                 235                 240
Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
                260                 265                 270

Glu Glu Met Thr Lys Asn Gln Val Ser Leu Thr Cys Leu Val Lys Gly
            275                 280                 285

Phe Tyr Pro Ser Asp Ile Ala Val Glu Trp Glu Ser Asn Gly Gln Pro
        290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Gly Leu His Asn His
                340                 345                 350

Tyr Thr Gln Lys Ser Leu Ser Leu Ser Pro Gly Lys
            355                 360
```